United States Patent
Selvarajah et al.

(10) Patent No.: US 10,532,980 B2
(45) Date of Patent: Jan. 14, 2020

(54) N-METHYL PYRAZOLES

(71) Applicant: Prosetta Antiviral, Inc., San Francisco, CA (US)

(72) Inventors: Suganya Selvarajah, San Francisco, CA (US); Kumar Paulvannan, San Jose, CA (US)

(73) Assignee: Prosetta Antiviral, Inc., San Francisco, CA (US)

( * ) Notice: Subject to any disclaimer, the term of this patent is extended or adjusted under 35 U.S.C. 154(b) by 0 days.

(21) Appl. No.: 15/561,933

(22) PCT Filed: Mar. 30, 2016

(86) PCT No.: PCT/US2016/025073
§ 371 (c)(1),
(2) Date: Sep. 26, 2017

(87) PCT Pub. No.: WO2016/161021
PCT Pub. Date: Oct. 6, 2016

(65) Prior Publication Data
US 2018/0118679 A1 May 3, 2018

Related U.S. Application Data

(60) Provisional application No. 62/140,315, filed on Mar. 30, 2015.

(51) Int. Cl.
*C07D 207/36* (2006.01)
*A61P 31/12* (2006.01)
*A61P 31/16* (2006.01)

(52) U.S. Cl.
CPC ............ *C07D 207/36* (2013.01); *A61P 31/12* (2018.01); *A61P 31/16* (2018.01)

(58) Field of Classification Search
None
See application file for complete search history.

(56) References Cited

FOREIGN PATENT DOCUMENTS

| JP | 2011 001293 A | 1/2011 |
|---|---|---|
| WO | WO 2006/050034 A1 | 5/2006 |

OTHER PUBLICATIONS

U.S. Appl. No. 11/903,494 (filed Sep. 20, 2007), now abandoned.
U.S. Appl. No. 10/346,654 (filed Jan. 17, 2003), now U.S. Pat. No. 7,348,134.
U.S. Appl. No. 10/243,509 (filed Sep. 13, 2002), now U.S. Pat. No. 7,638,269.
U.S. Appl. No. 10/040,206 (filed Jan. 2, 2002), now abandoned.
U.S. Appl. No. 09/020,144 (filed Feb. 6, 1998), now U.S. Pat. No. 6,593,103.
U.S. Appl. No. 10/527,973 (filed Aug. 2, 2006), now abandoned.
U.S. Appl. No. 11/473,460 (filed Jun. 22, 2006), now abandoned; U.S. Pat Pub. No. 2007-0015211 (Jan. 18, 2007).
U.S. Appl. No. 11/567,142 (filed Dec. 5, 2006), now abandoned; U.S. Pat Pub. No. 2007-0202537 (Aug. 30, 2007).
U.S. Appl. No. 11/955,337 (filed Dec. 12, 2007), now abandoned; U.S. Pat Pub. No. 2009-0155761(Jun. 18, 2009).
U.S. Appl. No. 12/062,491 (filed Apr. 3, 2008), now U.S. Pat. No. 8,227,459; U.S. Pat Pub. No. 2011-0178071 (Oct. 16, 2008).
U.S. Appl. No. 12/699,831 (filed Feb. 3, 2010), now abandoned; U.S. Pat Pub. No. 2010-0211327 (Aug. 19, 2010).
U.S. Appl. No. 13/099,006 (filed May 2, 2011), now U.S. Pat. No. 8,785,434; U.S. Pat Pub. No. 2012-0157435 (Jun. 21, 2012).
U.S. Appl. No. 13/316,423 (filed Dec. 9, 2011), now U.S. Pat. No. 8,796, 448.
U.S. Appl. No. 13/423,141 (filed Mar. 16, 2012), now U.S. Pat. No. 8,759,336; U.S. Pat Pub. No. 2012-0238543 (Sep. 20, 2012).
U.S. Appl. No. 13/433,378 (filed Mar. 29, 2012), now U.S. Pat. No. 8,809,317; U.S. Pat Pub. No. 2012-0302556 (Nov. 29, 2012).
U.S. Appl. No. 13/451,608 (filed Apr. 20, 2012), now U.S. Pat. No. 8,828,986; U.S. Pat Pub. No. 2012-0270854 (Oct. 25, 2012).
U.S. Appl. No. 13/457,481 (filed Apr. 26, 2012), now abandoned; U.S. Pat Pub. No. 2012-0301904 (Nov. 29, 2012).
U.S. Appl. No. 13/566,897 (filed Aug. 3, 2012), now abandoned; U.S. Pat Pub. No. 2013-0053267 (Feb. 28, 2013).
U.S. Appl. No. 13/950,232 (filed Jul. 24, 2013), now abandoned; U.S. Pat Pub. No. 2014-0106365 (Apr. 17, 2014).
U.S. Appl. No. 14/677,819 (filed Apr. 2, 2015) U.S. Pat Pub. No. 2015-0226748 (Aug. 13, 2015).
U.S. Appl. No. 14/970,393 (filed Dec. 15, 2015), now U.S. Pat. No. 9,518,022 U.S. Pat Pub. No. 2016-0168100 (Jun. 16, 2016).
U.S. Appl. No. 15/427,993 (filed Feb. 8, 2017) U.S. Pat Pub. No. 2017-0159097 (Jun. 8, 2017).
XP-002757451 Database Registry, Chemical Abstract, 1 page.
XP-002757452 Database Registry, Chemical Abstract, 1 page.
XP-002757453 Database Registry, Chemical Abstract, 1 page.
XP-002757454 Database Registry, Chemical Abstract, 1 page.
XP-002757455 Database Registry, Chemical Abstract, 1 page.
XP-002757456 Database Registry, Chemical Abstract, 1 page.
XP-002757457 Database Registry, Chemical Abstract, 1 page.
XP-002757458 Database Registry, Chemical Abstract, 1 page.
XP-002757459 Database Registry, Chemical Abstract, 1 page.
XP-002757460 Database Registry, Chemical Abstract, 1 page.
XP-002757461 Database Registry, Chemical Abstract, 1 page.

*Primary Examiner* — Kamal A Saeed
(74) *Attorney, Agent, or Firm* — Morgan, Lewis & Bockius LLP

(57) ABSTRACT

This invention provides, among other things, compounds useful for treating viral infections, pharmaceutical formulations containing such compounds, as well as methods of inhibiting the replication of a virus or treating a disease.

36 Claims, No Drawings

N-METHYL PYRAZOLES

CROSS-REFERENCE TO RELATED APPLICATIONS

This application is a United States National Stage Application filed under 35 U.S.C. § 371 of International Patent Application No. PCT/US2016/025073 filed Mar. 30, 2016 and published as WO 2016/161021 A1, which claims priority to U.S. Provisional Application No. 62/140,315 filed Mar. 30, 2015, the entire contents of which applications is incorporated herein for all purposes by this reference.

BACKGROUND OF THE INVENTION

There is a need in the art to discover new compounds useful as antivirals.

It has now been discovered that certain N-methyl pyrazoles are surprisingly effective antivirals. This, and other uses of these compounds are described herein.

SUMMARY OF THE INVENTION

This invention provides, among other things, novel compounds useful for treating viral infections, pharmaceutical formulations containing such compounds, as well as methods of inhibiting the replication of a virus or treating a disease.

In an exemplary embodiment, the invention provides a compound of formula (I) or formula (II):

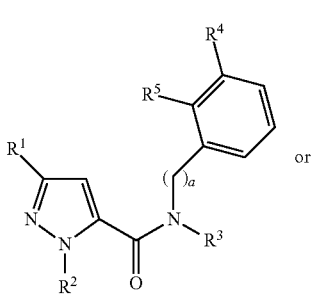

(I)

or

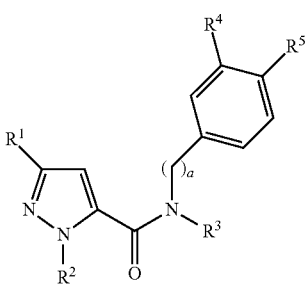

(II)

in which $R^1$ and $R^2$ are each independently selected from linear alkyl, branched alkyl, and cycloalkyl; $R^3$ is H; a is an integer selected from 1, 2, 3, 4, 5, and 6; $R^4$ and $R^5$ are each independently selected from linear alkyl, halogen-substituted linear alkyl, branched alkyl, halogen-substituted branched alkyl, cycloalkyl, halogen-substituted linear alkoxy, halogen-substituted branched alkoxy, cycloalkoxy, and halogen, with the proviso that either $R^4$ or $R^5$ is halogen. Also provided are hydrates, salts and solvates of these compounds.

In an exemplary embodiment, there is provided a pharmaceutical formulation comprising a compound of the invention and a pharmaceutically acceptable diluent or carrier.

Also provided is a method of treating an animal infected with corona virus, e.g., porcine epidemic diarrheal virus (PEDV). The method comprises, administering to the animal a therapeutically effective amount of a compound of the invention, thereby treating the animal. In an exemplary embodiment, the animal is a pig.

Other embodiments, objects and advantages of the invention are apparent from the detailed description that follows.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino) pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide;

NH$_4$Cl is ammonium chloride; NIS is N-iodosuccinimide; N$_2$ is nitrogen; NMM is N-methylmorpholine; n-BuLi is n-butyllithium; overnight is O/N; PdCl$_2$(pddf) is 1,1'-Bis (diphenylphosphino) ferroceneldichloropalladium(II); Pd/C is the catalyst known as palladium on carbon; Pd$_2$(dba)$_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; POCl$_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—NH$_2$ is amino-functionalized silica, available from SiliCycle; Si-pyr is pyridyl-functionalized silica, available from SiliCycle; TEA or Et$_3$N is triethylamine; TFA is trifluoroacetic acid; Tf$_2$O is trifluoromethanesulfonic anhydride; THF is tetrahydrofuran; TFAA is trifluoroacetic anhydride; THP is tetrahydropyranyl; TMSI is trimethylsilyl iodide; H$_2$O is water; diNO$_2$PhSO$_2$Cl is dinitrophenyl sulfonyl chloride; 3-F-4-NO$_2$-PhSO$_2$Cl is 3-fluoro-4-nitrophenylsulfonyl chloride; 2-MeO-4-NO$_2$-PhSO$_2$Cl is 2-methoxy-4-nitrophenylsulfonyl chloride; and (EtO)$_2$POCH$_2$COOEt is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to a radical of a molecule that is attached to the remainder of the molecule.

The symbol ∿, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of O, N and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R"', —OC(O)R', —C(O)R', —CO$_2$R', —CONR'R", —OC(O)NR"R", —NR"C(O)R', —NR'—C(O)NR"R"', —NR"C(O)$_2$R', —NR""—C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to (2m'+1), where m' is the total number of carbon atoms in such radical. R', R", R"', R"" and R"""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"', R"" and R""" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R"', —OC(O)R', —C(O)R', —CO$_2$R', —CONR'R", —OC(O)NR"R", —NR"C(O)R', —NR'—C(O)NR"R"', —NR"C(O)$_2$R', —NR""-C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', R"" and R""" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"', R"" and R""" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted $C_1$ or $C_2$ or $C_3$ or $C_4$ or $C_5$ or $C_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "pharmaceutically effective," or "therapeutically effective" amount refers to the amount of drug needed to effect the desired therapeutic result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). The compounds may also be labeled with stable isotopes such as deuterium. All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the animal. Representative carriers include water, oils, both vegetable and mineral, cream bases, lotion bases, ointment bases and the like. These bases include suspending agents, thickeners, penetration enhancers, and the like. Their formulation is well known to those in the pharmaceutical arts. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the animal. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Salt counterion", as used herein, refers to positively charged ions that associate with a compound of the invention. Examples of salt counterions include $H^+$, $H_3O^+$, ammonium, potassium, calcium, magnesium, organic amino (such as choline or diethylamine or amino acids such as d-arginine, l-arginine, d-lysine, l-lysine), and sodium.

II. Introduction

The invention provides N-methyl pyrazoles, as well as pharmaceutical formulations containing such compounds or combinations of these compounds with at least one additional therapeutically effective agent, can be used for, among other things, treating viral infections.

III. The Compounds

III.a)

In one aspect, the invention provides a compound of the invention. In an exemplary embodiment, the invention is a compound described herein. In an exemplary embodiment, the invention is a compound according to a formula described herein.

In an exemplary embodiment, the invention provides a compound of formula (III) or formula (IV) or formula (V):

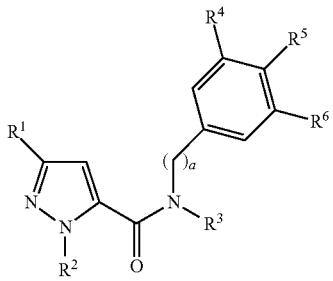
(III)

or

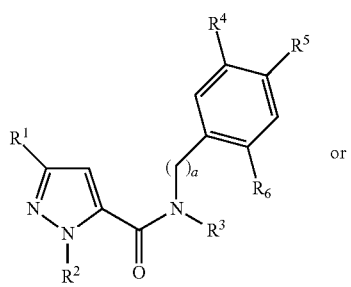
(IV)

or

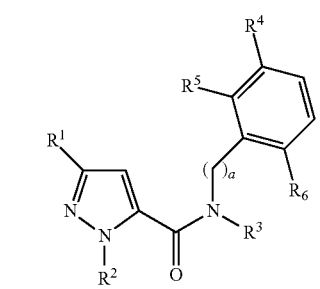
(V)

in which $R^1$ and $R^2$ are each independently selected from linear alkyl, branched alkyl, and cycloalkyl; $R^3$ is H; a is an integer selected from 1, 2, 3, 4, 5, and 6; $R^4$ and $R^5$ are each independently selected from the group consisting of linear alkyl, halogen-substituted linear alkyl, branched alkyl, halogen-substituted branched alkyl, cycloalkyl, halogen-substituted linear alkoxy, halogen-substituted branched alkoxy, cycloalkoxy, cycloalkylalkoxy, hydroxy, and halogen; and $R^6$ is selected from the group consisting of H, linear alkyl, halogen-substituted linear alkyl, branched alkyl, halogen-substituted branched alkyl, cycloalkyl, halogen-substituted linear alkoxy, halogen-substituted branched alkoxy, cycloalkoxy, cycloalkylalkoxy, and halogen, with the proviso that $R^4$ and $R^5$ are optionally joined to form, along with the atoms to which they are connected, a 5- to 8-membered ring. Also provided are hydrates, salts and solvates of these compounds.

In an exemplary embodiment, the invention provides a compound of formula (III) or formula (IV) or formula (V):

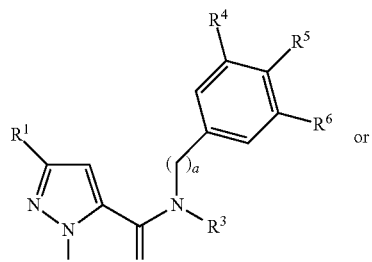
(III)

or

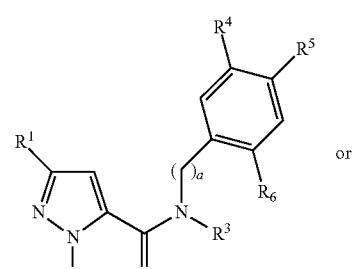
(IV)

or

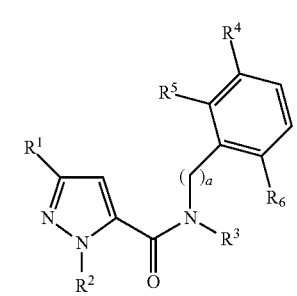
(V)

in which $R^1$ and $R^2$ are each independently selected from linear alkyl, branched alkyl, and cycloalkyl; $R^3$ is H; a is an integer selected from 1, 2, 3, 4, 5, and 6; $R^4$, $R^5$, and $R^6$ are each independently selected from the group consisting of linear alkyl, halogen-substituted linear alkyl, branched alkyl, halogen-substituted branched alkyl, cycloalkyl, halogen-substituted linear alkoxy, halogen-substituted branched alkoxy, cycloalkoxy, cycloalkylalkoxy, hydroxy and halogen. Also provided are hydrates, salts and solvates of these compounds.

In an exemplary embodiment, the invention provides a compound of formula (I) or formula (II):

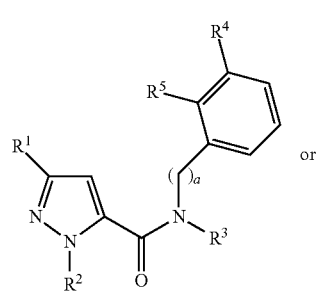
(I)

or

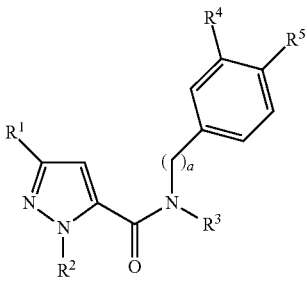

or in which $R^1$ and $R^2$ are each independently selected from linear alkyl, branched alkyl, and cycloalkyl; $R^3$ is H; a is an integer selected from 1, 2, 3, 4, 5, and 6; $R^4$ and $R^5$ are each independently selected from linear alkyl, halogen-substituted linear alkyl, branched alkyl, halogen-substituted branched alkyl, cycloalkyl, halogen-substituted linear alkoxy, halogen-substituted branched alkoxy, cycloalkoxy, cycloalkylalkoxy, hydroxy, and halogen. Also provided are hydrates, salts and solvates of these compounds.

In an exemplary embodiment, the invention provides a compound of formula (I) or formula (II), in which $R^1$ and $R^2$ are each independently selected from linear alkyl, branched alkyl, and cycloalkyl; $R^3$ is H; a is an integer selected from 1, 2, 3, 4, 5, and 6; $R^4$ and $R^5$ are each independently selected from linear alkyl, halogen-substituted linear alkyl, branched alkyl, halogen-substituted branched alkyl, cycloalkyl, halogen-substituted linear alkoxy, halogen-substituted branched alkoxy, cycloalkoxy, cycloalkylalkoxy, and halogen, with the proviso that either $R^4$ or $R^5$ is halogen. Also provided are hydrates, salts and solvates of these compounds.

In an exemplary embodiment, the invention provides a compound of formula (I) or formula (II), in which $R^1$ and $R^2$ are each independently selected from linear alkyl, branched alkyl, and cycloalkyl; $R^3$ is H; a is an integer selected from 1, 2, 3, 4, 5, and 6; $R^4$ and $R^5$ are each independently selected from linear alkyl, halogen-substituted linear alkyl, branched alkyl, halogen-substituted branched alkyl, cycloalkyl, halogen-substituted linear alkoxy, halogen-substituted branched alkoxy, cycloalkoxy, and cycloalkylalkoxy. Also provided are hydrates, salts and solvates of these compounds.

In an exemplary embodiment, the compound is of formula (III) or formula (IV) or formula (V), or a salt, or a hydrate, or a solvate thereof, a, $R^1$, $R^2$, $R^3$, $R^4$, and $R^5$ are as described herein, and $R^6$ is H.

In an exemplary embodiment, the compound is of formula (I), or a salt, or a hydrate, or a solvate thereof, and a, $R^1$, $R^2$, $R^3$, $R^4$, and $R^5$ are as described herein. In an exemplary embodiment, the compound is of formula (II), or a salt, or a hydrate, or a solvate thereof, a, $R^1$, $R^2$, $R^3$, $R^4$, and $R^5$ are as described herein. In an exemplary embodiment, the compound is of formula (III), or a salt, or a hydrate, or a solvate thereof, and a, $R^1$, $R^2$, $R^3$, $R^4$, $R^5$, and $R^6$ are as described herein. In an exemplary embodiment, the compound is of formula (IV), or a salt, or a hydrate, or a solvate thereof, a, $R^1$, $R^2$, $R^3$, $R^4$, $R^5$, and $R^6$ are as described herein. In an exemplary embodiment, the compound is of formula (V), or a salt, or a hydrate, or a solvate thereof, and a, $R^1$, $R^2$, $R^3$, $R^4$, $R^5$, and $R^6$ are as described herein.

In an exemplary embodiment, the compound is of formula (I) or formula (II), or a salt, or a hydrate, or a solvate thereof, $R^1$, $R^2$, $R^3$, $R^4$, and $R^5$ are as described herein, and a is 1. In an exemplary embodiment, the compound is of formula (I) or formula (II), or a salt, or a hydrate, or a solvate thereof, $R^1$, $R^2$, $R^3$, $R^4$, and $R^5$ are as described herein, and a is 2. In an exemplary embodiment, the compound is of formula (I) or formula (II), or a salt, or a hydrate, or a solvate thereof, $R^1$, $R^2$, $R^3$, $R^4$, and $R^5$ are as described herein, and a is 3. In an exemplary embodiment, the compound is of formula (I) or formula (II), or a salt, or a hydrate, or a solvate thereof, $R^1$, $R^2$, $R^3$, $R^4$, and $R^5$ are as described herein, and a is 4.

In an exemplary embodiment, the compound is of formula (III) or formula (IV) or formula (V), or a salt, or a hydrate, or a solvate thereof, $R^1$, $R^2$, $R^3$, $R^4$, $R^5$, and $R^6$ are as described herein, and a is 1. In an exemplary embodiment, the compound is of formula (III) or formula (IV) or formula (V), or a salt, or a hydrate, or a solvate thereof, $R^1$, $R^2$, $R^3$, $R^4$, $R^5$, and $R^6$ are as described herein, and a is 2. In an exemplary embodiment, the compound is of formula (III) or formula (IV) or formula (V), or a salt, or a hydrate, or a solvate thereof, $R^1$, $R^2$, $R^3$, $R^4$, $R^5$, and $R^6$ are as described herein, and a is 3. In an exemplary embodiment, the compound is of formula (III) or formula (IV) or formula (V), or a salt, or a hydrate, or a solvate thereof, $R^1$, $R^2$, $R^3$, $R^4$, $R^5$, and $R^6$ are as described herein, and a is 4.

In an exemplary embodiment, the compound is of formula (I), or a salt, or a hydrate, or a solvate thereof, $R^1$, $R^2$, $R^3$, $R^4$, and $R^5$ are as described herein, and a is 1. In an exemplary embodiment, the compound is of formula (II), or a salt, or a hydrate, or a solvate thereof, $R^1$, $R^2$, $R^3$, $R^4$, and $R^5$ are as described herein, and a is 1.

In an exemplary embodiment, the compound is of formula (III), or a salt, or a hydrate, or a solvate thereof, $R^1$, $R^2$, $R^3$, $R^4$, $R^5$, and $R^6$ are as described herein, and a is 1. In an exemplary embodiment, the compound is of formula (IV), or a salt, or a hydrate, or a solvate thereof, $R^1$, $R^2$, $R^3$, $R^4$, $R^5$, and $R^6$ are as described herein, and a is 1. In an exemplary embodiment, the compound is of formula (V), or a salt, or a hydrate, or a solvate thereof, $R^1$, $R^2$, $R^3$, $R^4$, $R^5$, and $R^6$ are as described herein, and a is 1.

In an exemplary embodiment, the compound is of formula (I) or formula (II), or a salt, or a hydrate, or a solvate thereof, a, $R^1$, $R^2$, $R^4$, and $R^5$ are as described herein, and $R^3$ is H.

In an exemplary embodiment, the compound is of formula (III) or formula (IV) or formula (V), or a salt, or a hydrate, or a solvate thereof, a, $R^1$, $R^2$, $R^4$, $R^5$, and $R^6$ are as described herein, and $R^3$ is H.

In an exemplary embodiment, the compound is of formula (I) or formula (II), or a salt, or a hydrate, or a solvate thereof, a, $R^1$, $R^3$, $R^4$, and $R^5$ are as described herein, and $R^2$ is methyl.

In an exemplary embodiment, the compound is of formula (III) or formula (IV) or formula (V), or a salt, or a hydrate, or a solvate thereof, a, $R^1$, $R^3$, $R^4$, $R^5$, and $R^6$ are as described herein, and $R^2$ is methyl.

In an exemplary embodiment, the compound is of formula (I) or formula (II), or a salt, or a hydrate, or a solvate thereof, a, $R^2$, $R^3$, $R^4$, and $R^5$ are as described herein, and $R^1$ is $C_1$-$C_6$ alkyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is $C_1$-$C_4$ alkyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is methyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is ethyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is propyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is isopropyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is butyl or isobutyl or sec-butyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is t-butyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is $C_5$ alkyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is $C_6$ alkyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is $C_3$-$C_8$ cycloalkyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is cyclopropyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is cyclobutyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is cyclopentyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is cyclohexyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is cycloheptyl. In an exemplary embodiment, the compound is of formula (I) or formula (II), or a salt, or a hydrate, or a solvate thereof, a, $R^2$, $R^3$, $R^4$, and $R^5$ are as described herein, and $R^1$ is cyclooctyl.

In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is $C_1$-$C_6$ alkyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is $C_1$-$C_4$ alkyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is methyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is ethyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is propyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is isopropyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is butyl or isobutyl or sec-butyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is t-butyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is $C_5$ alkyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is $C_6$ alkyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is $C_3$-$C_8$ cycloalkyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is cyclopropyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is cyclobutyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is cyclopentyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is cyclohexyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is cycloheptyl. In an exemplary embodiment, the compound is of formula (III) or formula (IV) or formula (V), or a salt, or a hydrate, or a solvate thereof, a, $R^2$, $R^3$, $R^4$, $R^5$, and $R^6$ are as described herein, and $R^1$ is cyclooctyl.

In an exemplary embodiment, the compound is of formula (I) or formula (II), or a salt, or a hydrate, or a solvate thereof, a, $R^1$, $R^2$, $R^3$, and $R^5$ are as described herein, and $R^4$ is methyl. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is methoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is halosubstituted alkyl. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is halosubstituted methyl. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is trifluoromethyl. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is halosubstituted alkoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is halosubstituted methoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is trifluoromethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is difluoromethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is ethyl. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is ethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is propoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclopropyloxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclobutoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclopentoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclohexoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclopropylalkyloxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclobutylalkyloxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclopentylalkyloxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclohexylalkyloxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclopropylmethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclopropylethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclobutylmethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclobutylethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclopentylmethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclopentylethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclohexylmethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is cyclohexylethoxy. In an exemplary embodiment, the compound is of formula (I) or formula (II), or a salt, or a hydrate, or a solvate thereof, a, $R^1$, $R^2$, $R^3$, and $R^5$ are as described herein, and $R^4$ is hydroxy.

In an exemplary embodiment, the compound is of formula (I) or formula (II), or a salt, or a hydrate, or a solvate thereof, a, $R^1$, $R^2$, $R^3$, and $R^4$ are as described herein, and $R^5$ is methyl. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is methoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is halosubstituted alkyl. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is halosubstituted methyl. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is trifluoromethyl. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is halosubstituted alkoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is halosubstituted methoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is trifluoromethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is difluoromethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is ethyl. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is ethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is propoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclopropyloxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclobutoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclopentoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclohexoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclopropylalkyloxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclobutylalkyloxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclopentylalkyloxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclohexylalkyloxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclopropylmethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclopropylethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclobutylmethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclobutylethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclopentylmethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclopentylethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclohexylmethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is cyclohexylethoxy. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is hydroxy.

In an exemplary embodiment, the compound is of formula (I) or formula (II), or a salt, or a hydrate, or a solvate thereof, a, $R^1$, $R^2$, $R^3$, and $R^4$ are as described herein, and $R^5$ is $C_3$-$C_6$ alkyl. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is methyl. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is ethyl. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is F. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is Cl. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is Br. In an exemplary embodiment, the compound is of formula (I) or formula (II), or a salt, or a hydrate, or a solvate thereof, a, $R^1$, $R^2$, $R^3$, and $R^4$ are as described herein, and $R^5$ is I.

In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is $C_1$-$C_6$ alkyl. In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is methyl. In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is ethyl. In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is propyl or isopropyl. In an exemplary embodiment, the compound is of formula (I) or formula (II), or a salt, or a hydrate, or a solvate thereof, a, $R^1$, $R^2$, and $R^3$ are as described herein, $R^4$ is F, and $R^5$ is methyl. In an exemplary embodiment, the compound is of formula (I) or formula (II), or a salt, or a hydrate, or a solvate thereof, a, $R^1$, $R^2$, and $R^3$ are as described herein, $R^4$ is Cl, and $R^5$ is methyl. In an exemplary embodiment, the compound is of formula (I) or formula (II), or a salt, or a hydrate, or a solvate thereof, a, $R^1$, $R^2$, and $R^3$ are as described herein, $R^4$ is Br, and $R^5$ is methyl. In an exemplary embodiment, the compound is of formula (I) or formula (II), or a salt, or a hydrate, or a solvate thereof, a, $R^1$, $R^2$, $R^3$ are as described herein, $R^4$ is I, and $R^5$ is methyl.

In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is $C_3$-$C_6$ alkoxy. In an exemplary embodiment, the compound is of formula (I) or formula (II), or a salt, or a hydrate, or a solvate thereof, a, $R^1$, $R^2$, $R^3$ are as described herein, $R^4$ is halogen, and $R^5$ is methoxy. In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is ethoxy.

In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is halosubstituted $C_3$-$C_6$ alkoxy. In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is halosubstituted methoxy. In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is halosubstituted ethoxy.

In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is trifluorosubstituted $C_3$-$C_6$ alkoxy. In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is trifluoromethoxy. In an exemplary embodiment, the compound is of formula (I) or formula (II), or a salt, or a hydrate, or a solvate thereof, a, $R^1$, $R^2$, and $R^3$ are as described herein, $R^4$ is halogen, and $R^5$ is trifluorosubstituted ethoxy.

In an exemplary embodiment, the compound is of formula (I) or formula (II), or a salt, or a hydrate, or a solvate thereof, a, $R^1$, $R^2$, and $R^3$ are as described herein, $R^4$ is $C_3$-$C_6$ alkoxy, and $R^5$ is halogen. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is halogen. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is halogen.

In an exemplary embodiment, the compound is of formula (I) or formula (II), or a salt, or a hydrate, or a solvate thereof, a, $R^1$, $R^2$, and $R^3$ are as described herein, $R^4$ is halosubstituted $C_3$-$C_6$ alkoxy, and $R^5$ is halogen. In an exemplary embodiment, the compound is of formula (I) or formula (II), or a salt, or a hydrate, or a solvate thereof, a, $R^1$, $R^2$, and $R^3$ are as described herein, $R^4$ is halosubstituted methoxy, and $R^5$ is halogen. In an exemplary embodiment, the compound is of formula (I) or formula (II), or a salt, or a hydrate, or a solvate thereof, a, $R^1$, $R^2$, and $R^3$ are as described herein, $R^4$ is halosubstituted ethoxy, and $R^5$ is halogen.

In an exemplary embodiment, the compound is of formula (I) or formula (II), or a salt, or a hydrate, or a solvate thereof, a, $R^1$, $R^2$, and $R^3$ are as described herein, $R^4$ is trifluorosubstituted $C_3$-$C_6$ alkoxy, and $R^5$ is halogen. In an exemplary embodiment, the compound is of formula (I) or formula (II), or a salt, or a hydrate, or a solvate thereof, a, $R^1$, $R^2$, and $R^3$ are as described herein, $R^4$ is trifluoromethoxy, and $R^5$ is halogen. In an exemplary embodiment, the compound is of formula (I) or formula (II), or a salt, or a hydrate, or a solvate thereof, a, $R^1$, $R^2$, and $R^3$ are as described herein, $R^4$ is trifluorosubstituted ethoxy, and $R^5$ is halogen.

In an exemplary embodiment, the compound is of formula (I) or formula (II), or a salt, or a hydrate, or a solvate thereof, a, $R^1$, $R^2$, and $R^3$ are as described herein, $R^4$ is methyl, and $R^5$ is F. In an exemplary embodiment, the compound is of formula (I) or formula (II), or a salt, or a hydrate, or a solvate thereof, a, $R^1$, $R^2$, and $R^3$ are as described herein, $R^4$ is methyl, and $R^5$ is Cl. In an exemplary embodiment, the compound is of formula (I) or formula (II), or a salt, or a hydrate, or a solvate thereof, a, $R^1$, $R^2$, and $R^3$ are as described herein, $R^4$ is methyl, and $R^5$ is Br. In an exemplary embodiment, the compound is of formula (I) or formula (II), or a salt, or a hydrate, or a solvate thereof, a, $R^1$, $R^2$, and $R^3$ are as described herein, $R^4$ is methyl, and $R^5$ is I.

In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is F. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is Cl. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is Br. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is I. In an exemplary embodiment, the compound is of formula (I) or formula (II), or a salt, or a hydrate, or a solvate thereof, a, $R^1$, $R^2$, and $R^3$ are as described herein, $R^4$ is trifluoromethyl, and $R^5$ is F. In an exemplary embodiment, the compound is of formula (I) or formula (II), or a salt, or a hydrate, or a solvate thereof, a, $R^1$, $R^2$, and $R^3$ are as described herein, $R^4$ is trifluoromethyl, and $R^5$ is Cl. In an exemplary embodiment, the compound is of formula (I) or formula (II), or a salt, or a hydrate, or a solvate thereof, a, $R^1$, $R^2$, and $R^3$ are as described herein, $R^4$ is trifluoromethyl, and $R^5$ is Br. In an exemplary embodiment, the compound is of formula (I) or formula (II), or a salt, or a hydrate, or a solvate thereof, a, $R^1$, $R^2$, and $R^3$ are as described herein, $R^4$ is trifluoromethyl, and $R^5$ is I. In an exemplary embodiment, the compound is of formula (I) or formula (II), or a salt, or a hydrate, or a solvate thereof, a, $R^1$, $R^2$, and $R^3$ are as described herein, $R^4$ is trifluoromethoxy, and $R^5$ is F. In an exemplary embodiment, the compound is of formula (I) or formula (II), or a salt, or a hydrate, or a solvate thereof, a, $R^1$, $R^2$, and $R^3$ are as described herein, $R^4$ is trifluoromethoxy, and $R^5$ is Cl. In an exemplary embodiment, the compound is of formula (I) or formula (II), or a salt, or a hydrate, or a solvate thereof, a, $R^1$, $R^2$, and $R^3$ are as described herein, $R^4$ is trifluoromethoxy, and $R^5$ is Br. In an exemplary embodiment, the compound is of formula (I) or formula (II), or a salt, or a hydrate, or a solvate thereof, a, $R^1$, $R^2$, and $R^3$ are as described herein, $R^4$ is trifluoromethoxy, and $R^5$ is I. In an exemplary embodiment, the compound is of formula (I) or formula (II), or a salt, or a hydrate, or a solvate thereof, a, $R^1$, $R^2$, and $R^3$ are as described herein, $R^4$ is ethyl, and $R^5$ is F. In an exemplary embodiment, the compound is of formula (I) or formula (II), or a salt, or a hydrate, or a solvate thereof, a, $R^1$, $R^2$, and $R^3$ are as described herein, $R^4$ is ethyl, and $R^5$ is Cl. In an exemplary embodiment, the compound is of formula (I) or formula (II), or a salt, or a hydrate, or a solvate thereof, a, $R^1$, $R^2$, $R^3$ are as described herein, $R^4$ is ethyl, and $R^5$ is Br. In an exemplary embodiment, the compound is of formula (I) or formula (II), or a salt, or a hydrate, or a solvate thereof, a, $R^1$, $R^2$, and $R^3$ are as described herein, $R^4$ is ethyl, and $R^5$ is I. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is F. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is Cl. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is Br. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is I.

In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_6$ alkyl, and $R^5$ is $C_1$-$C_6$ alkyl. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkyl, and $R^5$ is $C_1$-$C_3$ alkyl. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_6$ alkyl, and $R^5$ is methyl. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkyl, and $R^5$ is methyl. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkyl, and $R^5$ is ethyl. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkyl, and $R^5$ is propyl or isopropyl. In an exemplary embodiment, the compound is of formula (I) or formula (II), or a salt, or a hydrate, or a solvate thereof, a, $R^1$, $R^2$, and $R^3$ are as described herein, $R^4$ is methyl, and $R^5$ is methyl. In an exemplary embodiment, the compound is of formula (I) or formula (II), or a salt, or a hydrate, or a solvate thereof, a, $R^1$, $R^2$, and $R^3$ are as described herein, $R^4$ is methyl, and $R^5$ is $C_1$-$C_6$ alkyl. In an exemplary embodiment, the compound is of formula (I) or formula (II), or a salt, or a hydrate, or a solvate thereof, a, $R^1$, $R^2$, and $R^3$ are as described herein, $R^4$ is methyl, and $R^5$ is $C_1$-$C_3$ alkyl. In an exemplary embodiment, the compound is of formula (I) or formula (II), or a salt, or a hydrate, or a solvate thereof, a, $R^1$, $R^2$, and $R^3$ are as described herein, $R^4$ is ethyl, and $R^5$ is $C_1$-$C_6$ alkyl. In an exemplary embodiment, the compound is of formula (I) or formula (II), or a salt, or a hydrate, or a solvate thereof, a, $R^1$, $R^2$, and $R^3$ are as described herein, $R^4$ is ethyl, and $R^5$ is $C_1$-$C_3$ alkyl.

In an exemplary embodiment, the compound is of formula (I) or formula (II), or a salt, or a hydrate, or a solvate thereof, a, $R^1$, $R^2$, and $R^3$ are as described herein, $R^4$ is halogen substituted $C_1$-$C_6$ alkyl, and $R^5$ is $C_3$-$C_6$ alkoxy. In an exemplary embodiment, the compound is of formula (I) or formula (II), or a salt, or a hydrate, or a solvate thereof, a, $R^1$, $R^2$, and $R^3$ are as described herein, $R^4$ is halogen substituted $C_1$-$C_6$ alkyl, and $R^5$ is methoxy. In an exemplary embodiment, the compound is of formula (I) or formula (II), or a salt, or a hydrate, or a solvate thereof, a, $R^1$, $R^2$, $R^3$ are as described herein, $R^4$ is halogen substituted $C_1$-$C_3$ alkyl, and $R^5$ is methoxy. In an exemplary embodiment, the compound is of formula (I) or formula (II), or a salt, or a hydrate, or a solvate thereof, a, $R^1$, $R^2$, and $R^3$ are as described herein, $R^4$ is halogen substituted $C_1$-$C_6$ alkyl, and $R^5$ is ethoxy. In an exemplary embodiment, the compound is of formula (I) or formula (II), or a salt, or a hydrate, or a solvate thereof, a, $R^1$, $R^2$, and $R^3$ are as described herein, $R^4$ is halogen substituted methyl, and $R^5$ is methoxy or ethoxy. In an exemplary embodiment, the compound is of formula (I) or formula (II), or a salt, or a hydrate, or a solvate thereof, a, $R^1$, $R^2$, and $R^3$ are as described herein, $R^4$ is trifluoromethyl or difluoromethyl, and $R^5$ is methoxy or ethoxy.

In an exemplary embodiment, the compound is of formula (I) or formula (II), or a salt, or a hydrate, or a solvate thereof, a, $R^1$, $R^2$, and $R^3$ are as described herein, $R^5$ is $C_3$-$C_6$ alkoxy, and $R^4$ is halosubstituted $C_4$-$C_6$ alkyl. In an exemplary embodiment, the compound is of formula (I) or formula (II), or a salt, or a hydrate, or a solvate thereof, a, $R^1$, $R^2$, and $R^3$ are as described herein, $R^5$ is $C_3$-$C_6$ alkoxy, and $R^4$ is halosubstituted $C_1$-$C_3$ alkyl. In an exemplary embodiment, the compound is of formula (I) or formula (II), or a salt, or a hydrate, or a solvate thereof, a, $R^1$, $R^2$, and $R^3$ are as described herein, $R^5$ is $C_3$-$C_6$ alkoxy, and $R^4$ is halosubstituted methyl. In an exemplary embodiment, the compound is of formula (I) or formula (II), or a salt, or a hydrate, or a solvate thereof, a, $R^1$, $R^2$, and $R^3$ are as described herein, $R^5$ is $C_3$-$C_6$ alkoxy, and $R^4$ is trifluoromethyl. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is halosubstituted $C_4$-$C_6$ alkyl. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is halosubstituted $C_1$-$C_3$ alkyl. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is halosubstituted methyl. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is trifluoromethyl. In an exemplary embodiment, the compound is of formula (I) or formula (II), or a salt, or a hydrate, or a solvate thereof, a, $R^1$, $R^2$, and $R^3$ are as described herein, $R^5$ is ethoxy, and $R^4$ is halosubstituted $C_4$-$C_6$ alkyl. In an exemplary embodiment, the compound is of formula (I) or formula (II), or a salt, or a hydrate, or a solvate thereof, a, $R^1$, $R^2$, and $R^3$ are as described herein, $R^5$ is ethoxy, and $R^4$ is halosubstituted $C_1$-$C_3$ alkyl. In an exemplary embodiment, the compound is of formula (I) or formula (II), or a salt, or a hydrate, or a solvate thereof, a, $R^1$, $R^2$, and $R^3$ are as described herein, $R^5$ is ethoxy, and $R^4$ is halosubstituted methyl. In an exemplary embodiment, the compound is of formula (I) or formula (II), or a salt, or a hydrate, or a solvate thereof, a, $R^1$, $R^2$, and $R^3$ are as described herein, $R^5$ is ethoxy, and $R^4$ is trifluoromethyl.

In an exemplary embodiment, the compound is of formula (I) or formula (II), or a salt, or a hydrate, or a solvate thereof, a, $R^1$, $R^2$, and $R^3$ are as described herein, $R^4$ is $C_3$-$C_6$ alkoxy, and $R^5$ is halogen substituted $C_1$-$C_6$ alkyl. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is halogen substituted $C_1$-$C_6$ alkyl. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is halogen substituted $C_1$-$C_3$ alkyl. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is halogen substituted $C_1$-$C_3$ alkyl. In an exemplary embodiment, the compound is of formula (I) or formula (II), or a salt, or a hydrate, or a solvate thereof, a, $R^1$, $R^2$, and $R^3$ are as described herein, $R^4$ is methoxy or ethoxy, and $R^5$ is halogen substituted methyl. In an exemplary embodiment, the compound is of formula (I) or formula (II), or a salt, or a hydrate, or a solvate thereof, a, $R^1$, $R^2$, and $R^3$ are as described herein, $R^4$ is methoxy or ethoxy, and $R^5$ is trifluoromethyl or difluoromethyl.

In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_6$ alkoxy, and $R^5$ is halosubstituted $C_1$-$C_6$ alkoxy. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkoxy, and $R^5$ is halosubstituted $C_1$-$C_3$ alkoxy. In an exemplary embodiment, the compound is of formula (I) or formula (II), or a salt, or a hydrate, or a solvate thereof, a, $R^1$, $R^2$, and $R^3$ are as described herein, $R^4$ is $C_3$-$C_6$ alkoxy, and $R^5$ is halosubstituted $C_4$-$C_6$ alkoxy. In an exemplary embodiment, the compound is of formula (I) or formula (II), or a salt, or a hydrate, or a solvate thereof, a, $R^1$, $R^2$, and $R^3$ are as described herein, $R^4$ is $C_3$-$C_6$ alkoxy, and $R^5$ is halosubstituted $C_1$-$C_3$ alkoxy. In an exemplary embodiment, the compound is of formula (I) or formula (II), or a salt, or a hydrate, or a solvate thereof, a, $R^1$, $R^2$, $R^3$ are as described herein, $R^4$ is $C_3$-$C_6$ alkoxy, and $R^5$ is halosubstituted methoxy. In an exemplary embodiment, the compound is of formula (I) or formula (II), or a salt, or a hydrate, or a solvate thereof, a, $R^1$, $R^2$, and $R^3$ are as described herein, $R^4$ is $C_3$-$C_6$ alkoxy, and $R^5$ is trifluoromethoxy. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is halosubstituted $C_4$-$C_6$ methoxy. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is halosubstituted $C_1$-$C_3$ alkoxy. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is halosubstituted methoxy. In an exemplary embodiment, the compound is of formula (I) or formula (II), or a salt, or a solvate thereof, a, $R^1$, $R^2$, and $R^3$ are as described herein, $R^4$ is methoxy, and $R^5$ is trifluoromethoxy. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is difluoromethoxy. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is halosubstituted $C_4$-$C_6$ alkoxy. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is halosubstituted $C_1$-$C_3$ alkoxy. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is halosubstituted methoxy. In an exemplary embodiment, the compound is of formula (I) or formula (II), or a salt, or a hydrate, or a solvate thereof, a, $R^1$, $R^2$, and $R^3$ are as described herein, $R^4$ is ethoxy, and $R^5$ is trifluoromethoxy.

In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_6$ alkoxy, and $R^4$ is halosubstituted $C_1$-$C_6$ alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_3$ alkoxy, and $R^4$ is halosubstituted $C_1$-$C_3$ alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_3$-$C_6$ alkoxy, and $R^4$ is halosubstituted $C_4$-$C_6$ alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_3$-$C_6$ alkoxy, and $R^4$ is halosubstituted $C_1$-$C_3$ alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_3$-$C_6$ alkoxy, and $R^4$ is halosubstituted methoxy. In an exemplary embodiment, the compound is of formula (I) or formula (II), or a salt, or a hydrate, or a solvate thereof, a, $R^1$, $R^2$, and $R^3$ are as described herein, $R^5$ is $C_3$-$C_6$ alkoxy, and $R^4$ is trifluoromethoxy. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is halosubstituted $C_4$-$C_6$ methoxy. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is halosubstituted $C_1$-$C_3$ alkoxy. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is halosubstituted methoxy. In an exemplary embodiment, the compound is of formula (I) or formula (II), or a salt, or a hydrate, or a solvate thereof, a, $R^1$, $R^2$, $R^3$ are as described herein, $R^5$ is methoxy, and $R^4$ is trifluoromethoxy. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is difluoromethoxy. In an exemplary embodiment, the compound is of formula (I) or formula (II), or a salt, or a hydrate, or a solvate thereof, a, $R^1$, $R^2$, and $R^3$ are as described herein, $R^5$ is ethoxy, and $R^4$ is halosubstituted $C_4$-$C_6$ alkoxy. In an exemplary embodiment, the compound is of formula (I) or formula (II), or a salt, or a hydrate, or a solvate thereof, a, $R^1$, $R^2$, and $R^3$ are as described herein, $R^5$ is ethoxy, and $R^4$ is halosubstituted $C_1$-$C_3$ alkoxy. In an exemplary embodiment, the compound is of formula (I) or formula (II), or a salt, or a hydrate, or a solvate thereof, a, $R^1$, $R^2$, and $R^3$ are as described herein, $R^5$ is ethoxy, and $R^4$ is halosubstituted methoxy. In an exemplary embodiment, the compound is of formula (I) or formula (II), or a salt, or a hydrate, or a solvate thereof, a, $R^1$, $R^2$, and $R^3$ are as described herein, $R^5$ is ethoxy, and $R^4$ is trifluoromethoxy.

In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_6$ alkoxy, and $R^5$ is $C_3$-$C_7$ cycloalkyl alkoxy. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkoxy, and $R^5$ is $C_3$-$C_7$ cycloalkyl alkoxy. In an exemplary embodiment, the compound is of formula (I) or formula (II), or a salt, or a hydrate, or a solvate thereof, a, $R^1$, $R^2$, and $R^3$ are as described herein, $R^4$ is $C_3$-$C_6$ alkoxy, and $R^5$ is $C_3$-$C_7$ cycloalkyl alkoxy. In an exemplary embodiment, the compound is of formula (I) or formula (II), or a salt, or a hydrate, or a solvate thereof, a, $R^1$, $R^2$, and $R^3$ are as described herein, $R^4$ is $C_4$-$C_6$ alkoxy, and $R^5$ is $C_3$-$C_7$ cycloalkyl methoxy. In an exemplary embodiment, the compound is of formula (I) or formula (II), or a salt, or a hydrate, or a solvate thereof, a, $R^1$, $R^2$, $R^3$ are as described herein, $R^4$ is $C_2$-$C_3$ alkoxy, and $R^5$ is $C_3$-$C_7$ cycloalkyl methoxy. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is $C_3$-$C_7$ cycloalkyl methoxy. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkoxy, and $R^5$ is cyclopropyl alkoxy. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkoxy, and $R^5$ is cyclopropyl methoxy. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is cyclopropyl methoxy. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkoxy, and $R^5$ is cyclobutyl alkoxy. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkoxy, and $R^5$ is cyclobutyl methoxy. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is cyclobutyl methoxy. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkoxy, and $R^5$ is cyclopentyl alkoxy. In an exemplary embodiment, the compound is of formula (I) or formula (II), or a salt, or a hydrate, or a solvate thereof, a, $R^1$, $R^2$, and $R^3$ are as described herein, $R^4$ is $C_1$-$C_3$ alkoxy, and $R^5$ is cyclopentyl methoxy. In an exemplary embodiment, the compound is of formula (I) or formula (II), or a salt, or a hydrate, or a solvate thereof, a, $R^1$, $R^2$, and $R^3$ are as described herein, $R^4$ is methoxy, and $R^5$ is cyclopentyl methoxy.

In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_6$ alkoxy, and $R^4$ is $C_3$-$C_7$ cycloalkyl alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_3$ alkoxy, and $R^4$ is $C_3$-$C_7$ cycloalkyl alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_3$-$C_6$ alkoxy, and $R^4$ is $C_3$-$C_7$ cycloalkyl alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_4$-$C_6$ alkoxy, and $R^4$ is $C_3$-$C_7$ cycloalkyl methoxy. In an exemplary embodiment, the compound is of formula (I) or formula (II), or a salt, or a hydrate, or a solvate thereof, a, $R^1$, $R^2$, $R^3$ are as described herein, $R^5$ is $C_2$-$C_3$ alkoxy, and $R^4$ is $C_3$-$C_7$ cycloalkyl methoxy. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is $C_3$-$C_7$ cycloalkyl methoxy. In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_3$ alkoxy, and $R^4$ is cyclopropyl alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_3$ alkoxy, and $R^4$ is cyclopropyl methoxy. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is cyclopropyl methoxy. In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_3$ alkoxy, and $R^4$ is cyclobutyl alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_3$ alkoxy, and $R^4$ is cyclobutyl methoxy. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is cyclobutyl methoxy. In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_3$ alkoxy, and $R^4$ is cyclopentyl alkoxy. In an exemplary embodiment, the compound is of formula (I) or formula (II), or a salt, or a hydrate, or a solvate thereof, a, $R^1$, $R^2$, and $R^3$ are as described herein, $R^5$ is $C_1$-$C_3$ alkoxy, and $R^4$ is cyclopentyl methoxy. In an exemplary embodiment, the compound is of formula (I) or formula (II), or a salt, or a hydrate, or a solvate thereof, a, $R^1$, $R^2$, and $R^3$ are as described herein, $R^5$ is methoxy, and $R^4$ is cyclopentyl methoxy.

In an exemplary embodiment, the compound is of formula (I) or formula (II), or a salt, or a hydrate, or a solvate thereof, a, $R^1$, $R^2$, and $R^4$ are as described herein, $R^5$ is F, and $R^3$ is H. In an exemplary embodiment, the compound is of formula (I) or formula (II), or a salt, or a hydrate, or a solvate thereof, a, $R^1$, $R^2$, and $R^4$ are as described herein, $R^5$ is Cl, and $R^3$ is H. In an exemplary embodiment, the compound is of formula (I) or formula (II), or a salt, or a hydrate, or a solvate thereof, a, $R^1$, $R^2$, and $R^4$ are as described herein, $R^5$ is Br, and $R^3$ is H. In an exemplary embodiment, the compound is of formula (I) or formula (II), or a salt, or a hydrate, or a solvate thereof, a, $R^1$, $R^2$, and $R^4$ are as described herein, $R^5$ is I, and $R^3$ is H.

In an exemplary embodiment, the compound is of formula (I) or formula (II), or a salt, or a hydrate, or a solvate thereof, a, $R^1$, $R^2$, and $R^5$ are as described herein, $R^4$ is methyl, and $R^3$ is H. In an exemplary embodiment, the compound is of formula (I) or formula (II), or a salt, or a hydrate, or a solvate thereof, a, $R^1$, $R^2$, and $R^5$ are as described herein, $R^4$ is methoxy, and $R^3$ is H. In an exemplary embodiment, the compound is of formula (I) or formula (II), or a salt, or a hydrate, or a solvate thereof, a, $R^1$, $R^2$, and $R^5$ are as described herein, $R^4$ is trifluoromethyl, and $R^3$ is H. In an exemplary embodiment, the compound is of formula (I) or formula (II), or a salt, or a hydrate, or a solvate thereof, a, $R^1$, $R^2$, and $R^5$ are as described herein, $R^4$ is trifluoromethoxy, and $R^3$ is H. In an exemplary embodiment, the compound is of formula (I) or formula (II), or a salt, or a hydrate, or a solvate thereof, a, $R^1$, $R^2$, and $R^5$ are as described herein, $R^4$ is ethyl, and $R^3$ is H. In an exemplary embodiment, the compound is of formula (I) or formula (II), or a salt, or a hydrate, or a solvate thereof, a, $R^1$, $R^2$, and $R^5$ are as described herein, $R^4$ is ethoxy, and $R^3$ is H.

In an exemplary embodiment, the compound is of formula (I) or formula (II), or a salt, or a hydrate, or a solvate thereof, a, $R^1$, $R^3$, and $R^4$ are as described herein, $R^5$ is F, and $R^2$ is methyl. In an exemplary embodiment, the compound is of formula (I) or formula (II), or a salt, or a hydrate, or a solvate thereof, a, $R^1$, $R^3$, and $R^4$ are as described herein, $R^5$ is Cl, and $R^2$ is methyl. In an exemplary embodiment, the compound is of formula (I) or formula (II), or a salt, or a hydrate, or a solvate thereof, a, $R^1$, $R^3$, and $R^4$ are as described herein, $R^5$ is Br, and $R^2$ is methyl. In an exemplary embodiment, the compound is of formula (I) or formula (II), or a salt, or a hydrate, or a solvate thereof, a, $R^1$, $R^3$, and $R^4$ are as described herein, $R^5$ is I, and $R^2$ is methyl.

In an exemplary embodiment, the compound is of formula (I) or formula (II), or a salt, or a hydrate, or a solvate thereof, a, $R^1$, $R^3$, and $R^5$ are as described herein, $R^4$ is methyl, and $R^2$ is methyl. In an exemplary embodiment, the compound is of formula (I) or formula (II), or a salt, or a hydrate, or a solvate thereof, a, $R^1$, $R^3$, and $R^5$ are as described herein, $R^4$ is methoxy, and $R^2$ is methyl. In an exemplary embodiment, the compound is of formula (I) or formula (II), or a salt, or a hydrate, or a solvate thereof, a, $R^2$, $R^3$, and $R^5$ are as described herein, $R^4$ is trifluoromethyl, and $R^2$ is methyl. In an exemplary embodiment, the compound is of formula (I) or formula (II), or a salt, or a hydrate, or a solvate thereof, a, $R^1$, $R^3$, and $R^5$ are as described herein, $R^4$ is trifluoromethoxy, and $R^2$ is methyl. In an exemplary embodiment, the compound is of formula (I) or formula (II), or a salt, or a hydrate, or a solvate thereof, a, $R^1$, $R^3$, and $R^5$ are as described herein, $R^4$ is ethyl, and $R^2$ is methyl. In an exemplary embodiment, the compound is of formula (I) or formula (II), or a salt, or a hydrate, or a solvate thereof, a, $R^1$, $R^3$, and $R^5$ are as described herein, $R^4$ is ethoxy, and $R^2$ is methyl.

In an exemplary embodiment, the compound is of formula (I) or formula (II), or a salt, or a hydrate, or a solvate thereof, a, R', $R^4$, and $R^5$ are as described herein, $R^2$ is methyl, and $R^3$ is H.

In an exemplary embodiment, the compound is of formula (I) or formula (II), or a salt, or a hydrate, or a solvate thereof, a, $R^2$, $R^3$, and $R^4$ are as described herein, $R^5$ is F, and $R^1$ is t-butyl. In an exemplary embodiment, the compound is of formula (I) or formula (II), or a salt, or a hydrate, or a solvate thereof, a, $R^2$, $R^3$, and $R^4$ are as described herein, $R^5$ is Cl, and $R^1$ is t-butyl. In an exemplary embodiment, the compound is of formula (I) or formula (II), or a salt, or a hydrate, or a solvate thereof, a, $R^2$, $R^3$, and $R^4$ are as described herein, $R^5$ is Br, and $R^1$ is t-butyl. In an exemplary embodiment, the compound is of formula (I) or formula (II), or a salt, or a hydrate, or a solvate thereof, a, $R^2$, $R^3$, and $R^4$ are as described herein, $R^5$ is I, and $R^1$ is t-butyl. In an exemplary embodiment, the compound is of formula (I) or formula (II), or a salt, or a hydrate, or a solvate thereof, a, $R^2$, $R^3$, and $R^4$ are as described herein, $R^5$ is F, and $R^1$ is cyclopropyl. In an exemplary embodiment, the compound is of formula (I) or formula (II), or a salt, or a hydrate, or a solvate thereof, a, $R^2$, $R^3$, and $R^4$ are as described herein, $R^5$ is Cl, and $R^1$ is cyclopropyl. In an exemplary embodiment, the compound is of formula (I) or formula (II), or a salt, or a hydrate, or a solvate thereof, a, $R^2$, $R^3$, and $R^4$ are as described herein, $R^5$ is Br, and $R^1$ is cyclopropyl. In an exemplary embodiment, the compound is of formula (I) or formula (II), or a salt, or a hydrate, or a solvate thereof, a, $R^2$, $R^3$, and $R^4$ are as described herein, $R^5$ is I, and $R^1$ is cyclopropyl. In an exemplary embodiment, the compound is of formula (I) or formula (II), or a salt, or a hydrate, or a solvate thereof, a, $R^2$, $R^3$, and $R^4$ are as described herein, $R^5$ is F, and $R^1$ is isopropyl. In an exemplary embodiment, the compound is of formula (I) or formula (II), or a salt, or a hydrate, or a solvate thereof, a, $R^2$, $R^3$, and $R^4$ are as described herein, $R^5$ is Cl, and $R^1$ is isopropyl. In an exemplary embodiment, the compound is of formula (I) or formula (II), or a salt, or a hydrate, or a solvate thereof, a, $R^2$, $R^3$, and $R^4$ are as described herein, $R^5$ is Br, and $R^1$ is isopropyl. In an exemplary embodiment, the compound is of formula (I) or formula (II), or a salt, or a hydrate, or a solvate thereof, a, $R^2$, $R^3$, and $R^4$ are as described herein, $R^5$ is I, and $R^1$ is isopropyl.

In an exemplary embodiment, the compound is of formula (I) or formula (II), or a salt, or a hydrate, or a solvate thereof, a, $R^2$, $R^3$, and $R^5$ are as described herein, $R^4$ is methyl, and $R^1$ is t-butyl. In an exemplary embodiment, the compound is of formula (I) or formula (II), or a salt, or a hydrate, or a solvate thereof, a, $R^2$, $R^3$, and $R^5$ are as described herein, $R^4$ is methoxy, and $R^1$ is t-butyl. In an exemplary embodiment, the compound is of formula (I) or formula (II), or a salt, or a hydrate, or a solvate thereof, a, $R^2$, $R^3$, and $R^5$ are as described herein, $R^4$ is trifluoromethyl, and $R^1$ is t-butyl. In an exemplary embodiment, the compound is of formula (I) or formula (II), or a salt, or a hydrate, or a solvate thereof, a, $R^2$, $R^3$, and $R^5$ are as described herein, $R^4$ is trifluoromethoxy, and $R^1$ is t-butyl. In an exemplary embodiment, the compound is of formula (I) or formula (II), or a salt, or a hydrate, or a solvate thereof, a, $R^2$, $R^3$, and $R^5$ are as described herein, $R^4$ is ethyl, and $R^1$ is t-butyl. In an exemplary embodiment, the compound is of formula (I) or formula (II), or a salt, or a hydrate, or a solvate thereof, a, $R^2$, $R^3$, and $R^5$ are as described herein, $R^4$ is ethoxy, and $R^1$ is t-butyl. In an exemplary embodiment, the compound is of formula (I) or formula (II), or a salt, or a hydrate, or a solvate thereof, a, $R^2$, $R^3$, and $R^5$ are as described herein, $R^4$ is methyl, and $R^1$ is cyclopropyl. In an exemplary embodiment, the compound is of formula (I) or formula (II), or a salt, or a hydrate, or a solvate thereof, a, $R^2$, $R^3$, and $R^5$ are as described herein, $R^4$ is methoxy, and $R^1$ is cyclopropyl. In an exemplary embodiment, the compound is of formula (I) or formula (II), or a salt, or a hydrate, or a solvate thereof, a, $R^2$, $R^3$, and $R^5$ are as described herein, $R^4$ is trifluoromethyl, and $R^1$ is cyclopropyl. In an exemplary embodiment, the compound is of formula (I) or formula (II), or a salt, or a hydrate, or a solvate thereof, a, $R^2$, $R^3$, and $R^5$ are as described herein, $R^4$ is trifluoromethoxy, and $R^1$ is cyclopropyl. In an exemplary embodiment, the compound is of formula (I) or formula (II), or a salt, or a hydrate, or a solvate thereof, a, $R^2$, $R^3$, and $R^5$ are as described herein, $R^4$ is ethyl, and $R^1$ is cyclopropyl. In an exemplary embodiment, the compound is of formula (I) or formula (II), or a salt, or a hydrate, or a solvate thereof, a, $R^2$, $R^3$, and $R^5$ are as described herein, $R^4$ is ethoxy, and $R^1$ is cyclopropyl. In an exemplary embodiment, the compound is of formula (I) or formula (II), or a salt, or a hydrate, or a solvate thereof, a, $R^2$, $R^3$, and $R^5$ are as described herein, $R^4$ is methyl, and $R^1$ is isopropyl. In an exemplary embodiment, the compound is of formula (I) or formula (II), or a salt, or a hydrate, or a solvate thereof, a, $R^2$, $R^3$, and $R^5$ are as described herein, $R^4$ is methoxy, and $R^1$ is isopropyl. In an exemplary embodiment, the compound is of formula (I) or formula (II), or a salt, or a hydrate, or a solvate thereof, a, $R^2$, $R^3$, and $R^5$ are as described herein, $R^4$ is trifluoromethyl, and $R^1$ is isopropyl. In an exemplary embodiment, the compound is of formula (I) or formula (II), or a salt, or a hydrate, or a solvate thereof, a, $R^2$, $R^3$, and $R^5$ are as described herein, $R^4$ is trifluoromethoxy, and $R^1$ is isopropyl. In an exemplary embodiment, the compound is of formula (I) or formula (II), or a salt, or a hydrate, or a solvate thereof, a, $R^2$, $R^3$, and $R^5$ are as described herein, $R^4$ is ethyl, and $R^1$ is isopropyl. In an exemplary embodiment, the compound is of formula (I) or formula (II), or a salt, or a hydrate, or a solvate thereof, a, $R^2$, $R^3$, and $R^5$ are as described herein, $R^4$ is ethoxy, and $R^1$ is isopropyl.

In an exemplary embodiment, the compound is of formula (I) or formula (II), or a salt, or a hydrate, or a solvate thereof, a, $R^2$, $R^4$, and $R^5$ are as described herein, $R^3$ is H, and $R^1$ is t-butyl. In an exemplary embodiment, the compound is of formula (I) or formula (II), or a salt, or a hydrate, or a solvate thereof, a, $R^2$, $R^4$, and $R^5$ are as described herein, $R^3$ is H, and $R^1$ is cyclopropyl. In an exemplary embodiment, the compound is of formula (I) or formula (II), or a salt, or a hydrate, or a solvate thereof, a, $R^2$, $R^4$, and $R^5$ are as described herein, $R^3$ is H, and $R^1$ is isopropyl.

In an exemplary embodiment, the compound is of formula (I) or formula (II), or a salt, or a hydrate, or a solvate thereof, a, $R^3$, $R^4$, and $R^5$ are as described herein, $R^2$ is methyl, and $R^1$ is t-butyl. In an exemplary embodiment, the compound is of formula (I) or formula (II), or a salt, or a hydrate, or a solvate thereof, a, $R^3$, $R^4$, and $R^5$ are as described herein, $R^2$ is methyl, and $R^1$ is cyclopropyl. In an exemplary embodiment, the compound is of formula (I) or formula (II), or a salt, or a hydrate, or a solvate thereof, a, $R^3$, $R^4$, and $R^5$ are as described herein, $R^2$ is methyl, and $R^1$ is isopropyl.

In an exemplary embodiment, the compound is of formula (I) or formula (II), or a salt, or a hydrate, or a solvate thereof, $R^2$, $R^3$, $R^4$, and $R^5$ are as described herein, a is 1, and $R^1$ is t-butyl. In an exemplary embodiment, the compound is of formula (I) or formula (II), or a salt, or a hydrate, or a solvate thereof, $R^2$, $R^3$, $R^4$, and $R^5$ are as described herein, a is 1, and $R^1$ is cyclopropyl. In an exemplary embodiment, the compound is of formula (I) or formula (II), or a salt, or a hydrate, or a solvate thereof, $R^2$, $R^3$, $R^4$, and $R^5$ are as described herein, a is 1, and $R^1$ is isopropyl.

In an exemplary embodiment, the compound is of formula (I) or formula (II), or a salt, or a hydrate, or a solvate thereof, $R^1$, $R^3$, $R^4$, and $R^5$ are as described herein, a is 1, and $R^2$ is methyl.

In an exemplary embodiment, the compound is of formula (III) or formula (IV) or formula (V), or a salt, or a hydrate, or a solvate thereof, $R^1$, $R^3$, $R^4$, $R^5$, and $R^6$ are as described herein, a is 1, and $R^2$ is methyl.

In an exemplary embodiment, the compound is of formula (I) or formula (II), or a salt, or a hydrate, or a solvate thereof, $R^1$, $R^2$, $R^4$, and $R^5$ are as described herein, a is 1, and $R^3$ is H.

In an exemplary embodiment, the compound is of formula (III) or formula (IV) or formula (V), or a salt, or a hydrate, or a solvate thereof, $R^1$, $R^3$, $R^4$, $R^5$, and $R^6$ are as described herein, a is 1, and $R^3$ is H.

In an exemplary embodiment, the compound is of formula (I) or formula (II), or a salt, or a hydrate, or a solvate thereof, $R^1$, $R^2$, $R^3$, and $R^5$ are as described herein, a is 1, and $R^4$ is methyl. In an exemplary embodiment, the compound is of formula (I) or formula (II), or a salt, or a hydrate, or a solvate thereof, $R^1$, $R^2$, $R^3$, and $R^5$ are as described herein, a is 1, and $R^4$ is methoxy. In an exemplary embodiment, the compound is of formula (I) or formula (II), or a salt, or a hydrate, or a solvate thereof, $R^1$, $R^2$, $R^3$, and $R^5$ are as described herein, a is 1, and $R^4$ is trifluoromethyl. In an exemplary embodiment, the compound is of formula (I) or formula (II), or a salt, or a hydrate, or a solvate thereof, $R^1$, $R^2$, $R^3$, and $R^5$ are as described herein, a is 1, and $R^4$ is trifluoromethoxy. In an exemplary embodiment, the compound is of formula (I) or formula (II), or a salt, or a hydrate, or a solvate thereof, $R^1$, $R^2$, $R^3$, and $R^5$ are as described herein, a is 1, and $R^4$ is ethyl. In an exemplary embodiment, the compound is of formula (I) or formula (II), or a salt, or a hydrate, or a solvate thereof, $R^1$, $R^2$, $R^3$, and $R^5$ are as described herein, a is 1, and $R^4$ is ethoxy.

In an exemplary embodiment, the compound is of formula (I) or formula (II), or a salt, or a hydrate, or a solvate thereof, $R^1$, $R^2$, $R^3$, and $R^4$ are as described herein, a is 1, and $R^5$ is F. In an exemplary embodiment, the compound is of formula (I) or formula (II), or a salt, or a hydrate, or a solvate thereof, $R^1$, $R^2$, $R^3$, and $R^4$ are as described herein, a is 1, and $R^5$ is Cl. In an exemplary embodiment, the compound is of formula (I) or formula (II), or a salt, or a hydrate, or a solvate thereof, $R^1$, $R^2$, $R^3$, and $R^4$ are as described herein, a is 1, and $R^5$ is Br. In an exemplary embodiment, the compound is of formula (I) or formula (II), or a salt, or a hydrate, or a solvate thereof, $R^1$, $R^2$, $R^3$, and $R^4$ are as described herein, a is 1, and $R^5$ is I.

In an exemplary embodiment, the compound is of formula (I) or formula (II), or a salt, or a hydrate, or a solvate thereof, $R^3$, $R^4$, and $R^5$ are as described herein, a is 1, $R^1$ is t-butyl, and $R^2$ is methyl. In an exemplary embodiment, the compound is of formula (I) or formula (II), or a salt, or a hydrate, or a solvate thereof, $R^3$, $R^4$, and $R^5$ are as described herein, a is 1, $R^1$ is cyclopropyl, and $R^2$ is methyl. In an exemplary embodiment, the compound is of formula (I) or formula (II), or a salt, or a hydrate, or a solvate thereof, $R^3$, $R^4$, and $R^5$ are as described herein, a is 1, $R^1$ is isopropyl, and $R^2$ is methyl.

In an exemplary embodiment, the compound is of formula (I) or formula (II), or a salt, or a hydrate, or a solvate thereof, $R^2$, $R^4$, and $R^5$ are as described herein, a is 1, $R^1$ is t-butyl, and $R^3$ is H. In an exemplary embodiment, the compound is of formula (I) or formula (II), or a salt, or a hydrate, or a solvate thereof, $R^2$, $R^4$, and $R^5$ are as described herein, a is 1, $R^1$ is cyclopropyl, and $R^3$ is H. In an exemplary embodiment, the compound is of formula (I) or formula (II), or a salt, or a hydrate, or a solvate thereof, $R^2$, $R^4$, and $R^5$ are as described herein, a is 1, $R^1$ is isopropyl, and $R^3$ is H.

In an exemplary embodiment, the compound is of formula (III) or formula (IV), or a salt, or a hydrate, or a solvate thereof, $R^3$, $R^4$, $R^5$ and $R^6$ are as described herein, a is 1, $R^1$ is t-butyl, and $R^2$ is methyl. In an exemplary embodiment, the compound is of formula (III) or formula (IV), or a salt, or a hydrate, or a solvate thereof, $R^3$, $R^4$, $R^5$ and $R^6$ are as described herein, a is 1, $R^1$ is cyclopropyl, and $R^2$ is methyl. In an exemplary embodiment, the compound is of formula (III) or formula (IV), or a salt, or a hydrate, or a solvate thereof, $R^3$, $R^4$, $R^5$ and $R^6$ are as described herein, a is 1, $R^1$ is isopropyl, and $R^2$ is methyl.

In an exemplary embodiment, the compound is of formula (III) or formula (IV) or formula (V), or a salt, or a hydrate, or a solvate thereof, $R^2$, $R^4$, $R^5$ and $R^6$ are are as described herein, a is 1, $R^1$ is t-butyl, and $R^3$ is H. In an exemplary embodiment, the compound is of formula (III) or formula (IV) or formula (V), or a salt, or a hydrate, or a solvate thereof, $R^2$, $R^4$, $R^5$ and $R^6$ are are as described herein, a is 1, $R^1$ is cyclopropyl, and $R^3$ is H. In an exemplary embodiment, the compound is of formula (III) or formula (IV) or formula (V), $R^2$, $R^4$, $R^5$ and $R^6$ are are as described herein, a is 1, $R^1$ is isopropyl, and $R^3$ is H.

In an exemplary embodiment, the compound is of formula (I) or formula (II), or a salt, or a hydrate, or a solvate thereof, $R^1$, $R^4$, and $R^5$ are as described herein, a is 1, $R^2$ is methyl, and $R^3$ is H.

In an exemplary embodiment, the compound is of formula (III) or formula (IV), or a salt, or a hydrate, or a solvate thereof, $R^1$, $R^4$, $R^5$ and $R^6$ are as described herein, a is 1, $R^2$ is methyl, and $R^3$ is H.

In an exemplary embodiment, the compound is of formula (I) or formula (II), or a salt, or a hydrate, or a solvate thereof, $R^1$, $R^3$, and $R^5$ are as described herein, a is 1, $R^2$ is methyl, and $R^4$ is methyl. In an exemplary embodiment, the compound is of formula (I) or formula (II), or a salt, or a hydrate, or a solvate thereof, $R^1$, $R^3$, and $R^5$ are as described herein, a is 1, $R^2$ is methyl, and $R^5$ is methoxy. In an exemplary embodiment, the compound is of formula (I) or formula (II), or a salt, or a hydrate, or a solvate thereof, $R^1$, $R^3$, and $R^5$ are as described herein, a is 1, $R^2$ is methyl, and $R^5$ is trifluoromethyl. In an exemplary embodiment, the compound is of formula (I) or formula (II), or a salt, or a hydrate, or a solvate thereof, $R^1$, $R^3$, and $R^5$ are as described herein, a is 1, $R^2$ is methyl, and $R^5$ is trifluoromethoxy. In an exemplary embodiment, the compound is of formula (I) or formula (II), or a salt, or a hydrate, or a solvate thereof, $R^1$, $R^3$, and $R^5$ are as described herein, a is 1, $R^2$ is methyl, and $R^5$ is ethyl. In an exemplary embodiment, the compound is of formula (I) or formula (II), or a salt, or a hydrate, or a solvate thereof, $R^1$, $R^3$, and $R^5$ are as described herein, a is 1, $R^2$ is methyl, and $R^5$ is ethoxy.

In an exemplary embodiment, the compound is of formula (I) or formula (II), or a salt, or a hydrate, or a solvate thereof, $R^1$, $R^3$, and $R^4$ are as described herein, a is 1, $R^2$ is methyl, and $R^5$ is F. In an exemplary embodiment, the compound is of formula (I) or formula (II), or a salt, or a hydrate, or a solvate thereof, $R^1$, $R^3$, and $R^4$ are as described herein, a is 1, $R^2$ is methyl, and $R^5$ is Cl. In an exemplary embodiment, the compound is of formula (I) or formula (II), or a salt, or a hydrate, or a solvate thereof, $R^1$, $R^3$, and $R^4$ are as described herein, a is 1, $R^2$ is methyl, and $R^5$ is Br. In an exemplary embodiment, the compound is of formula (I) or formula (II), or a salt, or a hydrate, or a solvate thereof, $R^1$, $R^3$, and $R^4$ are as described herein, a is 1, $R^2$ is methyl, and $R^5$ is I.

In an exemplary embodiment, the compound is of formula (I) or formula (II), or a salt, or a hydrate, or a solvate thereof, $R^1$, $R^2$, and $R^5$ are as described herein, a is 1, $R^3$ is H, and $R^4$ is methyl. In an exemplary embodiment, the compound is of formula (I) or formula (II), or a salt, or a hydrate, or a solvate thereof, $R^1$, $R^2$, and $R^5$ are as described herein, a is 1, $R^3$ is H, and $R^5$ is methoxy. In an exemplary embodiment, the compound is of formula (I) or formula (II), or a salt, or a hydrate, or a solvate thereof, $R^1$, $R^2$, and $R^5$ are as described herein, a is 1, $R^3$ is H, and $R^5$ is trifluoromethyl. In an exemplary embodiment, the compound is of formula (I) or formula (II), or a salt, or a hydrate, or a solvate thereof, $R^1$, $R^2$, and $R^5$ are as described herein, a is 1, $R^3$ is H, and $R^5$ is trifluoromethoxy. In an exemplary embodiment, the compound is of formula (I) or formula (II), or a salt, or a hydrate, or a solvate thereof, $R^1$, $R^2$, and $R^5$ are as described herein, a is 1, $R^3$ is H, and $R^5$ is ethyl. In an exemplary embodiment, the compound is of formula (I) or formula (II), or a salt, or a hydrate, or a solvate thereof, $R^1$, $R^2$, and $R^5$ are as described herein, a is 1, $R^3$ is H, and $R^5$ is ethoxy.

In an exemplary embodiment, the compound is of formula (I) or formula (II), or a salt, or a hydrate, or a solvate thereof, $R^1$, $R^2$, and $R^4$ are as described herein, a is 1, $R^3$ is H, and $R^5$ is F. In an exemplary embodiment, the compound is of formula (I) or formula (II), or a salt, or a hydrate, or a solvate thereof, $R^1$, $R^2$, and $R^4$ are as described herein, a is 1, $R^3$ is H, and $R^5$ is Cl. In an exemplary embodiment, the compound is of formula (I) or formula (II), or a salt, or a hydrate, or a solvate thereof, $R^1$, $R^2$, and $R^4$ are as described herein, a is 1, $R^3$ is H, and $R^5$ is Br. In an exemplary embodiment, the compound is of formula (I) or formula (II), or a salt, or a hydrate, or a solvate thereof, $R^1$, $R^2$, and $R^4$ are as described herein, a is 1, $R^3$ is H, and $R^5$ is I.

In an exemplary embodiment, the compound is of formula (I) or formula (II), or a salt, or a hydrate, or a solvate thereof, a, $R^4$, and $R^5$ are as described herein, $R^1$ is t-butyl, $R^2$ is methyl, and $R^3$ is H. In an exemplary embodiment, the compound is of formula (I) or formula (II), or a salt, or a hydrate, or a solvate thereof, a, $R^4$, and $R^5$ are as described herein, $R^1$ is cyclopropyl, $R^2$ is methyl, and $R^3$ is H. In an exemplary embodiment, the compound is of formula (I) or formula (II), or a salt, or a hydrate, or a solvate thereof, a, $R^4$, and $R^5$ are as described herein, $R^1$ is isopropyl, $R^2$ is methyl, and $R^3$ is H.

In an exemplary embodiment, the compound is of formula (III) or formula (IV) or formula (V), or a salt, or a hydrate, or a solvate thereof, a, $R^4$, $R^5$ and $R^6$ are as described herein, $R^1$ is t-butyl, $R^2$ is methyl, and $R^3$ is H. In an exemplary embodiment, the compound is of formula (III) or formula (IV) or formula (V), or a salt, or a hydrate, or a solvate thereof, a, $R^4$, $R^5$ and $R^6$ are as described herein, $R^1$ is cyclopropyl, $R^2$ is methyl, and $R^3$ is H. In an exemplary embodiment, the compound is of formula (III) or formula (IV) or formula (V), or a salt, or a hydrate, or a solvate thereof, a, $R^4$, $R^5$ and $R^6$ are as described herein, $R^1$ is isopropyl, $R^2$ is methyl, and $R^3$ is H.

In an exemplary embodiment, the compound is of formula (I) or formula (II), or a salt, or a hydrate, or a solvate thereof, $R^4$ and $R^5$ are as described herein, a is 1, $R^1$ is t-butyl, $R^2$ is methyl, and $R^3$ is H. In an exemplary embodiment, the compound is of formula (I) or formula (II), or a salt, or a hydrate, or a solvate thereof, $R^4$ and $R^5$ are as described herein, a is 1, $R^1$ is cyclopropyl, $R^2$ is methyl, and $R^3$ is H. In an exemplary embodiment, the compound is of formula (I) or formula (II), or a salt, or a hydrate, or a solvate thereof, $R^4$ and $R^5$ are as described herein, a is 1, $R^1$ is isopropyl, $R^2$ is methyl, and $R^3$ is H.

In an exemplary embodiment, the compound is of formula (III) or formula (IV) or formula (V), or a salt, or a hydrate, or a solvate thereof, $R^4$, $R^5$ and $R^6$ are as described herein, a is 1, $R^1$ is t-butyl, $R^2$ is methyl, and $R^3$ is H. In an exemplary embodiment, the compound is of formula (III) or formula (IV) or formula (V), or a salt, or a hydrate, or a solvate thereof, $R^4$, $R^5$ and $R^6$ are as described herein, a is 1, $R^1$ is cyclopropyl, $R^2$ is methyl, and $R^3$ is H. In an exemplary embodiment, the compound is of formula (III) or formula (IV) or formula (V), or a salt, or a hydrate, or a solvate thereof, $R^4$, $R^5$ and $R^6$ are as described herein, a is 1, $R^1$ is isopropyl, $R^2$ is methyl, and $R^3$ is H.

In an exemplary embodiment, the compound is of formula (I) or formula (II), or a salt, or a hydrate, or a solvate thereof, a and $R^4$ are as described herein, $R^1$ is t-butyl, $R^2$ is methyl, $R^3$ is H, and $R^5$ is F. In an exemplary embodiment, the compound is of formula (I) or formula (II), or a salt, or a hydrate, or a solvate thereof, a and $R^4$ are as described herein, $R^1$ is t-butyl, $R^2$ is methyl, $R^3$ is H, and $R^5$ is Cl. In an exemplary embodiment, the compound is of formula (I) or formula (II), or a salt, or a hydrate, or a solvate thereof, a and $R^4$ are as described herein, $R^1$ is t-butyl, $R^2$ is methyl, $R^3$ is H, and $R^5$ is Br. In an exemplary embodiment, the compound is of formula (I) or formula (II), or a salt, or a hydrate, or a solvate thereof, a and $R^4$ are as described herein, $R^1$ is t-butyl, $R^2$ is methyl, $R^3$ is H, and $R^5$ is I. In an exemplary embodiment, the compound is of formula (I) or formula (II), or a salt, or a hydrate, or a solvate thereof, a and $R^4$ are as described herein, $R^1$ is cyclopropyl, $R^2$ is methyl, $R^3$ is H, and $R^5$ is F. In an exemplary embodiment, the compound is of formula (I) or formula (II), or a salt, or a hydrate, or a solvate thereof, a and $R^4$ are as described herein, $R^1$ is cyclopropyl, $R^2$ is methyl, $R^3$ is H, and $R^5$ is Cl. In an exemplary embodiment, the compound is of formula (I) or formula (II), or a salt, or a hydrate, or a solvate thereof, a and $R^4$ are as described herein, $R^1$ is cyclopropyl, $R^2$ is methyl, $R^3$ is H, and $R^5$ is Br. In an exemplary embodiment, the compound is of formula (I) or formula (II), or a salt, or a hydrate, or a solvate thereof, a and $R^4$ are as described herein, $R^1$ is cyclopropyl, $R^2$ is methyl, $R^3$ is H, and $R^5$ is I. In an exemplary embodiment, the compound is of formula (I) or formula (II), or a salt, or a hydrate, or a solvate thereof, a and $R^4$ are as described herein, $R^1$ is isopropyl, $R^2$ is methyl, $R^3$ is H, and $R^5$ is F. In an exemplary embodiment, the compound is of formula (I) or formula (II), or a salt, or a hydrate, or a solvate thereof, a and $R^4$ are as described herein, $R^1$ is isopropyl, $R^2$ is methyl, $R^3$ is H, and $R^5$ is Cl. In an exemplary embodiment, the compound is of formula (I) or formula (II), or a salt, or a hydrate, or a solvate thereof, a and $R^4$ are as described herein, $R^1$ is isopropyl, $R^2$ is methyl, $R^3$ is H, and $R^5$ is Br. In an exemplary embodiment, the compound is of formula (I) or formula (II), or a salt, or a hydrate, or a solvate thereof, a and $R^4$ are as described herein, $R^1$ is isopropyl, $R^2$ is methyl, $R^3$ is H, and $R^5$ is I.

In an exemplary embodiment, the compound is of formula (I) or formula (II), or a salt, or a hydrate, or a solvate thereof, $R^4$ is as described herein, a is 1, $R^1$ is t-butyl, $R^2$ is methyl, $R^3$ is H, and $R^5$ is F. In an exemplary embodiment, the compound is of formula (I) or formula (II), or a salt, or a hydrate, or a solvate thereof, $R^4$ is as described herein, a is 1, $R^1$ is t-butyl, $R^2$ is methyl, $R^3$ is H, and $R^5$ is Cl. In an exemplary embodiment, the compound is of formula (I) or formula (II), or a salt, or a hydrate, or a solvate thereof, $R^4$ is as described herein, a is 1, $R^1$ is t-butyl, $R^2$ is methyl, $R^3$ is H, and $R^5$ is Br. In an exemplary embodiment, the compound is of formula (I) or formula (II), or a salt, or a hydrate, or a solvate thereof, $R^4$ is as described herein, a is 1, $R^1$ is t-butyl, $R^2$ is methyl, $R^3$ is H, and $R^5$ is I. In an exemplary embodiment, the compound is of formula (I) or formula (II), or a salt, or a hydrate, or a solvate thereof, $R^4$ is as described herein, a is 1, $R^1$ is cyclopropyl, $R^2$ is methyl, $R^3$ is H, and $R^5$ is F. In an exemplary embodiment, the compound is of formula (I) or formula (II), or a salt, or a hydrate, or a solvate thereof, $R^4$ is as described herein, a is 1, $R^1$ is cyclopropyl, $R^2$ is methyl, $R^3$ is H, and $R^5$ is Cl. In an exemplary embodiment, the compound is of formula (I) or formula (II), or a salt, or a hydrate, or a solvate thereof, $R^4$ is as described herein, a is 1, $R^1$ is cyclopropyl, $R^2$ is methyl, $R^3$ is H, and $R^5$ is Br. In an exemplary embodiment, the compound is of formula (I) or formula (II), or a salt, or a hydrate, or a solvate thereof, $R^4$ is as described herein, a is 1, $R^1$ is cyclopropyl, $R^2$ is methyl, $R^3$ is H, and $R^5$ is I. In an exemplary embodiment, the compound is of formula (I) or formula (II), or a salt, or a hydrate, or a solvate thereof, $R^4$ is as described herein, a is 1, $R^1$ is isopropyl, $R^2$ is methyl, $R^3$ is H, and $R^5$ is F. In an exemplary embodiment, the compound is of formula (I) or formula (II), or a salt, or a hydrate, or a solvate thereof, $R^4$ is as described herein, a is 1, $R^1$ is isopropyl, $R^2$ is methyl, $R^3$ is H, and $R^5$ is Cl. In an exemplary embodiment, the compound is of formula (I) or formula (II), or a salt, or a hydrate, or a solvate thereof, $R^4$ is as described herein, a is 1, $R^1$ is isopropyl, $R^2$ is methyl, $R^3$ is H, and $R^5$ is Br. In an exemplary embodiment, the compound is of formula (I) or formula (II), or a salt, or a hydrate, or a solvate thereof, $R^4$ is as described herein, a is 1, $R^1$ is isopropyl, $R^2$ is methyl, $R^3$ is H, and $R^5$ is I.

In an exemplary embodiment, the compound is 3-(tert-butyl)-N-(4-chloro-3-methoxybenzyl)-1-methyl-1H-pyrazole-5-carboxamide, or a hydrate, solvate, or salt thereof. In an exemplary embodiment, the compound is N-(4-chloro-3-methoxybenzyl)-3-cyclopropyl-1-methyl-1H-pyrazole-5-carboxamide, or a hydrate, solvate, or salt thereof. In an exemplary embodiment, the compound is 3-(tert-butyl)-N-(3-chloro-4-methoxybenzyl)-1-methyl-1H-pyrazole-5-carboxamide, or a hydrate, solvate, or salt thereof. In an exemplary embodiment, the compound is 3-(tert-butyl)-N-(2-fluoro-3-(trifluoromethoxy)benzyl)-1-methyl-1H-pyrazole-5-carboxamide, or a hydrate, solvate, or salt thereof. In an exemplary embodiment, the compound is 3-cyclopropyl-N-(2-fluoro-3-(trifluoromethoxy)benzyl)-1-methyl-1H-pyrazole-5-carboxamide, or a hydrate, solvate, or salt thereof. In an exemplary embodiment, the compound is 3-(tert-butyl)-N-(3-chloro-4-methylbenzyl)-1-methyl-1H-pyrazole-5-carboxamide, or a hydrate, solvate, or salt thereof. In an exemplary embodiment, the compound is N-(2-fluoro-3-(trifluoromethyl)benzyl)-3-isopropyl-1-methyl-1H-pyrazole-5-carboxamide, or a hydrate, solvate, or salt thereof. In an exemplary embodiment, the compound is N-(2-chloro-3-(trifluoromethyl)benzyl)-3-isopropyl-1-methyl-1H-pyrazole-5-carboxamide, or a hydrate, solvate, or salt thereof. In an exemplary embodiment, the compound is 3-cyclopropyl-N-(3-(cyclopropylmethoxy)-2-fluorobenzyl)-1-methyl-1H-pyrazole-5-carboxamide, or a hydrate, solvate, or salt thereof. In an exemplary embodiment, the compound is N-(3-bromo-4-ethoxybenzyl)-3-(tert-butyl)-1-methyl-1H-pyrazole-5-carboxamide, or a hydrate, solvate, or salt thereof. In an exemplary embodiment, the compound is 3-cyclopropyl-1-methyl-N-(2-methyl-3-(trifluoromethyl)benzyl)-1H-pyrazole-5-carboxamide, or a hydrate, solvate, or salt thereof. In an exemplary embodiment, the compound is 3-cyclopropyl-N-(2-methoxy-3-(trifluoromethyl)benzyl)-1-methyl-1H-pyrazole-5-carboxamide, or a hydrate, solvate, or salt thereof. In an exemplary embodiment, the compound is 3-cyclopropyl-N-(3-methoxy-2-(trifluoromethyl)benzyl)-1-methyl-1H-pyrazole-5-carboxamide, or a hydrate, solvate, or salt thereof. In an exemplary embodiment, the compound is 3-(tert-butyl)-N-(2-methoxy-3-(trifluoromethoxy)benzyl)-1-methyl-1H-pyrazole-5-carboxamide, or a hydrate, solvate, or salt thereof. In an exemplary embodiment, the compound is 3-cyclopropyl-N-(2-methoxy-3-(trifluoromethoxy)benzyl)-1-methyl-1H-pyrazole-5-carboxamide, or a hydrate, solvate, or salt thereof. In an exemplary embodiment, the compound is 3-(tert-butyl)-N-(2-(difluoromethoxy)-3-ethoxybenzyl)-1-methyl-1H-pyrazole-5-carboxamide, or a hydrate, solvate, or salt thereof. In an exemplary embodiment, the compound is 3-cyclopropyl-N-(2-(difluoromethoxy)-3-ethoxybenzyl)-1-methyl-1H-pyrazole-5-carboxamide, or a hydrate, solvate, or salt thereof. In an exemplary embodiment, the compound is N-(3-(cyclopentylmethoxy)-2-methoxybenzyl)-3-cyclopropyl-1-methyl-1H-pyrazole-5-carboxamide, or a hydrate, solvate, or salt thereof. In an exemplary embodiment, the compound is N-(3-chloro-4-ethoxy-5-methoxybenzyl)-3-isopropyl-1-methyl-1H-pyrazole-5-carboxamide, or a hydrate, solvate, or salt thereof.

In an exemplary embodiment, the invention provides a compound of formula (III) or formula (IV) or formula (V), in which $R^1$ and $R^2$ are each independently selected from linear alkyl, branched alkyl, and cycloalkyl; $R^3$ is H; a is an integer selected from 1, 2, 3, 4, 5, and 6; $R^4$ and $R^5$ are each independently selected from the group consisting of linear alkyl, halogen-substituted linear alkyl, branched alkyl, halogen-substituted branched alkyl, cycloalkyl, halogen-substituted linear alkoxy, halogen-substituted branched alkoxy, cycloalkoxy, cycloalkylalkoxy, and halogen; and $R^6$ is halogen. Also provided are hydrates, salts and solvates of these compounds.

In an exemplary embodiment, the invention provides a compound of formula (III) or formula (IV) or formula (V), in which $R^1$ and $R^2$ are each independently selected from linear alkyl, branched alkyl, and cycloalkyl; $R^3$ is H; a is 1; $R^4$ and $R^5$ are each independently selected from the group consisting of linear alkyl, halogen-substituted linear alkyl, branched alkyl, halogen-substituted branched alkyl, cycloalkyl, halogen-substituted linear alkoxy, halogen-substituted branched alkoxy, cycloalkoxy, cycloalkylalkoxy, and halogen; and $R^6$ is halogen. Also provided are hydrates, salts and solvates of these compounds.

In an exemplary embodiment, the invention provides a compound of formula (III) or formula (IV) or formula (V), in which $R^1$ is linear alkyl, branched alkyl, and cycloalkyl; $R^2$ is methyl; $R^3$ is H; a is 1; $R^4$ and $R^5$ are each independently selected from the group consisting of linear alkyl, halogen-substituted linear alkyl, branched alkyl, halogen-substituted branched alkyl, cycloalkyl, halogen-substituted linear alkoxy, halogen-substituted branched alkoxy, cycloalkoxy, cycloalkylalkoxy, and halogen; and $R^6$ is halogen. Also provided are hydrates, salts and solvates of these compounds.

In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ and $R^5$ are each independently selected from the group consisting of linear alkyl, halogen-substituted linear alkyl, branched alkyl, halogen-substituted branched alkyl, cycloalkyl, halogen-substituted linear alkoxy, halogen-substituted branched alkoxy, cycloalkoxy, cycloalkylalkoxy, and halogen; and $R^6$ is halogen. Also provided are hydrates, salts and solvates of these compounds.

In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ and $R^5$ are each independently selected from the group consisting of linear alkyl, halogen-substituted linear alkyl, branched alkyl, halogen-substituted branched alkyl, halogen-substituted linear alkoxy, halogen-substituted branched alkoxy, and halogen; and $R^6$ is halogen. Also provided are hydrates, salts and solvates of these compounds.

In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ and $R^5$ are each independently selected from the group consisting of linear alkyl, halogen-substituted linear alkyl, branched alkyl, halogen-substituted branched alkyl, halogen-substituted linear alkoxy, halogen-substituted branched alkoxy, and halogen; and $R^6$ is F. Also provided are hydrates, salts and solvates of these compounds.

In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ and $R^5$ are each independently selected from the group consisting of linear alkyl, halogen-substituted linear alkyl, branched alkyl, halogen-substituted branched alkyl, halogen-substituted linear alkoxy, halogen-substituted branched alkoxy, and halogen; and $R^6$ is Cl. Also provided are hydrates, salts and solvates of these compounds.

In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ and $R^5$ are each independently selected from the group consisting of linear alkyl, halogen-substituted linear alkyl, branched alkyl, halogen-substituted branched alkyl, halogen-substituted linear alkoxy, halogen-substituted branched alkoxy, and halogen; and $R^6$ is methyl. Also provided are hydrates, salts and solvates of these compounds.

In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ is $C_1$-$C_3$ alkyl or $C_1$-$C_3$ alkoxy or halogen and $R^5$ is as described herein; and $R^6$ is halogen or $C_1$-$C_3$ alkyl. Also provided are hydrates, salts and solvates of these compounds.

In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ is $C_1$-$C_3$ alkyl or $C_1$-$C_3$ alkoxy or halogen and $R^5$ is $C_1$-$C_3$ alkoxy; and $R^6$ is halogen or $C_1$-$C_3$ alkyl. Also provided are hydrates, salts and solvates of these compounds. In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ is $C_1$-$C_3$ alkyl or $C_1$-$C_3$ alkoxy or halogen and $R^5$ is halogen substituted $C_1$-$C_3$ alkoxy; and $R^6$ is halogen or $C_1$-$C_3$ alkyl. Also provided are hydrates, salts and solvates of these compounds.

In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ is methyl or ethyl or methoxy or ethoxy or F or Cl; $R^5$ is methoxy or ethoxy; and $R^6$ is F or Cl or Br or methyl or ethyl. Also provided are hydrates, salts and solvates of these compounds. In an exemplary embodiment, the invention provides a compound of formula (III) or formula (IV) or formula (V), in which $R^1$ is isopropyl or cyclopropyl or t-butyl; $R^2$ is methyl; $R^3$ is H; a is 1; $R^4$ is methyl or ethyl or methoxy or ethoxy or F or Cl; $R^5$ is difluoromethoxy or trifluoromethoxy; and $R^6$ is F or Cl or Br or methyl or ethyl. Also provided are hydrates, salts and solvates of these compounds.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III.b) Preparation of Compounds

Compounds of use in the invention can be prepared using commercially available starting materials, known intermediates, or by using the synthetic methods described herein, or published in references described and incorporated by reference herein.

A General Procedure to Make Compounds of the Invention

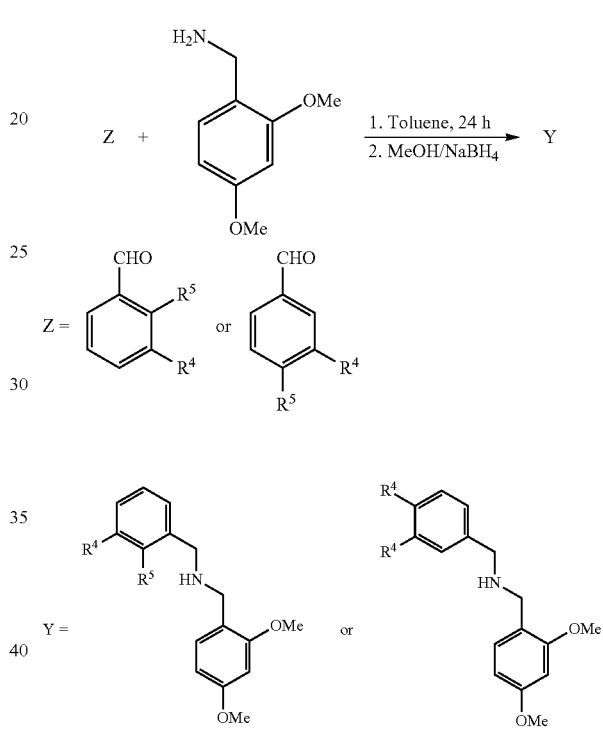

To a solution of aldehyde (Z) in toluene was added an amine (1 eq) and the reaction mixture was stirred at room temperature. Toluene was removed to give a residue, which was taken in MeOH and then NaBH$_4$ was added slowly. The reaction mixture was stirred at room temperature. Solvent was removed and the residue was extracted in ethyl acetate and stirred with saturated aq NaHCO$_3$. The organic layer was collected, dried and solvent was removed to give the crude amine, which was used in the next step without further purification.

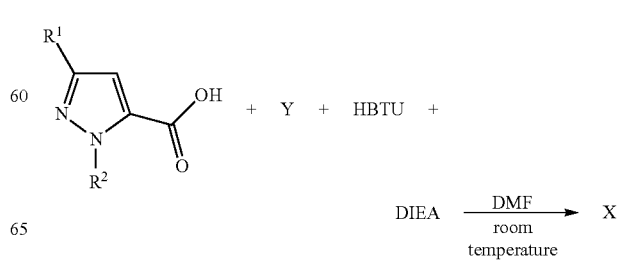

-continued

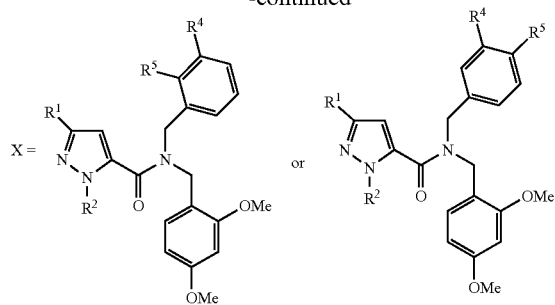

X =

To a solution of an Acid in DMF was added an amine (Y), DIEA and HBTU and the reaction mixture was stirred at rt. The reaction mixture was then diluted with Ethyl acetate and washed with 10% aq HCl (1×), sat $NaHCO_3$ (1×) and water (4×). Organic layer was collected, dried ($MgSO_4$) and evaporated to give a crude product, which was purified by column chromatography (Hexane/EtOAc) to give compound (X). The product was characterized by LCMS.

Compound (X) was then treated with 95% TFA:$H_2O$. TFA was removed and azeotroped with toluene to give a residue, which was purified by column chromatography to give a compound of the invention.

Another General Procedure to Make Compounds of the Invention

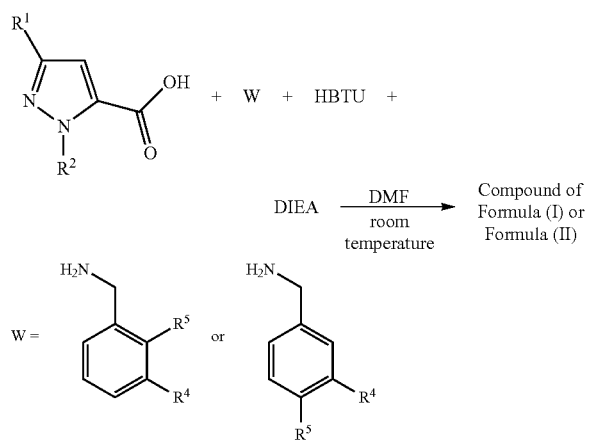

To a solution of an acid in DMF was added an amine (W), DIEA and HBTU and the reaction mixture was stirred at rt. The reaction mixture was then diluted with ethyl acetate and washed with aq HCl, sat $NaHCO_3$ and water. Organic layer was collected, dried ($MgSO_4$) and evaporated to give a crude product, which was purified by column chromatography (Hexane/EtOAc) to give a compound of the invention. The product was characterized by LCMS.

Compounds described herein can be converted into hydrates and solvates by methods similar to those described herein.

IV. Methods of Inhibiting the Replication of a Virus

The compounds of the invention exhibit potency against viruses, and therefore have the potential to inhibit the replication of viruses.

In a further aspect, the invention provides a method of inhibiting the replication of a virus in an animal, comprising administering a compound or a pharmaceutical formulation described herein to the animal, wherein the animal is in need of treatment thereof, thereby inhibiting the replication of the virus in an animal. In an exemplary embodiment, the virus is a virus described herein. In an exemplary embodiment, the virus is a member of the Orthomyxoviridae family. In an exemplary embodiment, the virus is influenzavirus A or influenzavirus B or influenzavirus C. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In an exemplary embodiment, the virus is a corona virus. An exemplary corona virus is porcine epidemic diarrheal virus (PEDV).

In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a pig. In another exemplary embodiment, the animal is a human.

In an exemplary embodiment, the viral replication is inhibited through oral administration of the compound of the invention. In an exemplary embodiment, the viral replication is inhibited through intravenous administration of the compound of the invention. In an exemplary embodiment, the viral replication is inhibited through topical administration of the compound of the invention. In an exemplary embodiment, the viral replication is inhibited through intraperitoneal administration of the compound of the invention. In an exemplary embodiment, the compound is administered in a therapeutically effective amount. In an exemplary embodiment, the compound is administered in a topically effective amount. In an exemplary embodiment, the compound is administered in an orally effective amount. In an exemplary embodiment, the pharmaceutical formulation is administered in a therapeutically effective amount. In an exemplary embodiment, the pharmaceutical formulation is administered in a topically effective amount. In an exemplary embodiment, the pharmaceutical formulation is administered in an orally effective amount.

V. Methods of Treating and/or Preventing Disease

The compounds of the invention exhibit potency against a virus and therefore have the potential to achieve therapeutic efficacy in the animals described herein.

In another aspect, the invention provides a method of treating and/or preventing a disease. The method includes administering to the animal a therapeutically effective amount of the compound of the invention, sufficient to treat and/or prevent the disease. In an exemplary embodiment, the compound of the invention can be used in human or veterinary medical therapy, particularly in the treatment of viral-associated disease. In an exemplary embodiment, the compound of the invention can be used in human or veterinary medical therapy, particularly in the treatment or prophylaxis of coronavirus-associated disease. In an exemplary embodiment, the disease is associated with a virus described herein. In an exemplary embodiment, the disease is associated with a coronavirus. In an exemplary embodiment, the disease is associated with an influenzavirus. In an exemplary embodiment, the disease is influenza. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a pig. In another exemplary embodiment, the animal is a mouse. In another exemplary embodiment, the animal is selected from the group consisting of a human, cattle, goat, pig, sheep, horse, cow, bull, dog, guinea pig, gerbil, rabbit, cat, chicken and turkey. In another exemplary embodiment, the animal is cattle. In another exemplary embodiment, the animal is a cow. In another exemplary embodiment, the animal is a bull.

In an exemplary embodiment, the disease is treated and/or prevented through oral administration of the compound of the invention. In an exemplary embodiment, the disease is treated and/or prevented through intravenous administration of the compound of the invention. In an exemplary embodiment, the disease is treated and/or prevented through topical administration of the compound of the invention. In an exemplary embodiment, the disease is treated and/or prevented through intraperitoneal administration of the compound of the invention. In an exemplary embodiment, the compound is administered in a therapeutically effective amount. In an exemplary embodiment, the compound is administered in a topically effective amount. In an exemplary embodiment, the compound is administered in an orally effective amount. In an exemplary embodiment, the pharmaceutical formulation is administered in a therapeutically effective amount. In an exemplary embodiment, the pharmaceutical formulation is administered in a topically effective amount. In an exemplary embodiment, the pharmaceutical formulation is administered in an orally effective amount.

In an exemplary embodiment, the invention provides a method of treating a disease in an animal. The method includes administering to the animal in need of treatment thereof a therapeutically effective amount of the compound of the invention, sufficient to treat the disease.

In an exemplary embodiment, the invention provides a method of treating porcine epidemic diarrheal virus by administering a therapeutically effective amount of a N-methyl pyrazole, e.g., a compound of the invention.

In an exemplary embodiment, the invention provides a method of treating porcine epidemic diarrheal virus infection in a pig, the method comprising administering to the pig a therapeutically effective amount of a compound of the invention, wherein the pig is in need of treatment thereof, thereby treating porcine epidemic diarrheal virus infection in the pig.

VI. Pharmaceutical Formulations

In another aspect, the invention is a pharmaceutical formulation which includes: (a) a pharmaceutically acceptable excipient; and (b) a N-methyl pyrazole, e.g., a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered intramuscularly. In an exemplary embodiment, the pharmaceutical formulation is administered subcutaneously. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also be added as a food or drink supplement for humans.

Dosage levels of the order of from about 1 mg to about 250 mg per kilogram of body weight per day and more preferably from about 5 mg to about 150 mg per kilogram of body weight per day, and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 5000 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular animal (such as a human) will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 7000 mg of a compound of the invention. In an exemplary embodiment, the unit dosage form contains from about 1 mg to about 5000 mg of an active ingredient. In an exemplary embodiment, the unit dosage form contains from about 100 mg to about 2000 mg of a compound of the invention. In an exemplary embodiment, the unit dosage form contains from about 200 mg to about 1000 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the animal (such as a human) and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat*. B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosages for use in humans or animals. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the human's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of protozoa cell growth. Such information can be used to more accurately determine useful doses in humans or animals.

In general, the compounds prepared by the methods, and from the intermediates, described herein will be administered in a therapeutically effective amount by any of the accepted modes of administration for agents that serve similar utilities. It will be understood, however, that the specific dose level for any particular animal (such as a human) will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain protozoa cell growth inhibitory effects. Usual animal (such as a human) dosages for systemic administration range from 0.1 to 1000 mg/day, preferably, 1-500 mg/day, more preferably 10-200 mg/day, even more preferably 100-200 mg/day. Stated in terms of animal (such as a human) body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention provides a compound which is according to either formula (I) or (II):

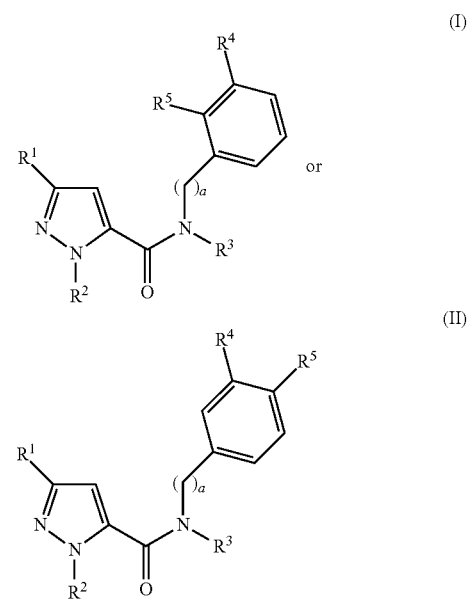

in which $R^1$ and $R^2$ are each independently selected from linear alkyl, branched alkyl, and cycloalkyl; $R^3$ is H; a is an integer selected from 1, 2, 3, 4, 5, and 6; $R^4$ and $R^5$ are each independently selected from linear alkyl, branched alkyl, cycloalkyl, linear alkoxy, branched alkoxy, cycloalkoxy, and halogen, with the proviso that either $R^4$ or $R^5$ is halogen, or a hydrate, or a salt, or a solvate thereof.

In an exemplary embodiment, the invention provides a compound which is 3-(tert-butyl)-N-(4-chloro-3-methoxybenzyl)-1-methyl-1H-pyrazole-5-carboxamide, or a hydrate, or a salt, or a solvate thereof. In an exemplary embodiment, the invention provides a compound which is N-(4-chloro-3-methoxybenzyl)-3-cyclopropyl-1-methyl-1H-pyrazole-5-carboxamide, or a hydrate, or a salt, or a solvate thereof. In an exemplary embodiment, the invention provides a compound which is 3-(tert-butyl)-N-(3-chloro-4-methoxybenzyl)-1-methyl-1H-pyrazole-5-carboxamide, or a hydrate, or a salt, or a solvate thereof. In an exemplary embodiment, the invention provides a compound which is 3-(tert-butyl)-N-(2-fluoro-3-(trifluoromethoxy)benzyl)-1-methyl-1H-pyrazole-5-carboxamide, or a hydrate, or a salt, or a solvate thereof. In an exemplary embodiment, the invention provides a compound which is 3-cyclopropyl-N-(2-fluoro-3-(trifluoromethoxy)benzyl)-1-methyl-1H-pyrazole-5-carboxamide, or a hydrate, or a salt, or a solvate thereof. In an exemplary embodiment, the invention provides a compound which is 3-(tert-butyl)-N-(3-chloro-4-methylbenzyl)-1-methyl-1H-pyrazole-5-carboxamide, or a hydrate, or a salt, or a solvate thereof.

In an exemplary embodiment, the invention provides a pharmaceutical formulation comprising: a) the compound according to any of the above paragraphs, or a pharmaceutically acceptable salt thereof; and b) a pharmaceutically acceptable excipient.

In an exemplary embodiment, the invention provides a method of inhibiting the replication of a virus in an animal, comprising: administering a compound or a pharmaceutical formulation described herein to the animal, wherein the animal is in need of treatment thereof, thereby inhibiting the replication of the virus in an animal.

In an exemplary embodiment, according to any of the above paragraphs, wherein the virus is a member of the Orthomyxoviridae family.

In an exemplary embodiment, according to any of the above paragraphs, wherein the virus is influenzavirus A or influenzavirus B or influenzavirus C.

In an exemplary embodiment, the invention provides a method of treating a disease in an animal, comprising: a) administering a compound or a pharmaceutical formulation described herein to the animal, wherein the animal is in need of treatment thereof, thereby treating the disease in the animal.

In an exemplary embodiment, according to any of the above paragraphs, the disease is influenza.

In an exemplary embodiment, according to any of the above paragraphs, the disease is associated with a coronavirus.

In an exemplary embodiment, according to any of the above paragraphs, the disease is associated with a porcine epidemic diarrheal virus.

In an exemplary embodiment, according to any of the above paragraphs, the animal is a human.

In an exemplary embodiment, according to any of the above paragraphs, the animal is a pig.

In an exemplary embodiment, according to any of the above paragraphs, the invention is a use of a compound of the invention or a pharmaceutical formulation of the invention in the manufacture of a medicament for the treatment of a viral infection.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Büchi Rotary Evaporator.

Analytical HPLC was performed using a Supelco discovery $C_{18}$ 15 cm×4.6 mm/5 μm column coupled with an Agilent 1050 series VWD UV detector at 210 nm. Conditions: Solvent A: $H_2O$/1% acetonitrile/0.1% $HCO_2H$; Solvent B: methanol.

Proton magnetic resonance ($^1H$ NMR) spectra were recorded on a Varian INOVA NMR spectrometer [400 MHz ($^1H$) or 500 MHz ($^1H$)] or Varian 400-MR [400 MHz (1H)]. All spectra were determined in the solvents indicated. Although chemical shifts are reported in ppm downfield of tetramethylsilane, they are referenced to the residual proton peak of the respective solvent peak for $^1H$ NMR. Interproton coupling constants are reported in Hertz (Hz).

LCMS spectra were obtained using a ThermoFinnigan AQA MS ESI instrument utilizing a Phenomenex Aqua 5 micron $C_{18}$ 125 Å 50×4.60 mm column. The spray setting for the MS probe was at 350 μL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer or Agilent 1200 series with a 6140 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepacked silica gel), which were run with a maximum capacity of 1 g crude sample per 10 g silica gel. Samples were preloaded on Celite in Analogix Sample Loading Cartridges with frits (1/in, 1/out). The eluent was 0-100% EtOAc in heptane or 0-10% MeOH in $CH_2Cl_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

Example 1

1) 3-cyclopropyl-N-(2-fluoro-3-(trifluoromethyl)benzyl)-1-methyl-1H-pyrazole-5-carboxamide

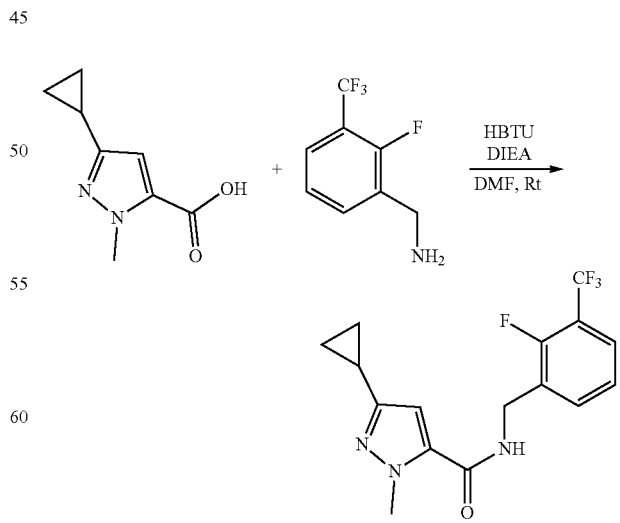

To a solution of amine (95 mg, 0.488 mmol, 1.0 eq) and acid (81 mg, 0.488 mmol, 1.0 eq) in DMF (5 mL) were added DIEA (315 mg, 2.44 mmol, 5 eq) and HBTU (222 mg, 0.586 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product (90 mg, >95% purity). Mass Spectrum (LCMS, ESI Pos.) Calcd. For C$_{16}$H$_{16}$F$_4$N$_3$O$_2$: 342.0 (M+H), Found 342.0.

2) N-(2 fluoro-3-(trifluoromethyl)benzyl)-3-isopropyl-1-methyl-1H pyrazole-5-carboxamide

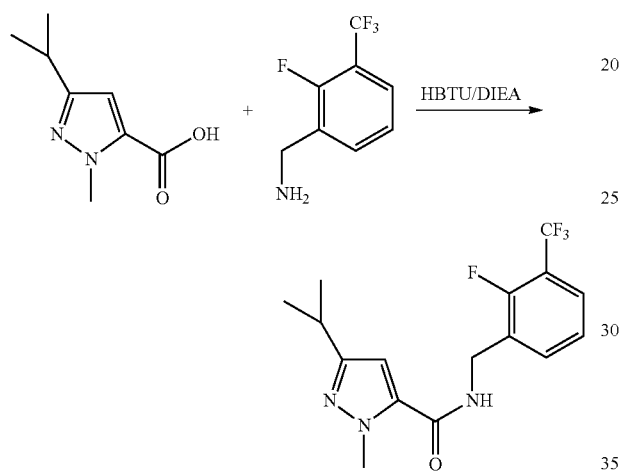

To a solution of amine (250 mg, 1.30 mmol, 1.0 eq) and acid (218 mg, 1.30 mmol, 1.0 eq) in DMF (15 mL) were added DIEA (835 mg, 6.48 mmol, 5 eq) and HBTU (589 mg, 1.55 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product. Mass Spectrum (LCMS, ESI Pos.) Calcd. For C$_{16}$H$_{18}$F$_4$N$_3$O$_2$: 344.0 (M+H), Found 344.0.

3) N-(2-chloro-3-(trifluoromethyl)benzyl)-3-cyclopropyl-1-methyl-1H-pyrazole-5-carboxamide

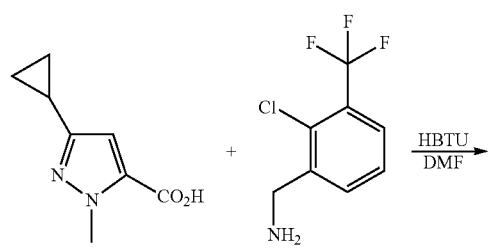

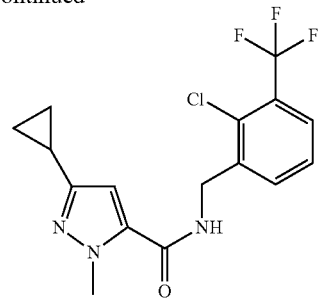

To a solution of amine (500 mg, 2.39 mmol, 1.0 eq) and acid (397 mg, 2.39 mmol, 1.0 eq) in DMF (15 mL) were added DIEA (1.54 g, 11.9 mmol, 5 eq) and HBTU (1.09 mg, 12.87 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product. Mass Spectrum (LCMS, ESI Pos.) Calcd. For C$_{16}$H$_{16}$ClF$_3$N$_3$O: 358.0 (M+H), Found 358.0.

4) N-(2-chloro-3-(trifluoromethyl)benzyl)-3-isopropyl-1-methyl-1H-pyrazole-5-carboxamide

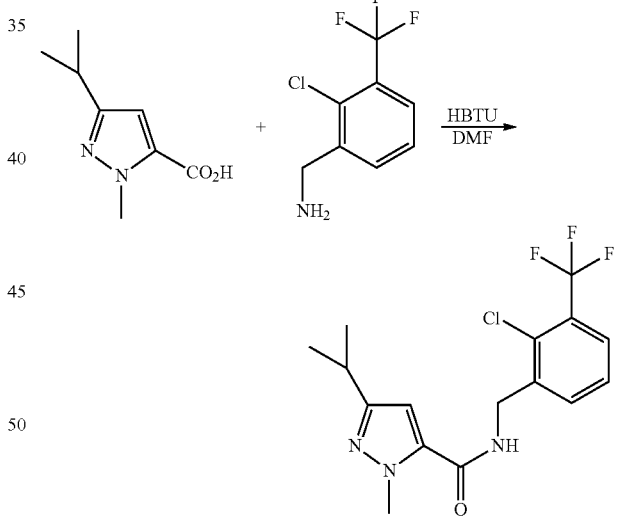

To a solution of amine (500 mg, 2.39 mmol, 1.0 eq) and acid (401 mg, 2.39 mmol, 1.0 eq) in DMF (15 mL) were added DIEA (1.54 g, 11.9 mmol, 5 eq) and HBTU (1.09 mg, 1.2.87 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product. Mass Spectrum (LCMS, ESI Pos.) Calcd. For C$_{16}$H$_{18}$ClF$_3$N$_3$O: 360.0 (M+H), Found 360.0.

5) 3-(tert-butyl)-N-(4-chloro-3-methoxybenzyl)-1-methyl-1H-pyrazole-5-carboxamide

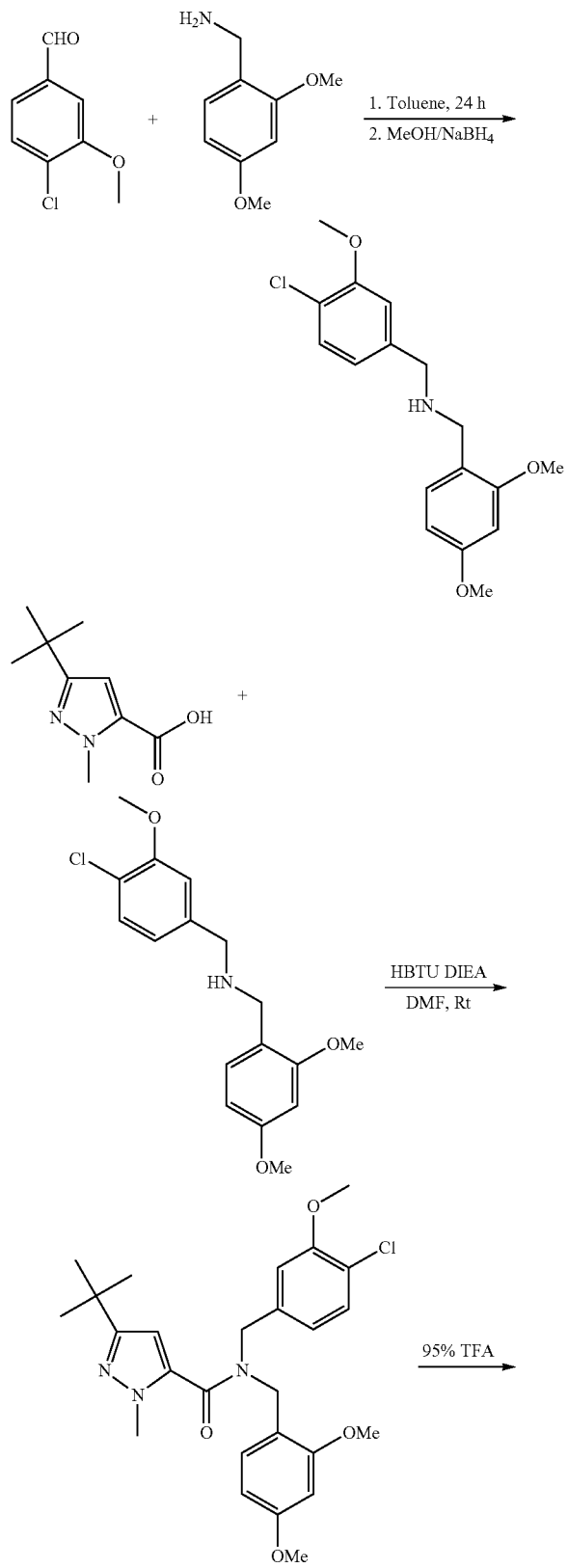

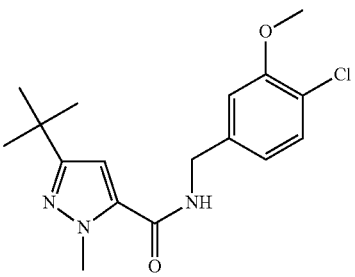 [SMILES: COc1cc(CNC(=O)c2cc(C(C)(C)C)nn2C)ccc1Cl]

To a solution of aldehyde (200 mg, 1.17 mmol, 1.0 eq) in toluene (20 mL) was added 2,4-dimethoxybenzyl amine (215 mg, 1.29 mmol, 1.1 eq) and the reaction mixture was stirred at room temperature for 24 h. Toluene was removed to give a residue, which was taken in MeOH (30 mL) and then NaBH$_4$ (87 mg, 2.34 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (1.17 mmol, 1.0 eq) in DMF (10 mL) was added the acid (234 mg, 1.29 mmol, 1.1 eq), DIEA (755 mg, 5.85 mmol, 5 eq) and HBTU (532 mg, 1.40 mmol, 1.2 eq) and the reaction mixture was stirred at rt for 12 h. The reaction mixture was then diluted with ethyl acetate (200 mL) and washed with 10% aqHCl (1×50 mL), sat NaHCO$_3$ (1×50 mL) and water (4×50 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product in 37% (147 mg, >95% purity). Mass Spectrum (LCMS, ESI Pos.) Calcd. For C$_{17}$H$_{23}$ClN$_3$O$_2$: 336.0 (M+H), Found 336.0.

6) N-(4-chloro-3-methoxybenzyl)-3-cyclopropyl-1-methyl-1H-pyrazole-5-carboxamide

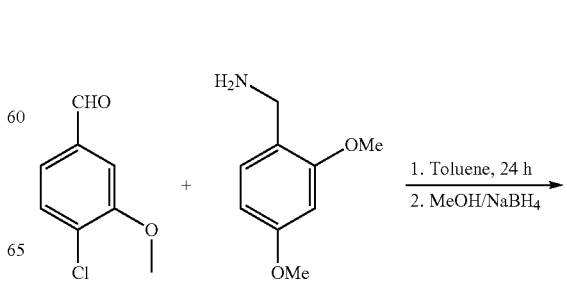

-continued

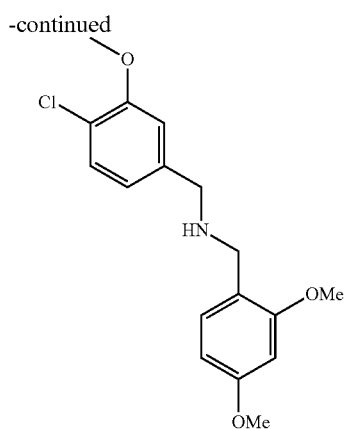

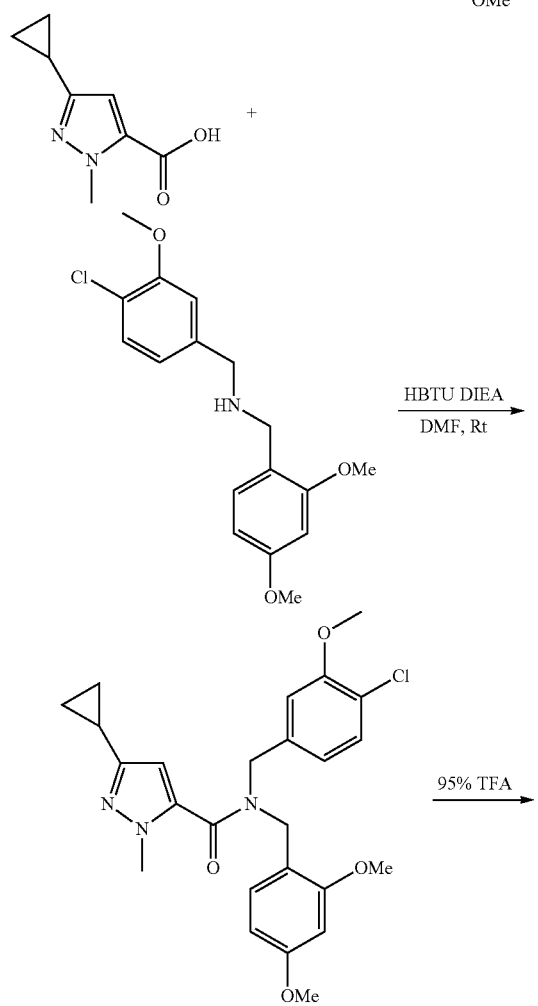

To a solution of aldehyde (1.7 g, 9.95 mmol, 1.0 eq) in toluene (20 mL) was added 2,4-dimethoxybenzyl amine (1.84 g, 10.95 mmol, 1.1 eq) and the reaction mixture was stirred at room temperature for 24 h. Toluene was removed to give a residue, which was taken in MeOH (60 mL) and then NaBH$_4$ (752 mg, 19.9 mmol, 2.0 eq) was added slowly. The reaction mixture was stirred at room temperature for 6 h. Solvent was removed and the residue was extracted in ethyl acetate and stirred with saturated aq NaHCO$_3$ for 1 h. The organic layer was collected, dried and solvent was removed to give the crude amine, which was used in the next step without further purification. To a solution of the crude amine (620 mg, 1.92 mmol, 1.0 eq) in DMF (10 mL) was added the acid (352 mg, 2.12 mmol, 1.1 eq), DIEA (1.20 g, 9.6 mmol, 5 eq) and HBTU (873 mg, 2.3 mmol, 1.2 eq) and the reaction mixture was stirred at rt for 12 h. The reaction mixture was then diluted with ethyl acetate (200 mL) and washed with 10% aqHCl (1×50 mL), sat NaHCO$_3$ (1×50 mL) and water (4×50 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product in 28% (59 mg, >95% purity). Mass Spectrum (LCMS, ESI Pos.) Calcd. For $C_{16}H_{19}ClN_3O_2$: 320.0 (M+H), Found 320.0.

7) 3-(tert-butyl)-N-(2-fluoro-3-(trifluoromethoxy)benzyl)-1-methyl-1H-pyrazole-5-carboxamide

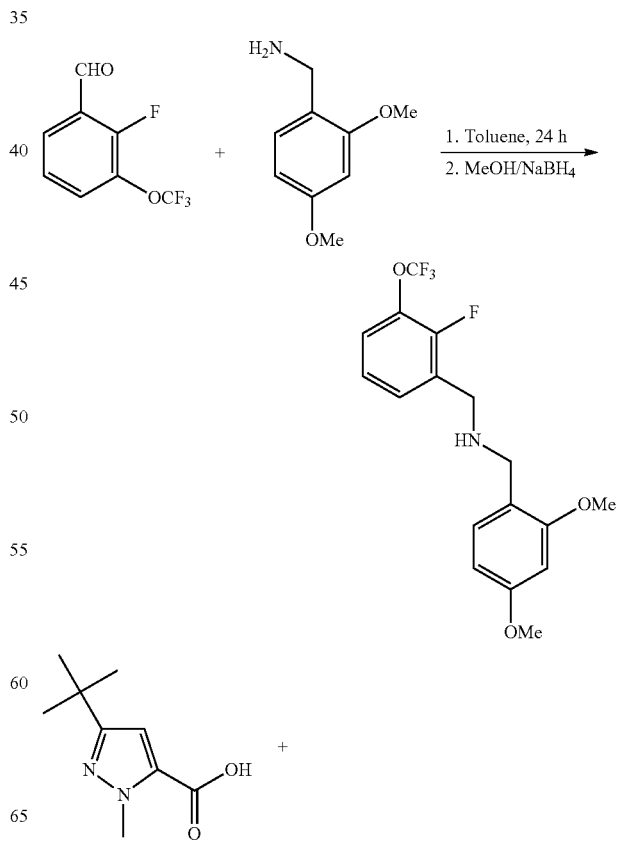

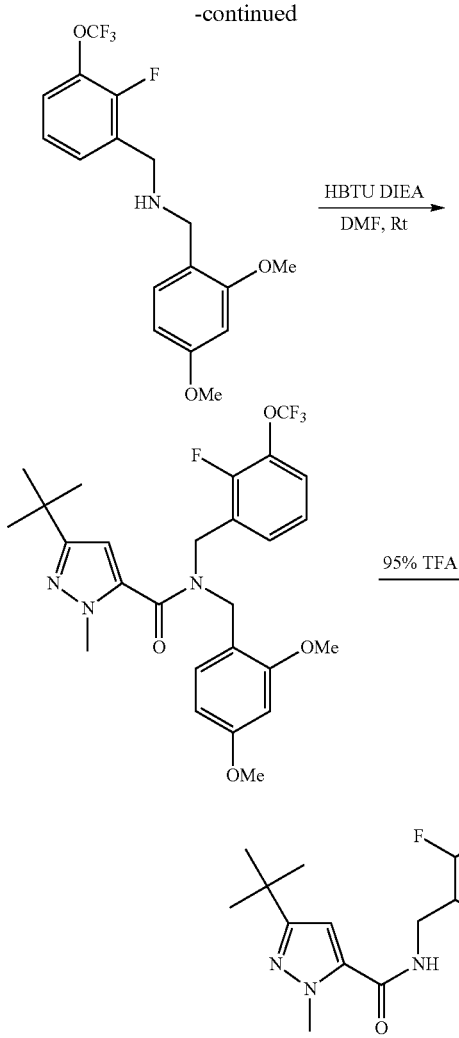

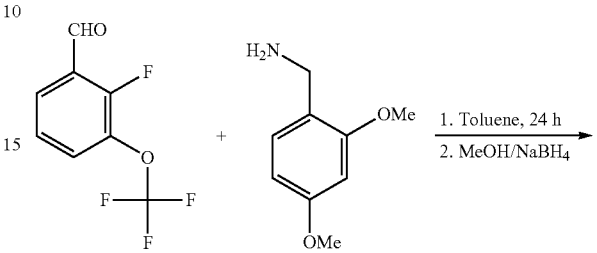

desired product in 28% (183 mg, >95% purity). Mass Spectrum (LCMS, ESI Pos.) Calcd. For $C_{17}H_{20}F_4N_3O_2$: 374.0 (M+H), Found 374.0.

8) 3-cyclopropyl-N-(2-fluoro-3-(trifluoromethoxy)benzyl)-1-methyl-1H-pyrazole-5-carboxamide

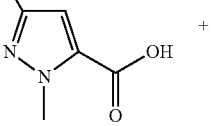

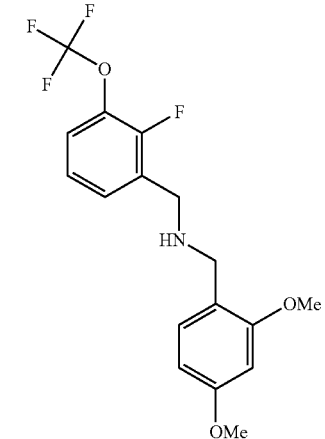

To a solution of aldehyde (200 mg, 0.96 mmol, 1.0 eq) in toluene (20 mL) was added 2,4-dimethoxybenzyl amine (177 mg, 1.06 mmol, 1.1 eq) and the reaction mixture was stirred at room temperature for 24 h. Toluene was removed to give a residue, which was taken in MeOH (30 mL) and then NaBH$_4$ (73 mg, 1.92 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (0.96 mmol, 1.0 eq) in DMF (10 mL) was added the acid (175 mg, 0.96 mmol, 1.0 eq), DIEA (620 mg, 4.8 mmol, 5 eq) and HBTU (440 mg, 1.152 mmol, 1.2 eq) and the reaction mixture was stirred at rt for 12 h. The reaction mixture was then diluted with ethyl acetate (200 mL) and washed with 10% aqHCl (1×50 mL), sat NaHCO$_3$ (1×50 mL) and water (4×50 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the

59

-continued

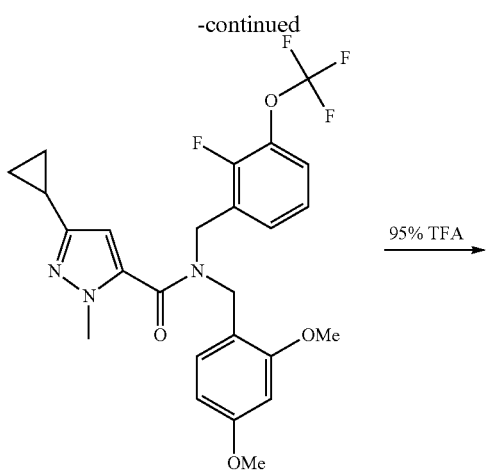

95% TFA →

To a solution of aldehyde (250 mg, 1.20 mmol, 1.0 eq) in toluene (20 mL) was added 2,4-dimethoxybenzyl amine (201 mg, 1.20 mmol, 1.0 eq) and the reaction mixture was stirred at room temperature for 24 h. Toluene was removed to give a residue, which was taken in MeOH (20 mL) and then NaBH$_4$ (91 mg, 2.40 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (1.20 mmol, 1.0 eq) in DMF (10 mL) was added the acid (199 mg, 1.20 mmol, 1.0 eq), DIEA (774 mg, 6.0 mmol, 5 eq) and HBTU (546 mg, 1.44 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product in 22% (93 mg, >95% purity). Mass Spectrum (LCMS, ESI Pos.) Calcd. For C$_{16}$H$_{16}$F$_4$N$_3$O$_2$: 358.0 (M+H), Found 358.0.

60

9) N-(2-fluoro-3-(trifluoromethoxy)benzyl)-3-isopropyl-1-methyl-1H-pyrazole-5-carboxamide

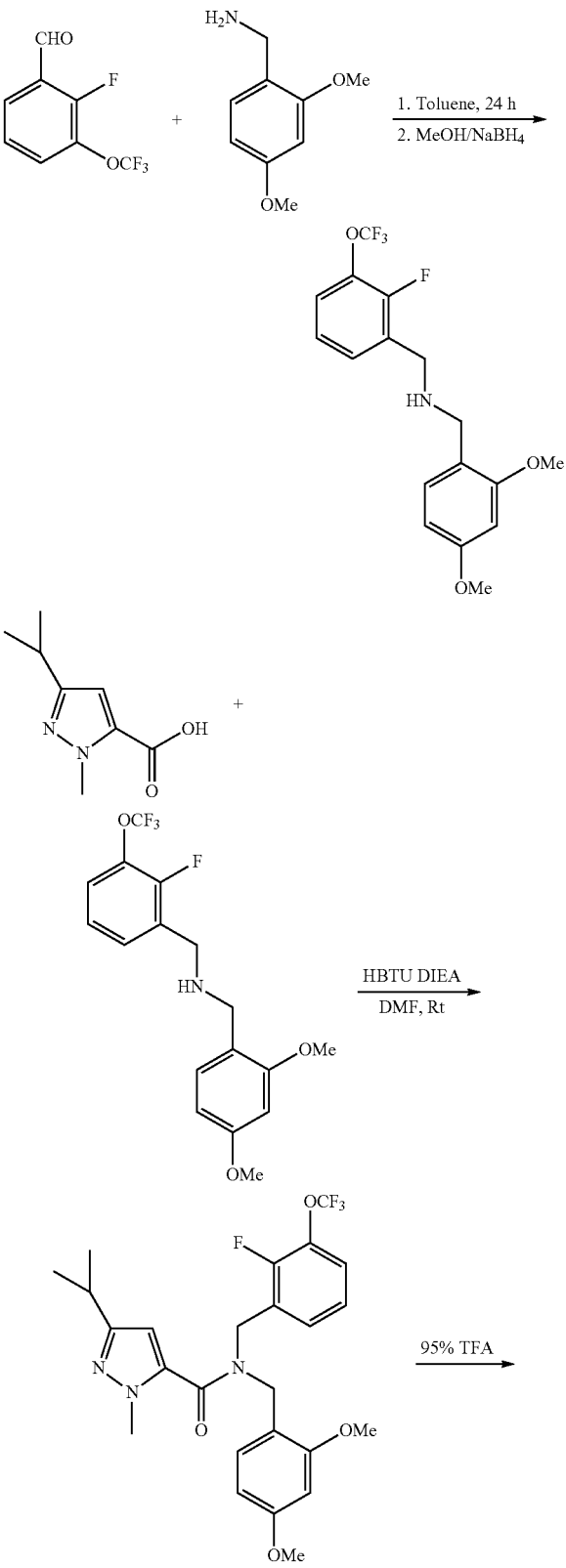

-continued

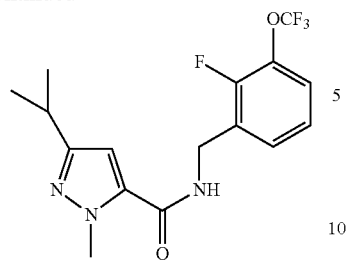

To a solution of aldehyde (1.0 g, 4.81 mmol, 1.0 eq) in toluene (20 mL) was added 2,4-dimethoxybenzyl amine (804 mg, 4.81 mmol, 1.0 eq) and the reaction mixture was stirred at room temperature for 24 h. Toluene was removed to give a residue, which was taken in MeOH (20 mL) and then NaBH₄ (364 mg, 9.62 mmol, 2.0 eq) was added slowly. The reaction mixture was stirred at room temperature for 6 h. Solvent was removed and the residue was extracted in Ethyl acetate and stirred with saturated aq NaHCO₃ for 1 h. The organic layer was collected, dried and solvent was removed to give the crude amine, which was used in the next step without further purification. To a solution of the crude amine (4.81 mmol, 1.0 eq) in DMF (15 mL) was added the acid (808 mg, 4.81 mmol, 1.0 eq), DIEA (3.10 g, 24.05 mmol, 5 eq) and HBTU (2.2 g, 5.77 mmol, 1.2 eq) and the reaction mixture was stirred at rt for 12 h. The reaction mixture was then diluted with ethyl acetate (20 mL) and washed with 10% aqHCl (1×20 mL), sat NaHCO₃ (1×20 mL) and water (4×20 mL). Organic layer was collected, dried (MgSO₄) and evaporated to give a crude product, which was purified by column chromatography (EtOAc/Hexane 25% to 75%)) to give the amide, which was directly used in the next step. The amide was treated with 95% TFA:H₂O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For $C_{16}H_{18}F_4N_3O_2$: 360.0 (M+H), Found 360.0.

10) 3-cyclopropyl-N-(3-(cyclopropylmethoxy)-2-fluorobenzyl)-1-methyl-1H-pyrazole-5-carboxamide

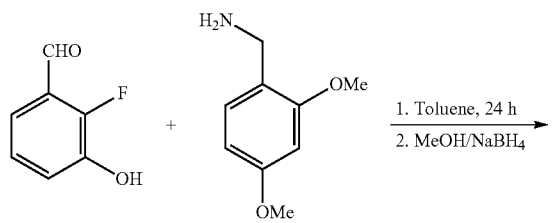

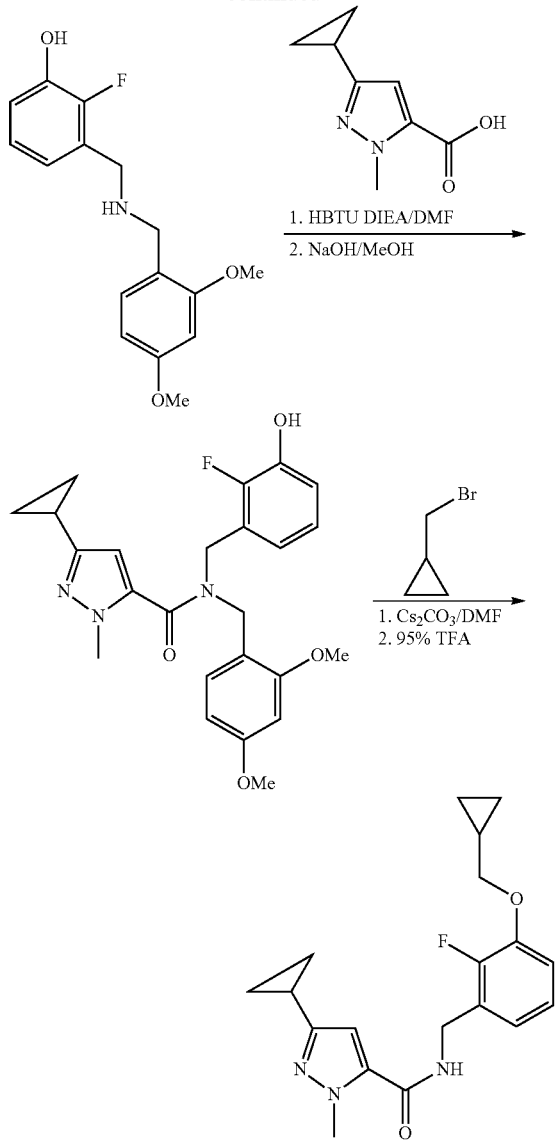

To a solution of aldehyde (1.0 g, 7.14 mmol, 1.0 eq) in toluene (20 mL) was added 2,4-dimethoxybenzyl amine (1.2 g, 7.14 mmol, 1.0 eq) and the reaction mixture was stirred at room temperature for 24 h. Toluene was removed to give a residue, which was taken in MeOH (25 mL) and then NaBH₄ (540 mg, 14.28 mmol, 2.0 eq) was added slowly. The reaction mixture was stirred at room temperature for 6 h. Solvent was removed and the residue was extracted in Ethyl acetate and stirred with saturated aq NaHCO₃ for 1 h. The organic layer was collected, dried and solvent was removed to give the crude amine, which was used in the next step without further purification. To a solution of the crude amine (7.14 mmol, 1.0 eq) in DMF (10 mL) was added the acid (1.20 g, 7.14 mmol, 1.0 eq), DIEA (4.61 g, 35.72 mmol, 5 eq) and HBTU (3.25 g, 8.57 mmol, 1.2 eq) and the reaction mixture was stirred at rt for 12 h. The reaction mixture was then diluted with ethyl acetate (20 mL) and washed with 10% aqHCl (1×30 mL), sat NaHCO₃ (1×30 mL) and water (4×30 mL). Organic layer was collected, dried (MgSO₄) and evaporated to give a crude product, which was taken in 25 mL of methanol and NaOH (286 mg, 7.14 mmol, 1.0 eq) was added and stirred at room temperature for 24 h. Methanol was removed and the residue was neutralized with 10% aq HCl. The reaction mixture was then extracted with ethyl acetate (2×). Organic layer was collected, dried (MgSO$_4$) and evaporated to give a crude product, which was purified by column chromatography (EtOAc/Hexane) to give the amide.

To a solution of the hydroxy amide (360 m g, 0.82 mmol, 1.0 eq) in DMF (10 mL) was added Cs$_2$CO$_3$ (1.34 g, 615 mmol, 2.0 eq) and stirred at room temperature for 20 min. Then bromide (221 mg, 1.64 mmol, 2 eq) was added and stirred at rt for 24 h. The reaction mixture was then diluted with Ethyl acetate (25 mL) and washed with water (4×). Organic layer was collected, dried (MgSO$_4$) and evaporated to give a residue, which was then treated with 95% TFA:H$_2$O for 12 h. TFA was removed and azeotroped with toluene to give a residue, which was purified by column chromatography (EtOAc/Hexane 10% to 50%) to give the desired product (22 mg, >95% purity). Mass Spectrum (LCMS, ESI Pos.) Calcd. For C$_{19}$H$_{22}$CFN$_3$O$_2$: 344.0 (M+H), Found 344.0.

11) 3-(tert-butyl)-N-(3-chloro-4-methylbenzyl)-1-methyl-1H-pyrazole-5-carboxamide

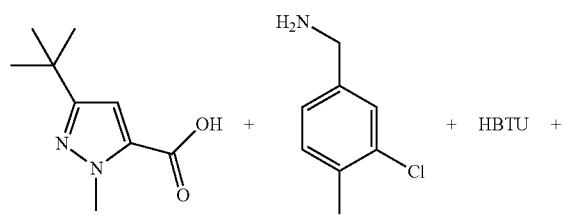

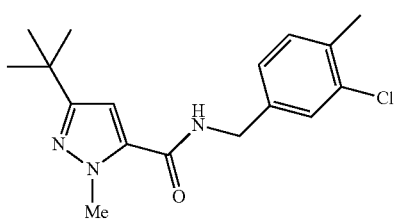

To a solution of the Acid (257 mg, 1.41 mmol, 1.1 eq) in DMF (10 mL) was added an amine (200 mg, 1.29 mmol, 1.0 eq), DIEA (830 mg, 6.43 mmol, 5 eq) and HBTU (584 mg, 1.54 mmol, 1.2 eq) and the reaction mixture was stirred at rt for 12 h. The reaction mixture was then diluted with ethyl acetate (30 mL) and washed with 10% aqHCl (1×25 mL), sat NaHCO$_3$ (1×25 mL) and water (4×25 mL). Organic layer was collected, dried (MgSO$_4$) and evaporated to give a crude product, which was purified by column chromatography (10% to 50% EtOAc in Hexane) to give the amide as a colorless solid in 66% (165 mg, >95% purity). Mass Spectrum (LCMS, ESI Pos.) Calcd. For C$_{17}$H$_{23}$ClN$_3$O: 320.0 (M+H), Found 320.0.

12) 3-(tert-butyl)-N-(3-chloro-4-methoxybenzyl)-1-methyl-1H-pyrazole-5-carboxamide

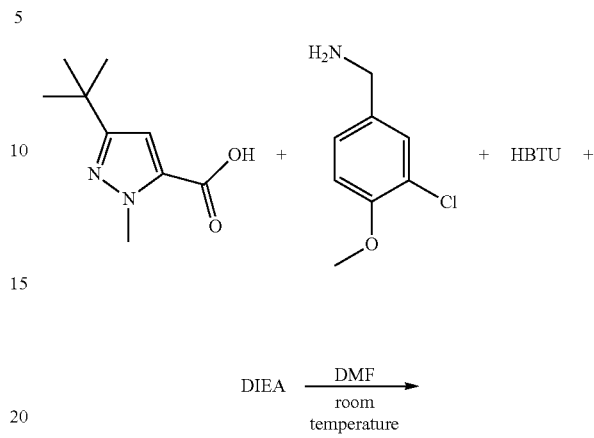

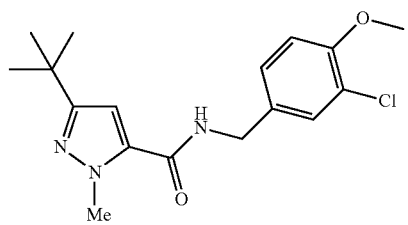

To a solution of the Acid (117 mg, 0.641 mmol, 1.1 eq) in DMF (10 mL) was added an amine (100 mg, 583 mmol, 1.0 eq), DIEA (376 mg, 2.92 mmol, 5 eq) and HBTU (265 mg, 0.70 mmol, 1.2 eq) and the reaction mixture was stirred at rt for 12 h. The reaction mixture was then diluted with ethyl acetate (30 mL) and washed with 10% aqHCl (1×25 mL), sat NaHCO$_3$ (1×25 mL) and water (4×25 mL). Organic layer was collected, dried (MgSO$_4$) and evaporated to give a crude product, which was purified by column chromatography (10% to 50% EtOAc in Hexane) to give the amide as a colorless solid in 66% (66 mg, >95% purity). Mass Spectrum (LCMS, ESI Pos.) Calcd. For C$_{17}$H$_{23}$ClN$_3$O$_2$: 336.0 (M+H), Found 336.0.

13) N-(3-chloro-4-propoxybenzyl)-3-isopropyl-1-methyl-1H-pyrazole-5-carboxamide

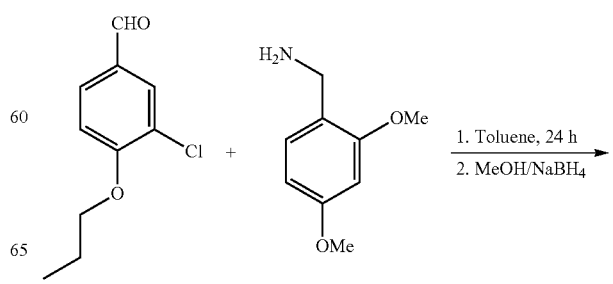

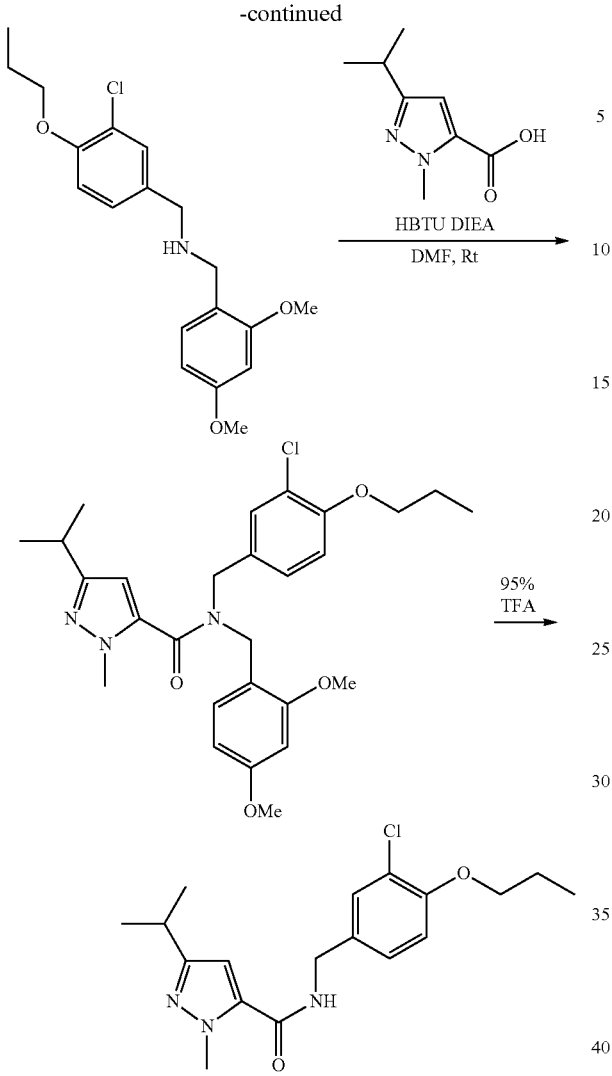

toluene to give a residue, which was purified by column chromatography (EtOAc/Hexane 10% to 50%) to give the desired product (308 mg, >95% purity). Mass Spectrum (LCMS, ESI Pos.) Calcd. For $C_{18}H_{25}ClN_3O_2$: 350.0 (M+H), Found 350.0.

14) N-(3-chloro-4-(cyclopropylmethoxy)benzyl)-3-cyclopropyl-1-methyl-1H-pyrazole-5-carboxamide

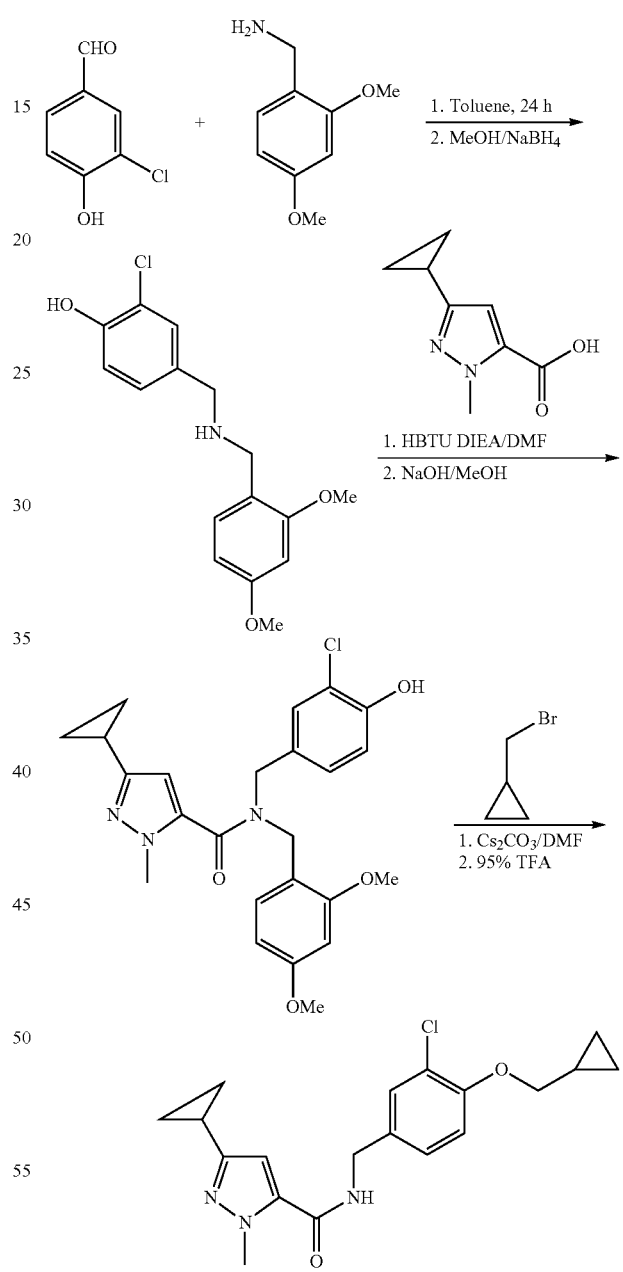

To a solution of aldehyde (500 mg, 2.53 mmol, 1.0 eq) in toluene (25 mL) was added 2,4-dimethoxybenzyl amine (464 mg, 2.78 mmol, 1.1 eq) and the reaction mixture was stirred at room temperature for 24 h. Toluene was removed to give a residue, which was taken in MeOH (25 mL) and then NaBH$_4$ (192 mg, 5.06 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (1.27 mmol, 1.0 eq) in DMF (10 mL) was added the acid (212 mg, 1.27 mmol, 1.0 eq), DIEA (0.816 mg, 1.13 mmol, 5 eq) and HBTU (575 mg, 1.52 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with To a solution of aldehyde (5.0 g, 32.05 mmol, 1.0 eq) in toluene (50 mL) was added 2,4-dimethoxybenzyl amine (5.36 g, 32.05 mmol, 1.0 eq) and the reaction mixture was stirred at room temperature for 24 h. Toluene was removed to give a residue, which was taken in MeOH (50 mL) and then NaBH$_4$ (2.43 g, 64.1 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (12.82 mmol, 1.0 eq) in DMF (30 mL) were added the acid (2.34 g, 14.10 mmol, 1.1 eq), DIEA (8.27 g, 64.10 mmol, 5 eq) and HBTU (5.83 g, 15.38 mmol, 1.2 eq) and the reaction mixture was stirred at rt for 12 h. The reaction mixture was then diluted with ethyl acetate (50 mL) and washed with 10% aq HCl (1×30 mL), sat NaHCO$_3$ (1×30 mL) and water (4×30 mL). Organic layer was collected, dried (MgSO$_4$) and evaporated to give a crude product, which was taken in 50 mL of methanol and NaOH (513 mg, 12.82 mmol, 1.0 eq) was added and stirred at room temperature for 24 h. Methanol was removed and the residue was neutralized with 10% aq HCl. The reaction mixture was then extracted with ethyl acetate (2×). Organic layer was collected, dried (MgSO$_4$) and evaporated to give a crude product, which was purified by column chromatography (EtOAc/Hexane) to give the hydroxyl amide.

To a solution of the hydroxy amide (0.588 mmol, 1.0 eq) in DMF (10 mL) was added Cs$_2$CO$_3$ (382 mg, 1.18 mmol, 2.0 eq) and stirred at room temperature for 20 min. Then bromide (160 mg, 1.18 mmol, 2 eq) was added and stirred at rt for 24 h. The reaction mixture was then diluted with Ethyl acetate (25 mL) and washed with water (4×). Organic layer was collected, dried (MgSO$_4$) and evaporated to give a residue, which was then treated with 95% TFA:H$_2$O for 12 h. TFA was removed and azeotroped with toluene to give a residue, which was purified by column chromatography (EtOAc/Hexane 10% to 50%) to give the desired product (16.1 mg, >95% purity). Mass Spectrum (LCMS, ESI Pos.) Calcd. For C$_{19}$H$_{23}$ClN$_3$O$_2$: 360.0 (M+H), Found 360.0.

15) N-(3-chloro-4-(cyclopropylmethoxy)benzyl)-3-isopropyl-1-methyl-1H-pyrazole-5-carboxamide

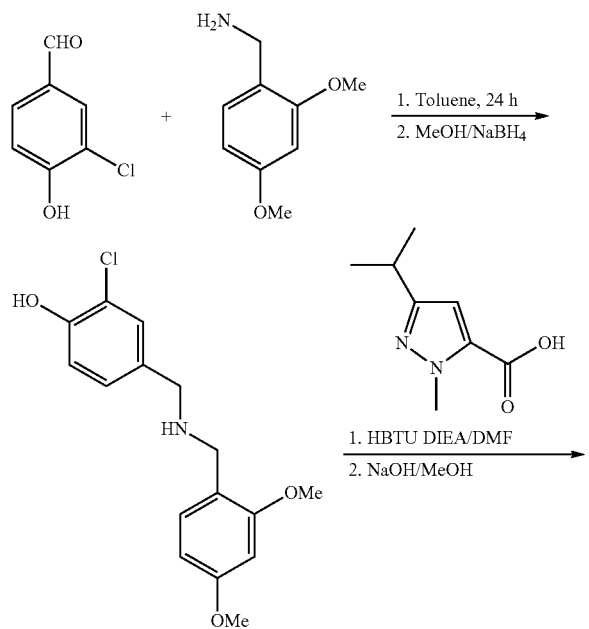

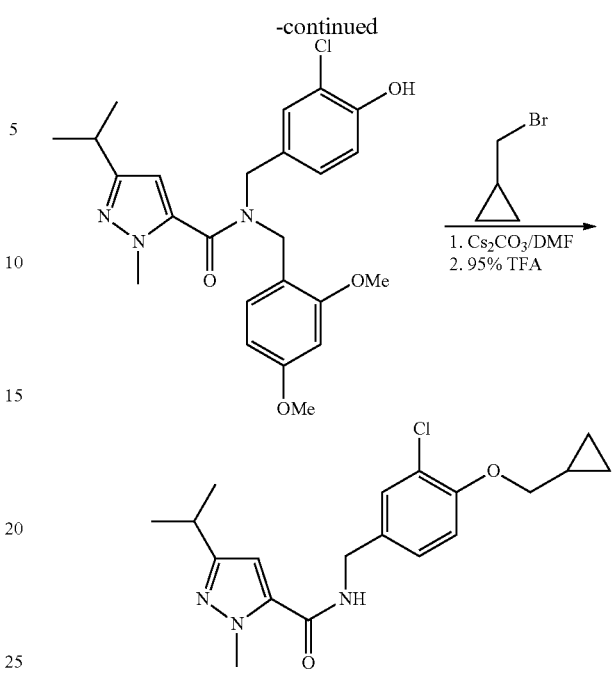

To a solution of aldehyde (5.0 g, 32.05 mmol, 1.0 eq) in toluene (50 mL) was added 2,4-dimethoxybenzyl amine (5.36 g, 32.05 mmol, 1.0 eq) and the reaction mixture was stirred at room temperature for 24 h. Toluene was removed to give a residue, which was taken in MeOH (50 mL) and then NaBH$_4$ (2.43 g, 64.1 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (1.79 mmol, 1.0 eq) in DMF (10 mL) was added the acid (300 mg, 1.79 mmol, 1.0 eq), DIEA (1.39 mg, 10.75 mmol, 5 eq) and HBTU (814 mg, 2.15 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was taken in 25 mL of methanol and NaOH (72 mg, 1.79 mmol, 1.0 eq) was added and stirred at room temperature for 24 h. Methanol was removed and the residue was neutralized with 10% aq HCl. The reaction mixture was then extracted with ethyl acetate (2×). Organic layer was collected, dried (MgSO$_4$) and evaporated to give a crude product, which was purified by column chromatography (EtOAc/Hexane) to give the amide.

To a solution of the hydroxy amide (1.79 mmol, 1.0 eq) in DMF (15 mL) was added Cs$_2$CO$_3$ (1.34 g, 3.58 mmol, 2.0 eq) and stirred at room temperature for 20 min. Then bromide (967 mg, 7.16 mmol, 4 eq) was added and stirred at rt for 24 h. The reaction mixture was then diluted with ethyl acetate (25 mL) and washed with water (4×). Organic layer was collected, dried (MgSO$_4$) and evaporated to give a residue, which was then treated with 95% TFA:H$_2$O for 12 h. TFA was removed and azeotroped with toluene to give a residue, which was purified by column chromatography (EtOAc/Hexane 10% to 50%) to give the desired product (9 mg, >95% purity). Mass Spectrum (LCMS, ESI Pos.) Calcd. For $C_{19}H_{24}ClN_3O_2$: 362.0 (M+H), Found 362.0.

16) N-(3-bromo-4-ethoxybenzyl)-3-(tert-butyl)-1-methyl-1H-pyrazole-5-carboxamide

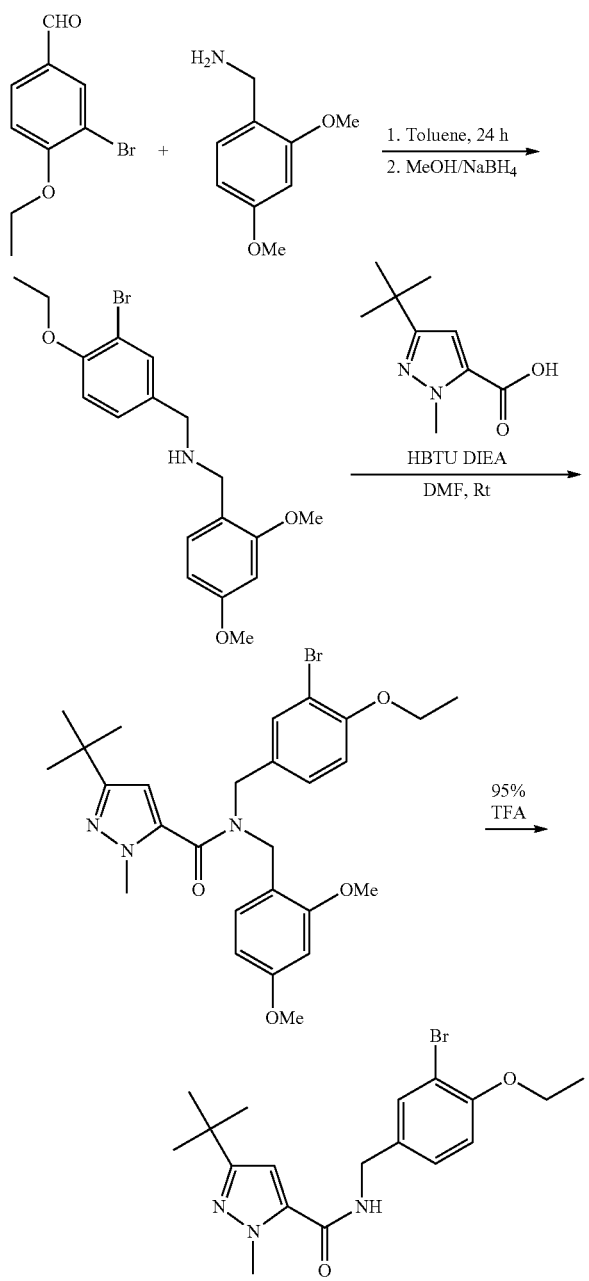

To a solution of aldehyde (1.0 g, 437 mmol, 1.0 eq) in toluene (25 mL) was added 2,4-dimethoxybenzyl amine (802 mg, 4.80 mmol, 1.1 eq) and the reaction mixture was stirred at room temperature for 24 h. Toluene was removed to give a residue, which was taken in MeOH (25 mL) and then NaBH$_4$ (330 mg, 8.74 mmol, 2.0 eq) was added slowly. The reaction mixture was stirred at room temperature for 6 h. Solvent was removed and the residue was extracted in ethyl acetate and stirred with saturated aq NaHCO$_3$ for 1 h. The organic layer was collected, dried and solvent was removed to give the crude amine, which was used in the next step without further purification. To a solution of the crude amine (1.46 mmol, 1.0 eq) in DMF (15 mL) was added the acid (263 mg, 1.46 mmol, 1.0 eq), DIEA (939 mg, 1.30 mmol, 5 eq) and HBTU (662 mg, 1.75 mmol, 1.2 eq) and the reaction mixture was stirred at rt for 12 h. The reaction mixture was then diluted with Ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For $C_{18}H_{25}BrN_3O_2$: 394.0 (M+H), Found 394.0.

17) N-(3-bromo-4-ethoxybenzyl)-3-isopropyl-1-methyl-1H-pyrazole-5-carboxamide

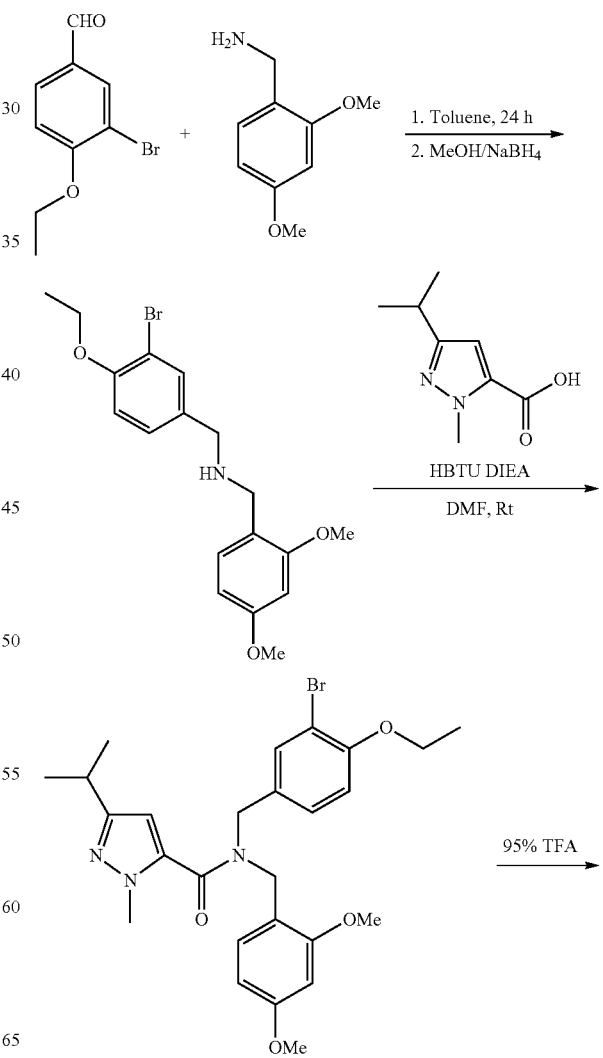

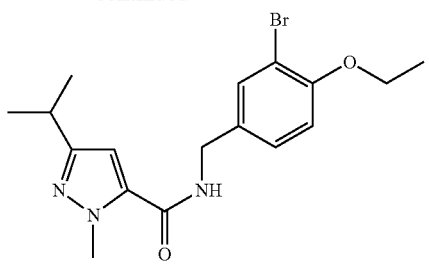

To a solution of aldehyde (1.0 g, 437 mmol, 1.0 eq) in toluene (25 mL) was added 2,4-dimethoxybenzyl amine (802 mg, 4.80 mmol, 1.1 eq) and the reaction mixture was stirred at room temperature for 24 h. Toluene was removed to give a residue, which was taken in MeOH (25 mL) and then NaBH$_4$ (330 mg, 8.74 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (1.46 mmol, 1.0 eq) in DMF (15 mL) was added the acid (244 mg, 1.46 mmol, 1.0 eq), DIEA (939 mg, 1.30 mmol, 5 eq) and HBTU (662 mg, 1.75 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For C$_{17}$H$_{23}$BrN$_3$O$_2$: 380.0 (M+H), Found 380.0.

18) N-(3-bromo-2-methoxybenzyl)-3-cyclopropyl-1-methyl-1H-pyrazole-5-carboxamide

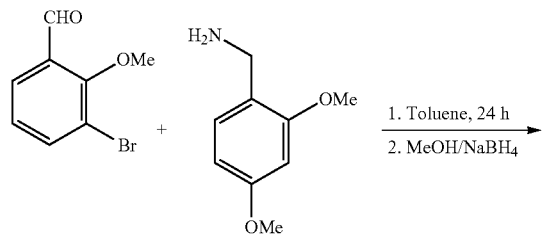

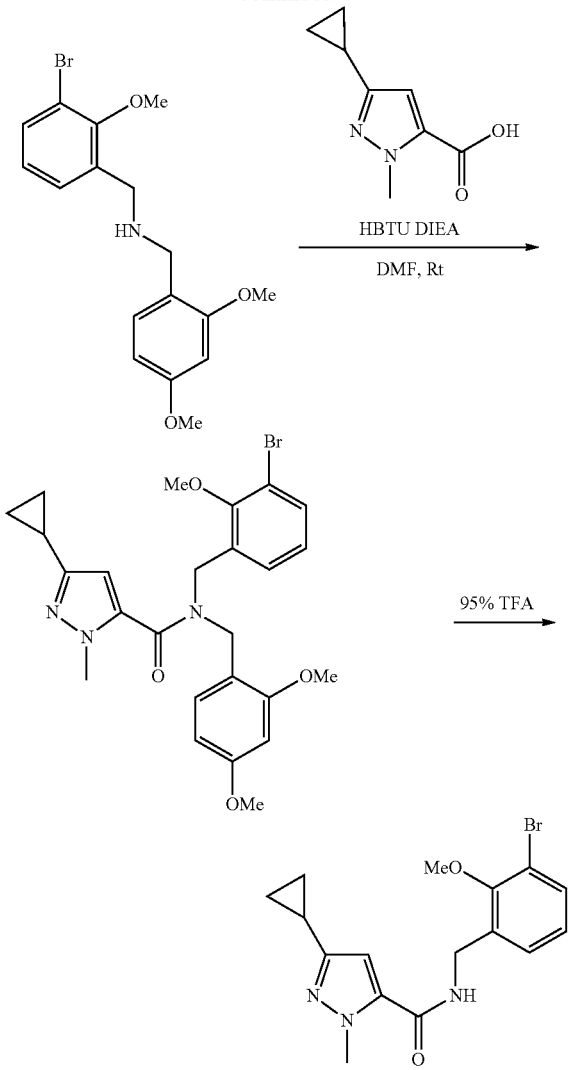

To a solution of aldehyde (1.0 g, 4.65 mmol, 1.0 eq) in toluene (25 mL) was added 2,4-dimethoxybenzyl amine (857 mg, 5.12 mmol, 1.10 eq) and the reaction mixture was stirred at room temperature for 24 h. Toluene was removed to give a residue, which was taken in MeOH (25 mL) and then NaBH$_4$ (352 mg, 9.30 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (4.65 mmol, 1.0 eq) in DMF (15 mL) was added the acid (737 mg, 4.65 mmol, 1.0 eq), DIEA (3.0 g, 23.25 mmol, 5 eq) and HBTU (2.12 g, 5.58 mmol, 1.2 eq) and the reaction mixture was stirred at rt for 12 h. The reaction mixture was then diluted with ethyl acetate (50 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For $C_{16}H_{19}BrN_3O_2$: 364.0 (M+H), Found 364.0.

19) 3-cyclopropyl-N-(3-fluoro-2-methylbenzyl)-1-methyl-1H-pyrazole-5-carboxamide

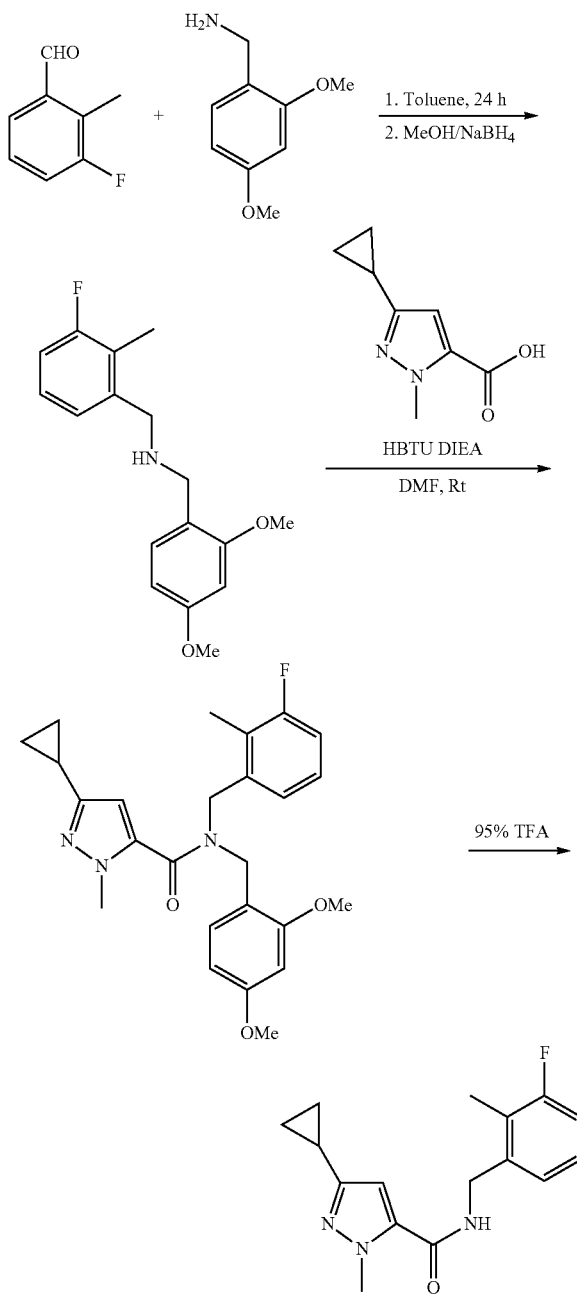

To a solution of aldehyde (500 mg, 3.62 mmol, 1.0 eq) in toluene (15 mL) was added 2,4-dimethoxybenzyl amine (605 mg, 3.62 mmol, 1.0 eq) and the reaction mixture was stirred at room temperature for 24 h. Toluene was removed to give a residue, which was taken in MeOH (15 mL) and then NaBH$_4$ (274 mg, 7.24 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (3.62 mmol, 1.0 eq) in DMF (15 mL) was added the acid (600 mg, 3.62 mmol, 1.0 eq), DIEA (2.33 g, 18.1 mmol, 5 eq) and HBTU (1.65 g, 4.34 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product (282 mg, >95% purity). Mass Spectrum (LCMS, ESI Pos.) Calcd. For $C_{18}H_{19}FN_3O$: 288.0 (M+H), Found 288.0.

20) 3-cyclopropyl-N-(2,3-dimethylbenzyl)-1-methyl-1H-pyrazole-5-carboxamide

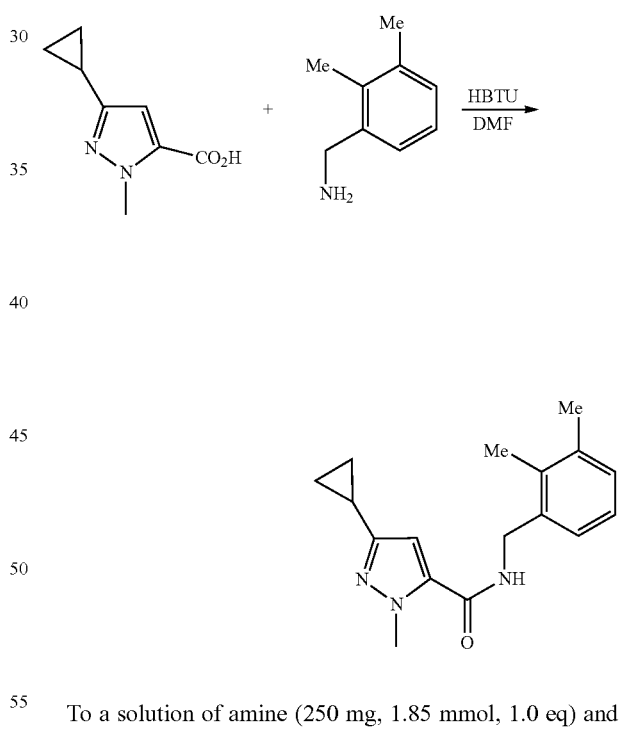

To a solution of amine (250 mg, 1.85 mmol, 1.0 eq) and acid (307 mg, 1.85 mmol, 1.0 eq) in DMF (15 mL) were added DIEA (1.19 g, 9.25 mmol, 5 eq) and HBTU (849 mg, 2.22 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product (270 mg). Mass Spectrum (LCMS, ESI Pos.) Calcd. For $C_{17}H_{22}N_3O$: 284 (M+H), Found 284.

21) 3-cyclopropyl-N-(2-(difluoromethoxy)-3-methylbenzyl)-1-methyl-1H-pyrazole-5-carboxamide

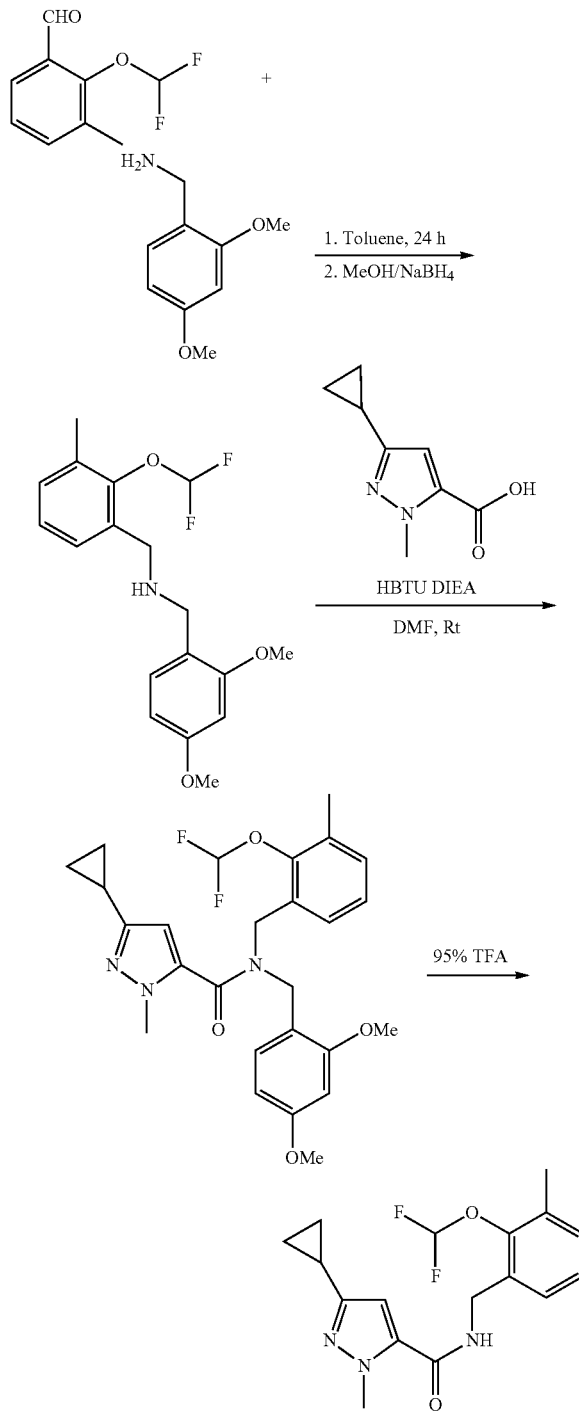

To a solution of aldehyde (253 mg, 1.36 mmol, 1.0 eq) in toluene (15 mL) was added 2,4-dimethoxybenzyl amine (227 mg, 1.36 mmol, 1.0 eq) and the reaction mixture was stirred at room temperature for 24 h. Toluene was removed to give a residue, which was taken in MeOH (15 mL) and then NaBH$_4$ (103 mg, 2.72 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (1.36 mmol, 1.0 eq) in DMF (15 mL) was added the acid (226 mg, 1.36 mmol, 1.0 eq), DIEA (877 mg, 1.30 mmol, 5 eq) and HBTU (618 mg, 1.63 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For C$_{17}$H$_{20}$F$_2$N$_3$O$_2$: 336.0 (M+H), Found 336.0.

22) 3-cyclopropyl-1-methyl-N-(2-methyl-3-(trifluoromethyl)benzyl)-1H-pyrazole-5-carboxamide

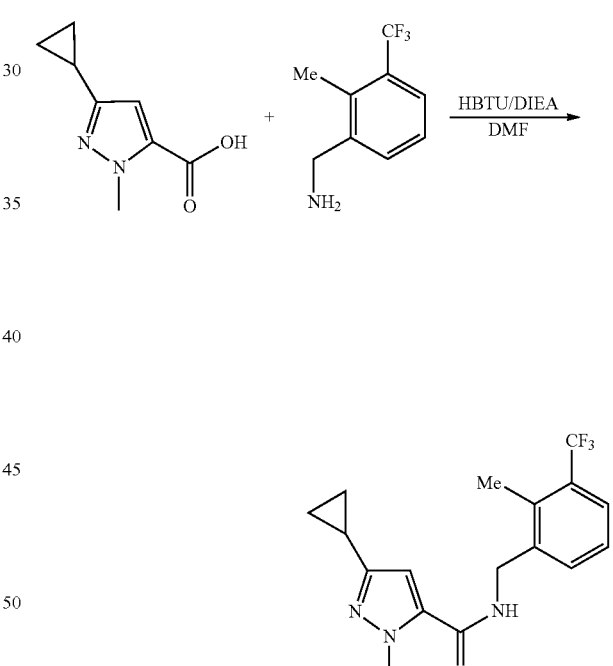

To a solution of amine (125 mg, 0.661 mmol, 1.0 eq) and acid (110 mg, 0.661 mmol, 1.0 eq) in DMF (10 mL) were added DIEA (427 mg, 3.31 mmol, 5 eq) and HBTU (300 mg, 0.794 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product. Mass Spectrum (LCMS, ESI Pos.) Calcd. For C$_{17}$H$_{19}$F$_3$N$_3$O: 338.0 (M+H), Found 338.0.

23) 3-isopropyl-1-methyl-N-(2-methyl-3-(trifluoromethyl)benzyl)-1H-pyrazole-5-carboxamide

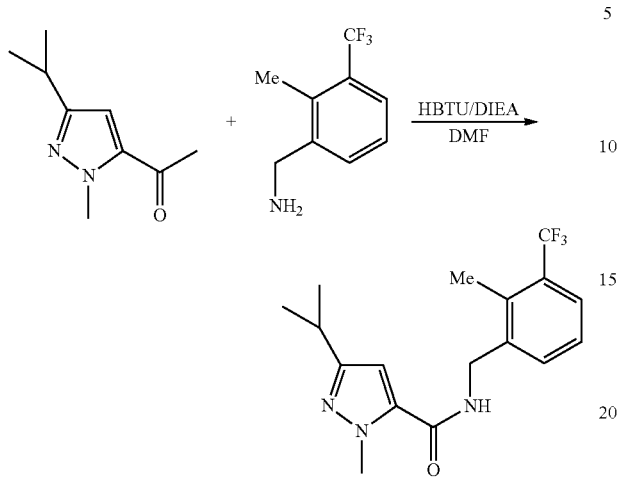

24) 3-cyclopropyl-N-(2-methoxy-3-(trifluoromethyl)benzyl)-1-methyl-1H-pyrazole-5-carboxamide

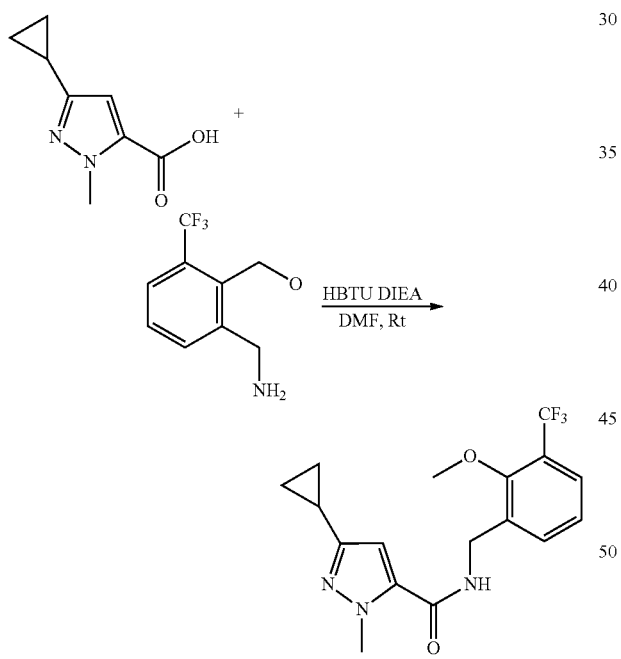

To a solution of amine (100 mg, 0.488 mmol, 1.0 eq) and acid (81 mg, 0.488 mmol, 1.0 eq) in DMF (5 mL) were added DIEA (315 mg, 2.44 mmol, 5 eq) and HBTU (222 mg, 0.586 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product (90 mg, >95% purity). Mass Spectrum (LCMS, ESI Pos.) Calcd. For $C_{17}H_{19}F_3N_3O_2$: 354.0 (M+H), Found 354.0.

25) 3-isopropyl-N-(2-methoxy-3-(trifluoromethyl)benzyl)-1-methyl-1H-pyrazole-5-carboxamide

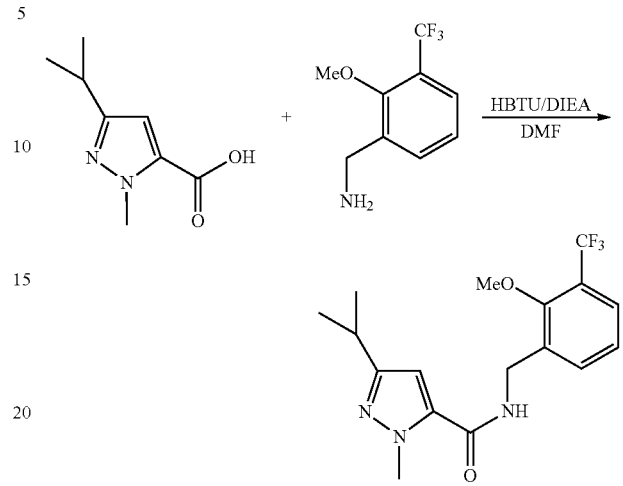

To a solution of amine (250 mg, 1.21 mmol, 1.0 eq) and acid (205 mg, 1.21 mmol, 1.0 eq) in DMF (15 mL) were added DIEA (780 mg, 6.0 mmol, 5 eq) and HBTU (550 mg, 1.45 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product. Mass Spectrum (LCMS, ESI Pos.) Calcd. For $C_{16}H_{16}F_4N_3O_2$: 356.0 (M+H), Found 356.0.

26) 3-cyclopropyl-N-(4-methoxy-3-(trifluoromethyl)benzyl)-1-methyl-1H-pyrazole-5-carboxamide

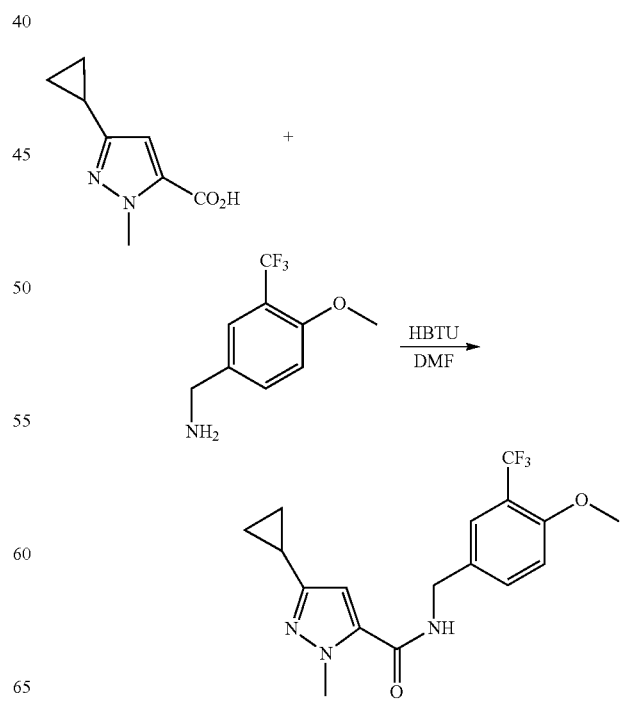

To a solution of amine (590 mg, 2.44 mmol, 1.0 eq) and acid (405 mg, 2.44 mmol, 1.0 eq) in DMF (15 mL) were added DIEA (1.57 g, 12.2 mmol, 5 eq) and HBTU (1.11 mg, 2.93 mmol, 1.2 eq) and the reaction mixture was stirred at rt for 12 h. The reaction mixture was then diluted with ethyl acetate (20 mL) and washed with 10% aq HCl (1×20 mL), sat NaHCO₃ (1×20 mL) and water (4×20 mL). Organic layer was collected, dried (MgSO₄) and evaporated to give a crude product, which was purified by column chromatography (EtOAc/Hexane 10% to 50%) to give the desired product. Mass Spectrum (LCMS, ESI Pos.) Calcd. For $C_{17}H_{19}F_3N_3O_2$: 354.0 (M+H), Found 354.0.

27) 3-(tert-butyl)-N-(3-methoxy-4-methylbenzyl)-1-methyl-1H-pyrazole-5-carboxamide

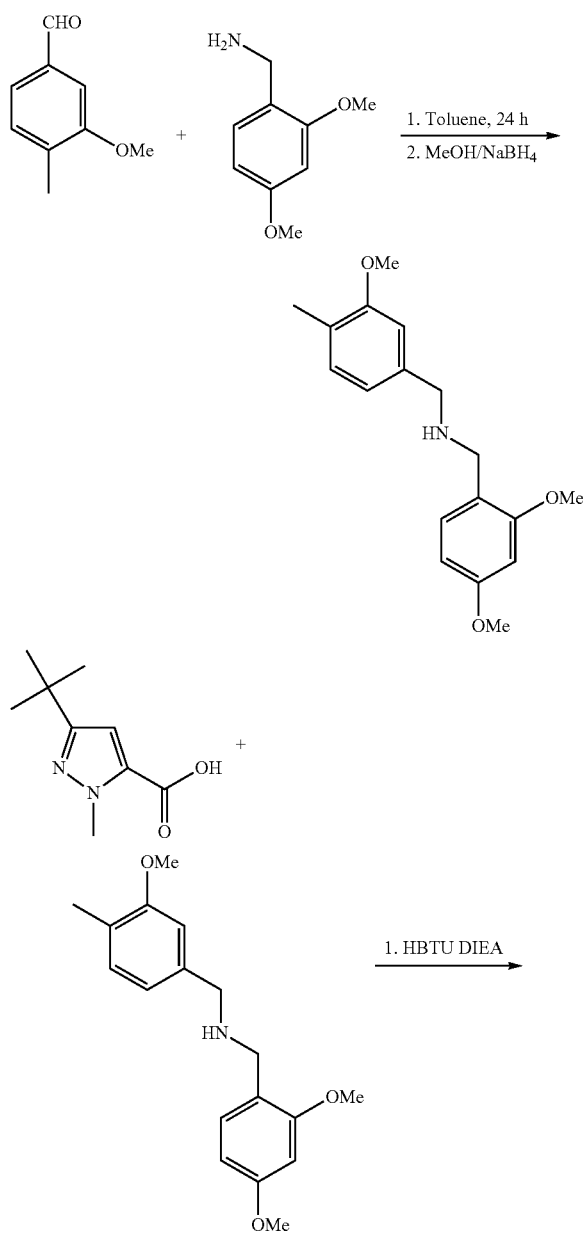

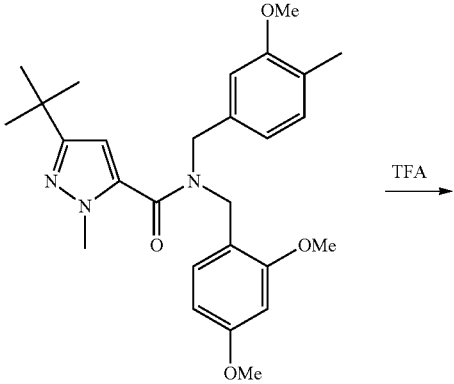

To a solution of 3-Methoxy-3-methyl-benzaldehyde (250 mg, 1.66 mmol, 1.0 eq) in toluene (20 mL) was added 2,4-dimethoxybenzyl amine (306 mg, 1.83 mmol, 1.1 eq) and the reaction mixture was stirred at room temperature for 24 h. Toluene was removed to give a residue, which was taken in MeOH (20 mL) and then NaBH₄ (129 mg, 3.32 mmol, 2.0 eq) was added slowly. The reaction mixture was stirred at room temperature for 6 h. Solvent was removed and the residue was extracted in Ethyl acetate and stirred with saturated aq NaHCO₃ for 1 h. The organic layer was collected, dried and solvent was removed to give the crude amine, which was used in the next step without further purification. To a solution of the crude amine (1.66 mmol, 1.0 eq) in DMF (20 mL) were added the acid (333 mg, 1.83 mmol, 1.1 eq), DIEA (1.07 g, 8.32 mmol, 5 eq) and HBTU (757 g, 1.99 mmol, 1.2 eq) and the reaction mixture was stirred at rt for 12 h. The reaction mixture was then diluted with ethyl acetate (75 mL) and washed with 10% aqHCl (1×50 mL), sat NaHCO₃ (1×50 mL) and water (4×50 mL). Organic layer was collected, dried (MgSO₄) and evaporated to give a crude product, which was purified by column chromatography (EtOAc/Hexane 25% to 75%)) to give the amide, which was directly used in the next step. The amide was treated with 95% TFA:H₂O for 12 h. TFA was removed and azeotroped with toluene to give a residue, which was purified by column chromatography (EtOAc/Hexane 10% to 50%) to give the desired product in (263 mg, >95% purity). Mass Spectrum (LCMS, ESI Pos.) Calcd. For $C_{18}H_{26}N_3O_2$: 316.0 (M+H), Found 316.0.

28) 3-cyclopropyl-N-(3-methoxy-2-methylbenzyl)-1-methyl-1H-pyrazole-5-carboxamide

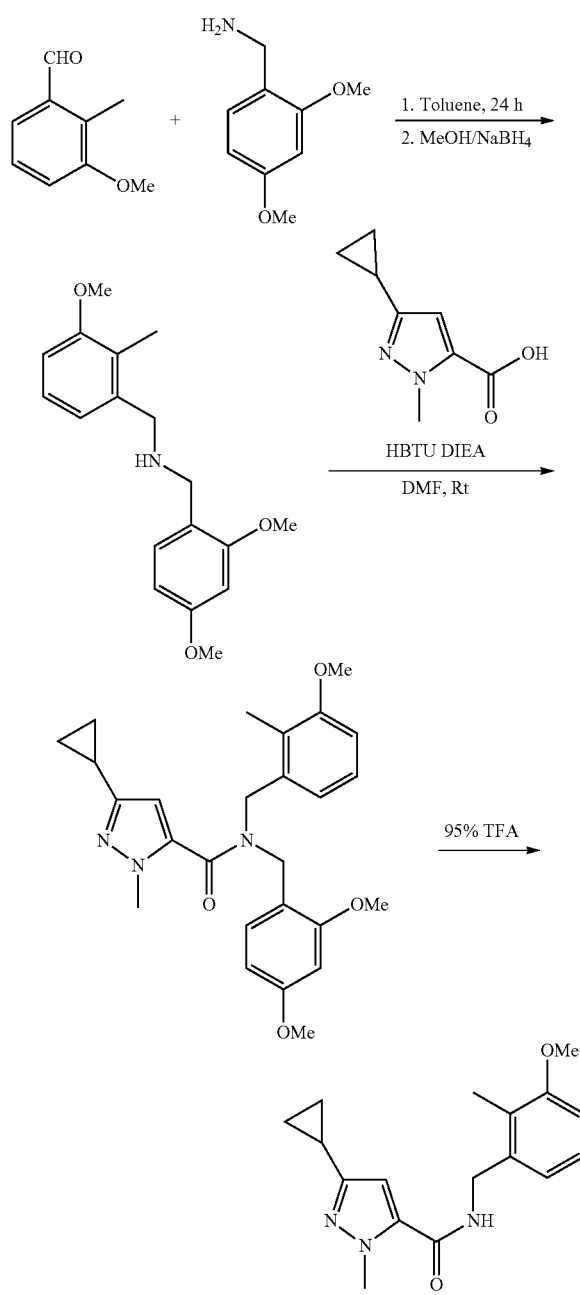

To a solution of aldehyde (1.0 g, 6.66 mmol, 1.0 eq) in toluene (20 mL) was added 2,4-dimethoxybenzyl amine (1.23 g, 7.33 mmol, 1.1 eq) and the reaction mixture was stirred at room temperature for 24 h. Toluene was removed to give a residue, which was taken in MeOH (25 mL) and then NaBH$_4$ (506 mg, 13.32 mmol, 2.0 eq) was added slowly. The reaction mixture was stirred at room temperature for 6 h. Solvent was removed and the residue was extracted in ethyl acetate and stirred with saturated aq NaHCO$_3$ for 1 h. The organic layer was collected, dried and solvent was removed to give the crude amine, which was used in the next step without further purification. To a solution of the crude amine (4.44 mmol, 1.0 eq) in DMF (15 mL) was added the acid (737 mg, 4.44 mmol, 1.0 eq), DIEA (2.86 g, 22.2 mmol, 5 eq) and HBTU (2.02 g, 5.38 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product (80 mg, >95% purity). Mass Spectrum (LCMS, ESI Pos.) Calcd. For C$_{17}$H$_{22}$N$_3$O$_2$: 300.0 (M+H), Found 300.0.

29) 3-isopropyl-N-(3-methoxy-2-methylbenzyl)-1-methyl-1H-pyrazole-5-carboxamide

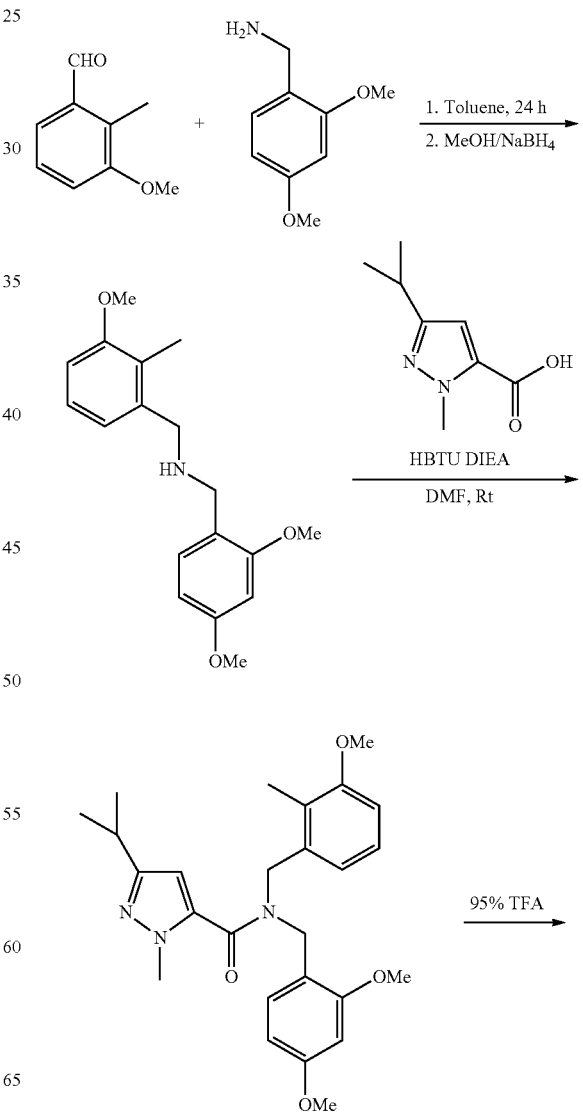

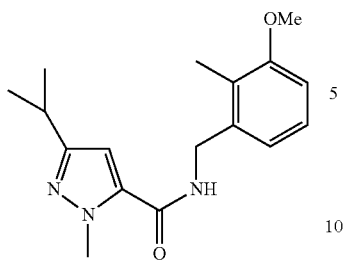

To a solution of aldehyde (1.0 g, 6.66 mmol, 1.0 eq) in toluene (20 mL) was added 2,4-dimethoxybenzyl amine (1.23 g, 7.33 mmol, 1.1 eq) and the reaction mixture was stirred at room temperature for 24 h. Toluene was removed to give a residue, which was taken in MeOH (25 mL) and then NaBH$_4$ (506 mg, 13.32 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (2.22 mmol, 1.0 eq) in DMF (15 mL) was added the acid (372 mg, 2.22 mmol, 1.0 eq), DIEA (1.98 g, 11.11 mmol, 5 eq) and HBTU 1.01 g, 2.66 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product (80 mg, >95% purity). Mass Spectrum (LCMS, ESI Pos.) Calcd. For C$_{47}$H$_{24}$N$_3$O$_2$: 302.0 (M+H), Found 302.0.

30) 3-cyclopropyl-N-(3-methoxy-2-(trifluoromethyl)benzyl)-1-methyl-1H-pyrazole-5-carboxamide

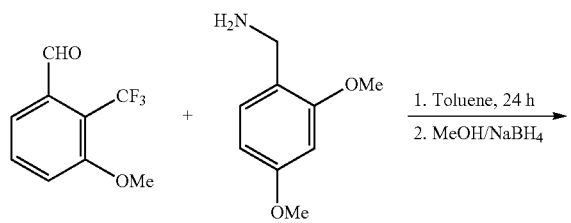

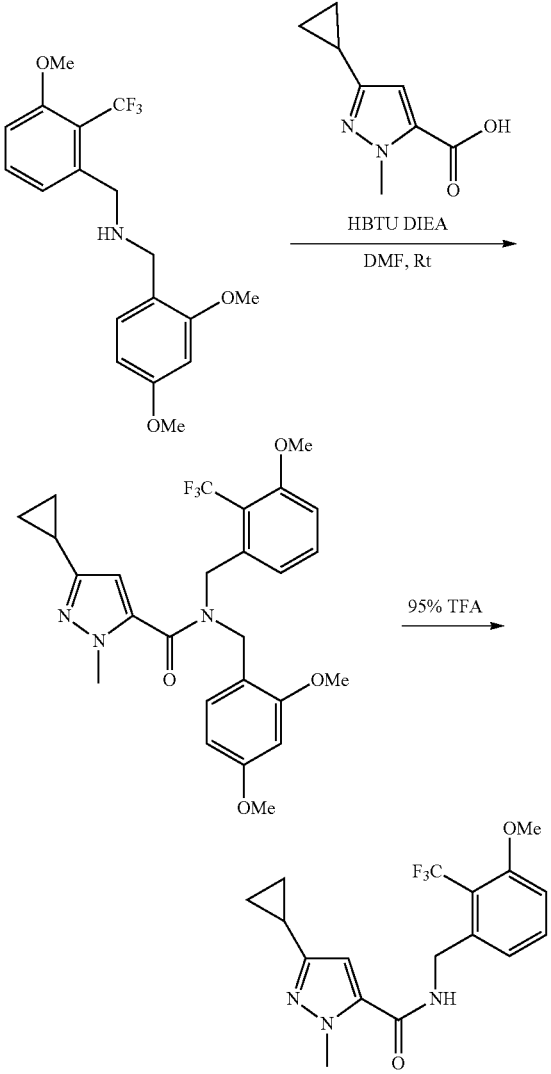

To a solution of aldehyde (1.0 g, 4.90 mmol, 1.0 eq) in toluene (25 mL) was added 2,4-dimethoxybenzyl amine (900 mg, 5.39 mmol, 1.10 eq) and the reaction mixture was stirred at room temperature for 24 h. Toluene was removed to give a residue, which was taken in MeOH (25 mL) and then NaBH$_4$ (372 mg, 9.86 mmol, 2.0 eq) was added slowly. The reaction mixture was stirred at room temperature for 6 h. Solvent was removed and the residue was extracted in ethyl acetate and stirred with saturated aq NaHCO$_3$ for 1 h. The organic layer was collected, dried and solvent was removed to give the crude amine, which was used in the next step without further purification.

To a solution of the crude amine (3.68 mmol, 1.0 eq) in DMF (15 mL) was added the acid (610 mg, 3.68 mmol, 1.0 eq), DIEA (2.37 g, 16.4 mmol, 5 eq) and HBTU (1.67 g, 4.41 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For $C_{17}H_{19}F_3N_3O_2$: 354.0 (M+H), Found 354.0.

31) 3-(tert-butyl)-N-(2-hydroxy-3-methoxybenzyl)-1-methyl-1H-pyrazole-5-carboxamide

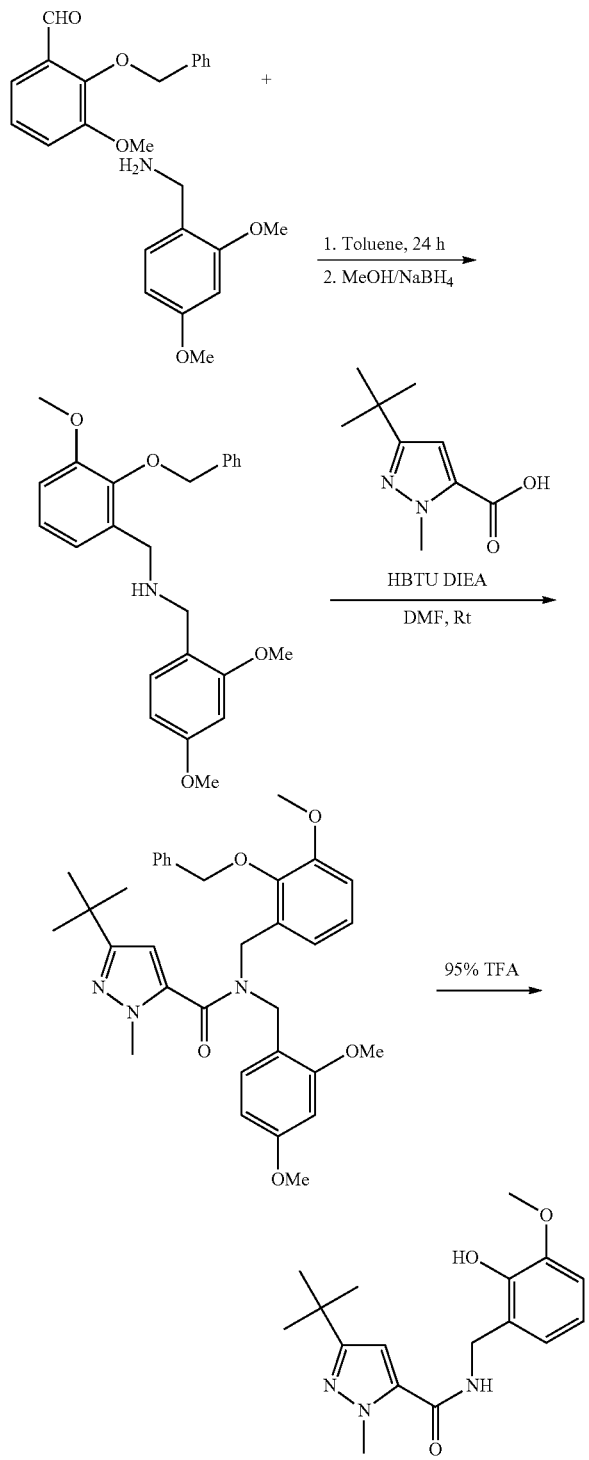

To a solution of aldehyde (500 mg, 2.07 mmol, 1.0 eq) in toluene (15 mL) was added 2,4-dimethoxybenzyl amine (345 mg, 2.07 mmol, 1.0 eq) and the reaction mixture was stirred at room temperature for 24 h. Toluene was removed to give a residue, which was taken in MeOH (15 mL) and then NaBH$_4$ (157 mg, 4.14 mmol, 2.0 eq) was added slowly. The reaction mixture was stirred at room temperature for 6 h. Solvent was removed and the residue was extracted in ethyl acetate and stirred with saturated aq NaHCO$_3$ for 1 h. The organic layer was collected, dried and solvent was removed to give the crude amine, which was used in the next step without further purification. To a solution of the crude amine (0.509 mmol, 1.1 eq) in DMF (10 mL) were added the acid (84 mg, 0.463 mmol, 1.0 eq), DIEA (300 mg, 2.32 mmol, 5 eq) and HBTU (211 mg, 0.56 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product in low yield. Mass Spectrum (LCMS, ESI Pos.) Calcd. For $C_{17}H_{24}N_3O_3$: 318.0 (M+H), Found 318.0.

32) N-(2,3-dimethoxybenzyl)-3-isopropyl-1-methyl-1H-pyrazole-5-carboxamide

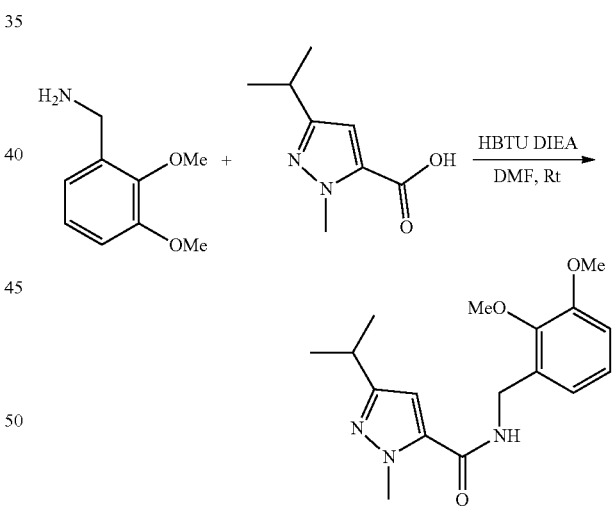

To a solution of the amine (365 mg, 2.17 mmol, 1.0 eq) in DMF (20 mL) were added the acid (365 mg, 2.17 mmol, 1.0 eq), DIEA (1.40 g, 10.85 mmol, 5 eq) and HBTU (987 mg, 2.86 mmol, 1.2 eq) and the reaction mixture was stirred at rt for 12 h. The reaction mixture was then diluted with ethyl acetate (75 mL) and washed with 10% aq HCl (1×50 mL), sat NaHCO$_3$ (1×50 mL) and water (4×50 mL). Organic layer was collected, dried (MgSO$_4$) and evaporated to give a crude product, which was purified by column chromatography (EtOAc/Hexane 10% to 50%) to give the desired product. Mass Spectrum (LCMS, ESI Pos.) Calcd. For $C_{17}H_{24}N_3O_3$: 318.0 (M+H), Found 318.0.

33) 3-cyclopropyl-N-(3-methoxy-2-propoxybenzyl)-1-methyl-1H-pyrazole-5-carboxamide

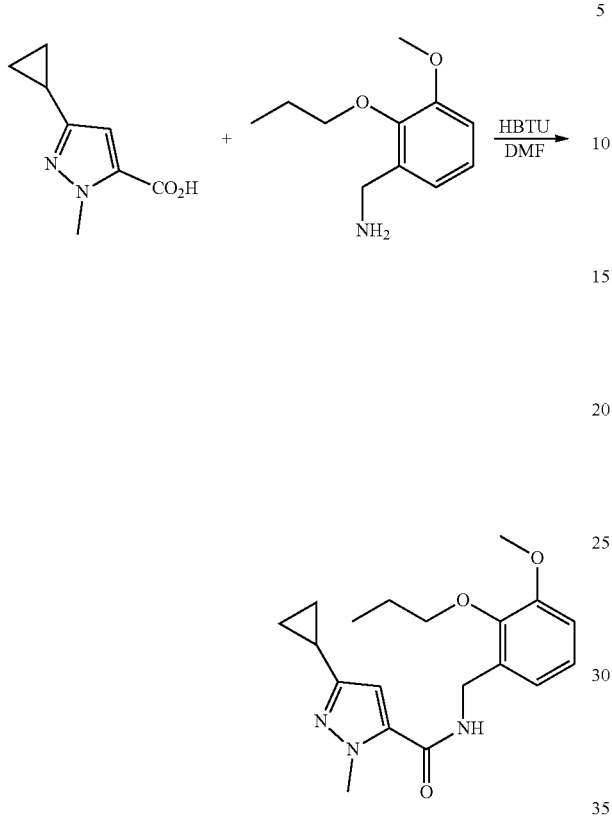

To a solution of amine (250 mg, 1.082 mmol, 1.0 eq) and acid (181 mg, 1.082 mmol, 1.0 eq) in DMF (10 mL) were added DIEA (697 mg, 5.40 mmol, 5 eq) and HBTU (491 mg, 1.296 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product. Mass Spectrum (LCMS, ESI Pos.) Calcd. For C$_{19}$H$_{26}$N$_3$O$_3$: 344.0 (M+H), Found 344.0.

34) 3-(tert-butyl)-N-(2-hydroxy-3-(trifluoromethoxy)benzyl)-1-methyl-1H-pyrazole-5-carboxamide

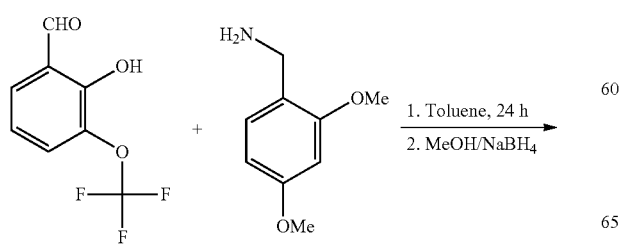

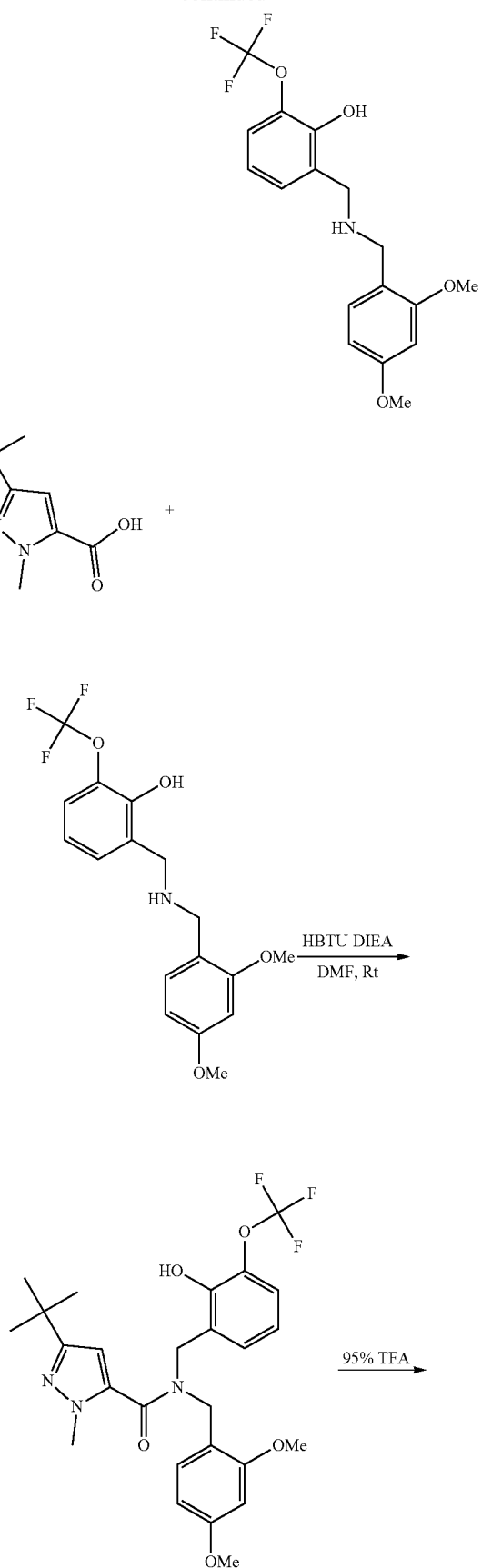

-continued

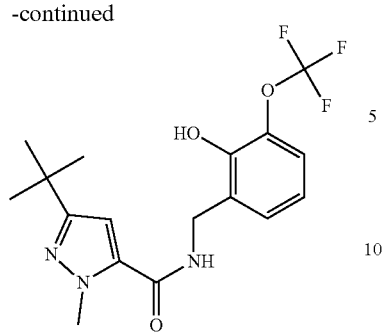

To a solution of aldehyde (250 mg, 1.21 mmol, 1.0 eq) in toluene (20 mL) was added 2,4-dimethoxybenzyl amine (223 mg, 1.33 mmol, 1.1 eq) and the reaction mixture was stirred at room temperature for 24 h. Toluene was removed to give a residue, which was taken in MeOH (30 mL) and then NaBH$_4$ (86 mg, 2.42 mmol, 2.0 eq) was added slowly. The reaction mixture was stirred at room temperature for 6 h. Solvent was removed and the residue was extracted in ethyl acetate and stirred with saturated aq NaHCO$_3$ for 1 h. The organic layer was collected, dried and solvent was removed to give the crude amine, which was used in the next step without further purification. To a solution of the crude amine (1.21 mmol, 1.0 eq) in DMF (10 mL) was added the acid (242 mg, 1.33 mmol, 1.1 eq), DIEA (780 mg, 6.05 mmol, 5 eq) and HBTU (550 mg, 1.45 mmol, 1.2 eq) and the reaction mixture was stirred at rt for 12 h. The reaction mixture was then diluted with Ethyl acetate (200 mL) and washed with 10% aqHCl (1×50 mL), sat NaHCO$_3$ (1×50 mL) and water (4×50 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product in 28% (126 mg, >95% purity). Mass Spectrum (LCMS, ESI Pos.) Calcd. For C$_{17}$H$_{21}$F$_3$N$_3$O$_3$: 372.0 (M+H), Found 372.0.

35) 3-(tert-butyl)-N-(2-methoxy-3-(trifluoromethoxy)benzyl)-1-methyl-1H-pyrazole-5-carboxamide

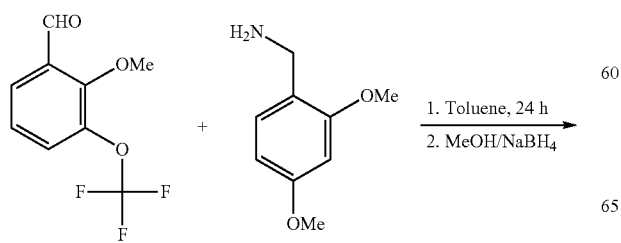

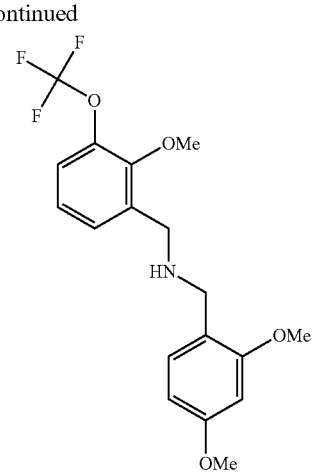

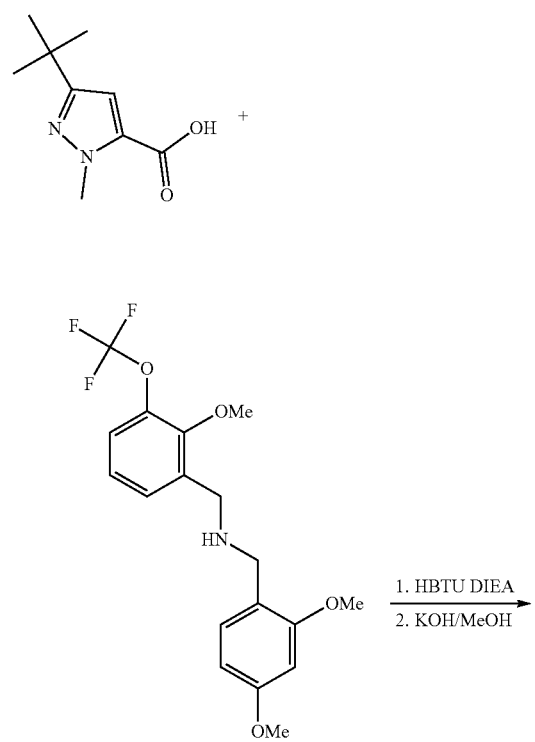

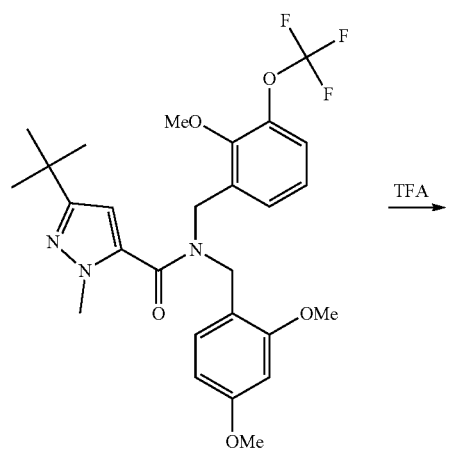

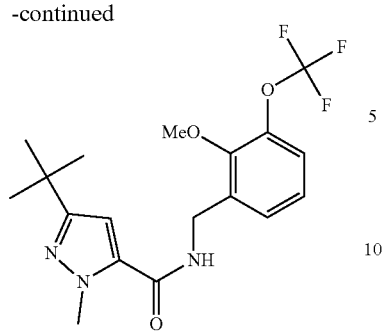

To a solution of 2-Methoxy-3-trifluoromethoxy-benzaldehyde (9.71 mmol, 1.0 eq) in toluene (20 mL) was added 2,4-dimethoxybenzyl amine (1.78 g, 10.68 mmol, 1.1 eq) and the reaction mixture was stirred at room temperature for 24 h. Toluene was removed to give a residue, which was taken in MeOH (20 mL) and then NaBH₄ (735 mg, 19.42 mmol, 2.0 eq) was added slowly. The reaction mixture was stirred at room temperature for 6 h. Solvent was removed and the residue was extracted in ethyl acetate and stirred with saturated aq NaHCO₃ for 1 h. The organic layer was collected, dried and solvent was removed to give the crude amine, which was used in the next step without further purification. To a solution of the crude amine (4.86 mmol, 1.0 eq) in DMF (20 mL) was added the acid (930 mg, 5.35 mmol, 1.1 eq), DIEA (3.13 g, 24.3 mmol, 5 eq) and HBTU (2.22 g, 5.83 mmol, 1.2 eq) and the reaction mixture was stirred at rt for 12 h. The reaction mixture was then diluted with ethyl acetate (75 mL) and washed with 10% aqHCl (1×50 mL), sat NaHCO₃ (1×50 mL) and water (4×50 mL). Organic layer was collected, dried (MgSO₄) and evaporated to give a crude product, which was purified by column chromatography (EtOAc/Hexane 25% to 75%)) to give the amide, which was directly used in the next step. The amide was treated with 95% TFA:H₂O for 12 h. TFA was removed and azeotroped with toluene to give a residue, which was purified by column chromatography (EtOAc/Hexane 10% to 50%) to give the desired product in (754 mg, >95% purity). Mass Spectrum (LCMS, ESI Pos.) Calcd. For $C_{18}H_{23}F_3N_3O_3$: 386.0 (M+H), Found 386.0.

36) 3-cyclopropyl-N-(2-methoxy-3-(trifluoromethoxy)benzyl)-1-methyl-1H-pyrazole-5-carboxamide

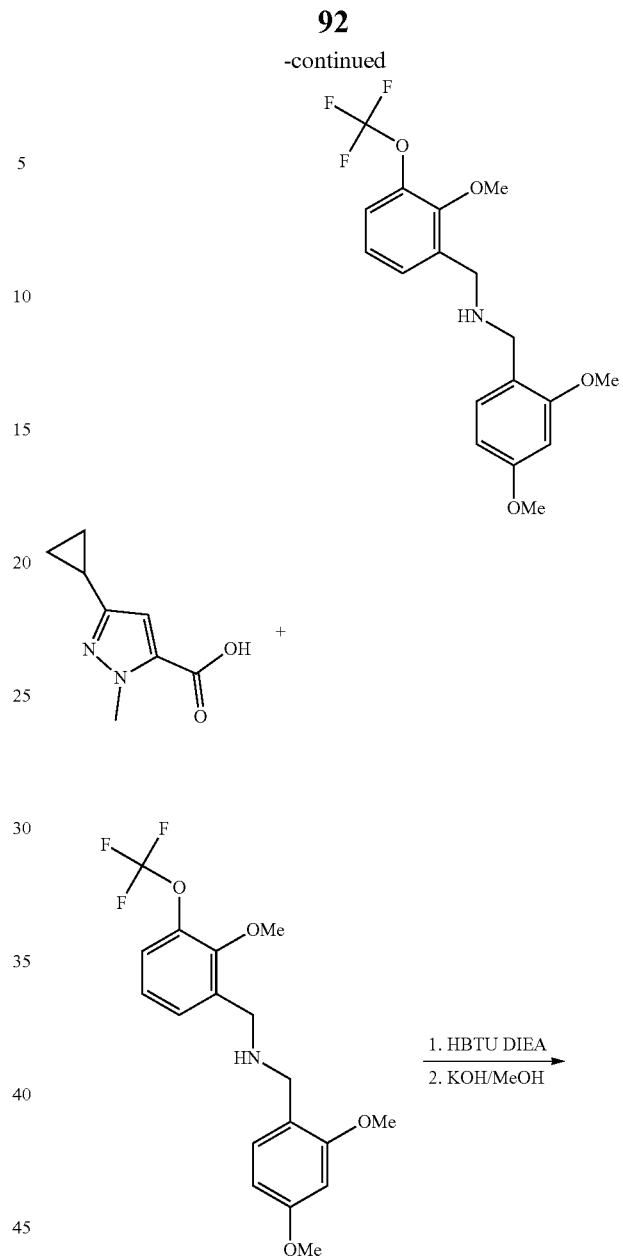

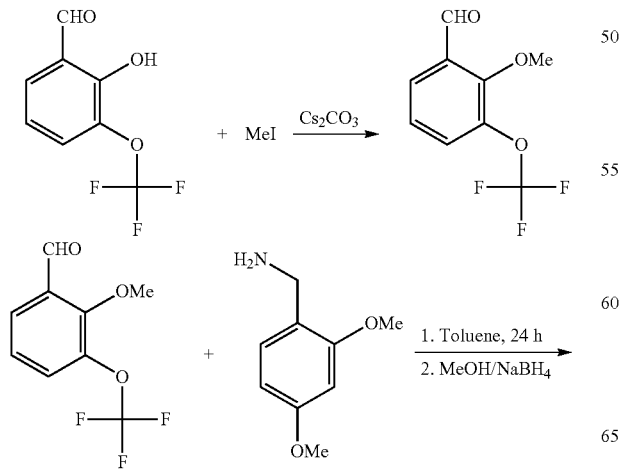

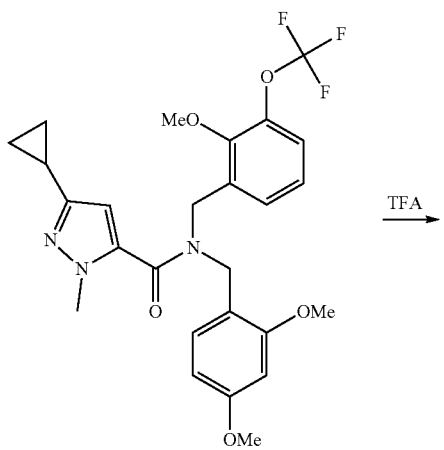

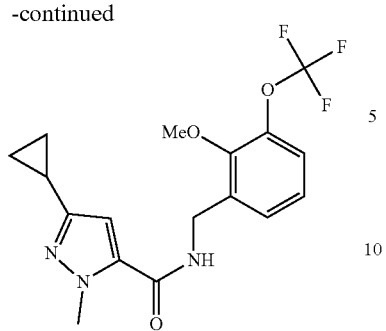

Preparation of 2-Methoxy-3-trifluoromethoxy-benzaldehyde: To a solution of 2-hydroxy-3-trifluoromethoxybenzaldehyde (2.0 g, 9.71 mmol, 1 eq) in DMF (20 mL) was added cesium carbonate (4.73 g, 14.56 mmol, 1.5 eq) and the reaction mixture was stirred at rt for 15 min. Then MeI (6.85 g, 48.55 mmol, 5 eq) was added and the reaction mixture was stirred at 50° C. for 24 h. Diluted with ethyl acetate and the reaction mixture was washed with water (4×). The organic layer was dried and evaporated to provide crude 2-Methoxy-3-trifluoromethoxy-benzaldehyde (2.48 g), which was used without further purification.

To a solution of 2-Methoxy-3-trifluoromethoxy-benzaldehyde (9.71 mmol, 1.0 eq) in toluene (20 mL) was added 2,4-dimethoxybenzyl amine (1.78 g, 10.68 mmol, 1.1 eq) and the reaction mixture was stirred at room temperature for 24 h. Toluene was removed to give a residue, which was taken in MeOH (20 mL) and then NaBH₄ (735 mg, 19.42 mmol, 2.0 eq) was added slowly. The reaction mixture was stirred at room temperature for 6 h. Solvent was removed and the residue was extracted in ethyl acetate and stirred with saturated aq NaHCO₃ for 1 h. The organic layer was collected, dried and solvent was removed to give the crude amine, which was used in the next step without further purification. To a solution of the crude amine (4.86 mmol, 1.0 eq) in DMF (20 mL) were added the acid (888 mg, 5.35 mmol, 1.1 eq), DIEA (3.13 g, 24.3 mmol, 5 eq) and HBTU (2.22 g, 5.83 mmol, 1.2 eq) and the reaction mixture was stirred at rt for 12 h. The reaction mixture was then diluted with ethyl acetate (75 mL) and washed with 10% aqHCl (1×50 mL), sat NaHCO₃ (1×50 mL) and water (4×50 mL). Organic layer was collected, dried (MgSO₄) and evaporated to give a crude product, which was purified by column chromatography (EtOAc/Hexane 25% to 75%)) to give the amide, which was directly used in the next step. The amide was treated with 95% TFA:H₂O for 12 h. TFA was removed and azeotroped with toluene to give a residue, which was purified by column chromatography (EtOAc/Hexane 10% to 50%) to give the desired product in (985 mg, >95% purity). Mass Spectrum (LCMS, ESI Pos.) Calcd. For $C_{17}H_{19}F_3N_3O_3$: 370.0 (M+H), Found 370.0.

37) 3-(tert-butyl)-N-(2-(difluoromethoxy)-3-ethoxy-benzyl)-1-methyl-1H-pyrazole-5-carboxamide

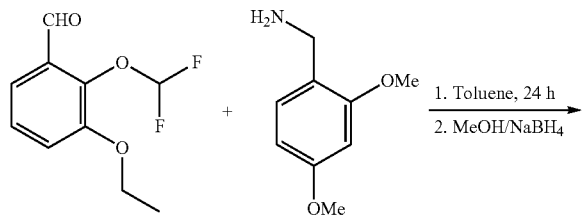

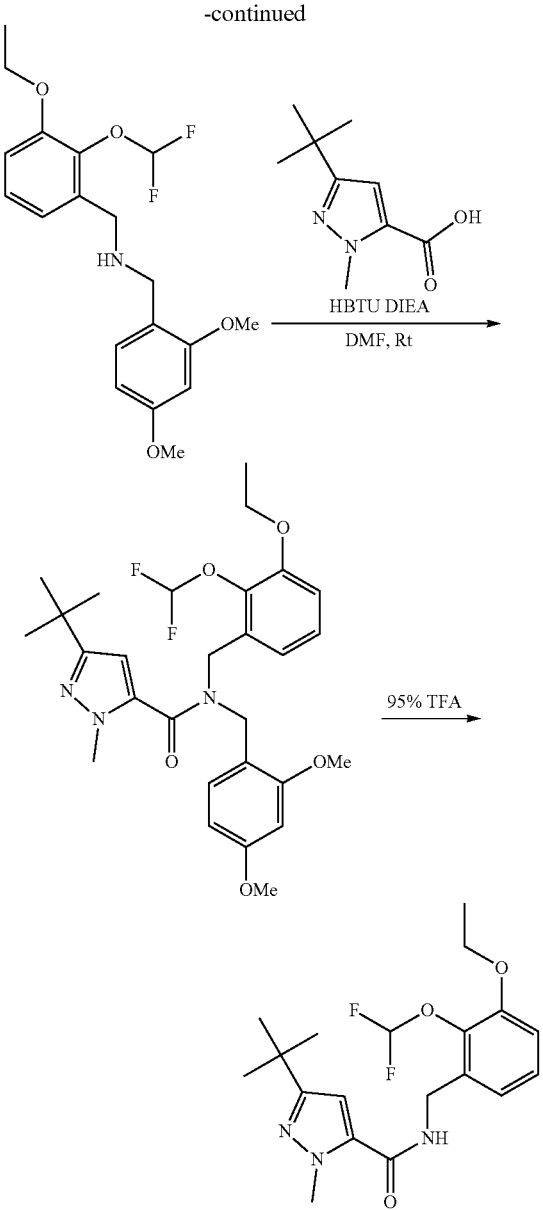

To a solution of aldehyde (250 mg, 1.16 mmol, 1.0 eq) in toluene (10 mL) was added 2,4-dimethoxybenzyl amine (193 mg, 1.16 mmol, 1.0 eq) and the reaction mixture was stirred at room temperature for 24 h. Toluene was removed to give a residue, which was taken in MeOH (15 mL) and then NaBH₄ (88 mg, 2.32 mmol, 2.0 eq) was added slowly. The reaction mixture was stirred at room temperature for 6 h. Solvent was removed and the residue was extracted in Ethyl acetate and stirred with saturated aq NaHCO₃ for 1 h. The organic layer was collected, dried and solvent was removed to give the crude amine, which was used in the next step without further purification. To a solution of the crude amine (1.16 mmol, 1.2 eq) in DMF (10 mL) were added the acid (176 mg, 0.98 mmol, 1.0 eq), DIEA (500 mg, 3.87 mmol, 4 eq) and HBTU (440 mg, 1.16 mmol, 1.2 eq) and the reaction mixture was stirred at rt for 12 h. The reaction mixture was then diluted with ethyl acetate (20 mL) and washed with 10% aq HCl (1×20 mL), sat NaHCO₃ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product (176 mg). Mass Spectrum (LCMS, ESI Pos.) Calcd. For C$_{19}$H$_{26}$F$_2$N$_3$O$_3$: 382.0 (M+H), Found 382.0.

38) 3-cyclopropyl-N-(2-(difluoromethoxy)-3-ethoxybenzyl)-1-methyl-1H-pyrazole-5-carboxamide

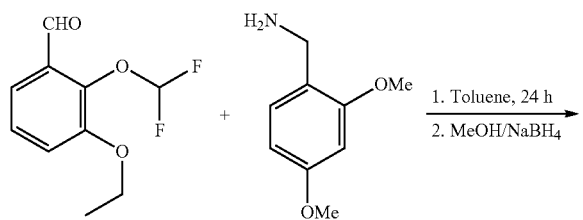

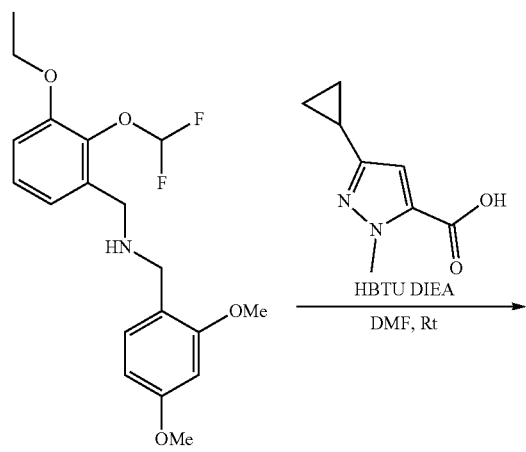

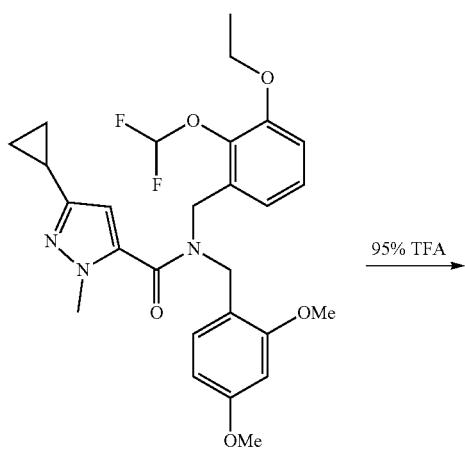

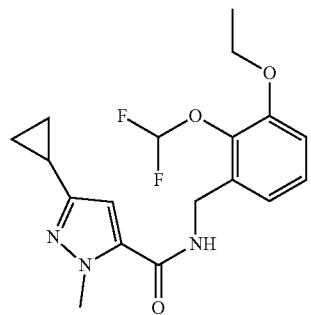

To a solution of aldehyde (1.0 g, 4.63 mmol, 1.0 eq) in toluene (25 mL) was added 2,4-dimethoxybenzyl amine (774 mg, 4.63 mmol, 1.0 eq) and the reaction mixture was stirred at room temperature for 24 h. Toluene was removed to give a residue, which was taken in MeOH (25 mL) and then NaBH$_4$ (350 mg, 9.26 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (2.32 mmol, 1.0 eq) in DMF (15 mL) was added the acid (385 mg, 2.32 mmol, 1.0 eq), DIEA (1.50 g, 11.6 mmol, 5 eq) and HBTU (1.1 g, 2.8 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For C$_{18}$H$_{22}$F$_2$N$_3$O$_3$: 366.0 (M+H), Found 366.0.

39) N-(3-(cyclopentylmethoxy)-2-methoxybenzyl)-3-cyclopropyl-1-methyl-1H-pyrazole-5-carboxamide

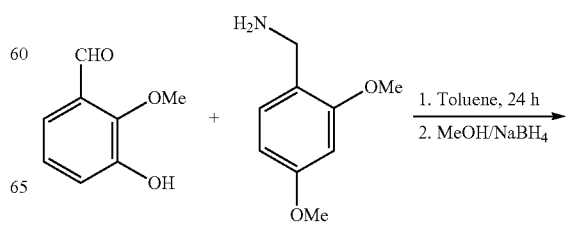

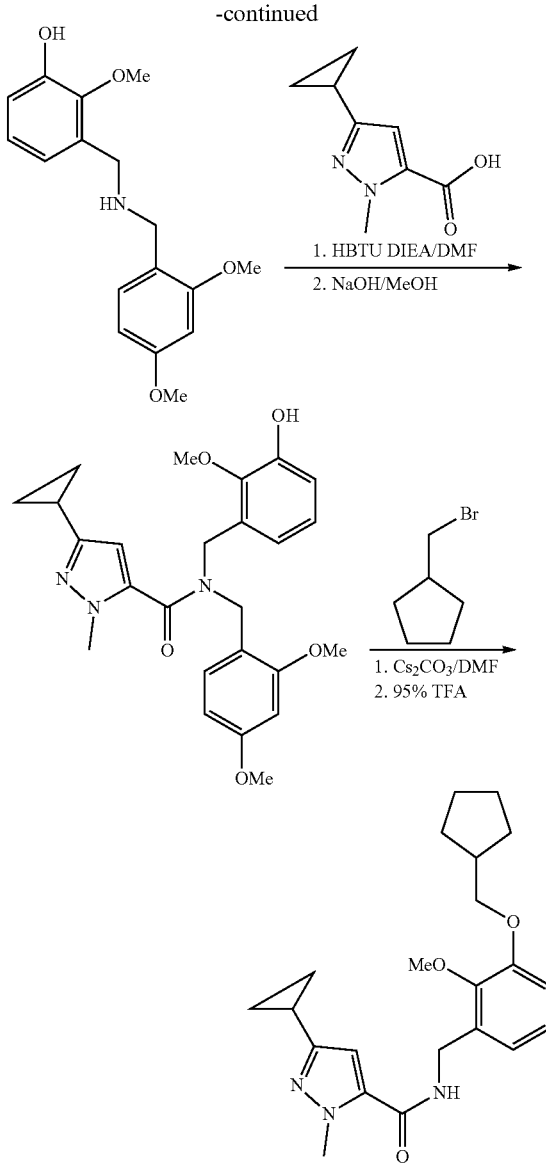

To a solution of aldehyde (10.0 g, 65.79 mmol, 1.0 eq) in toluene (100 mL) was added 2,4-dimethoxybenzyl amine (10.89 g, 65.79 mmol, 1.0 eq) and the reaction mixture was stirred at room temperature for 24 h. Toluene was removed to give a residue, which was taken in MeOH (100 mL) and then NaBH$_4$ (4.97 g, 131.58 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (7.26 mmol, 1.0 eq) in DMF (20 mL) was added the acid (1.21 g, 7.26 mmol, 1.0 eq), DIEA (4.68 g, 36.30 mmol, 5 eq) and HBTU (3.30 g, 8.71 mmol, 1.2 eq) and the reaction mixture was stirred at rt for 12 h. The reaction mixture was then diluted with ethyl acetate (100 mL) and washed with 10% aq HCl (1×50 mL), sat NaHCO$_3$ (1×50 mL) and water (4×50 mL). Organic layer was collected, dried (MgSO$_4$) and evaporated to give a crude product, which was taken in 150 mL of methanol and NaOH (290 mg, 7.26 mmol, 1.0 eq) was added and stirred at room temperature for 24 h. Methanol was removed and the residue was neutralized with 10% aq HCl. The reaction mixture was then extracted with ethyl acetate (2×). Organic layer was collected, dried (MgSO$_4$) and evaporated to give a crude product, which was purified by column chromatography (EtOAc/Hexane) to give the amide.

To a solution of the hydroxy amide (500 mg, 1.07 mmol, 1.0 eq) in DMF (15 mL) was added Cs$_2$CO$_3$ (1.04 g, 3.21 mmol, 3.0 eq) and stirred at room temperature for 20 min. Then bromide (261 mg, 1.60 mmol, 1.5 eq) was added and stirred at rt for 24 h. The reaction mixture was then diluted with ethyl acetate (25 mL) and washed with water (4×). Organic layer was collected, dried (MgSO$_4$) and evaporated to give a residue, which was then treated with 95% TFA:H$_2$O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For C$_{12}$H$_{30}$N$_2$O$_3$: 384.0 (M+H), Found 362.0.

40) N-(4-(difluoromethoxy)-3,5-dimethylbenzyl)-3-isopropyl-1-methyl-1H-pyrazole-5-carboxamide

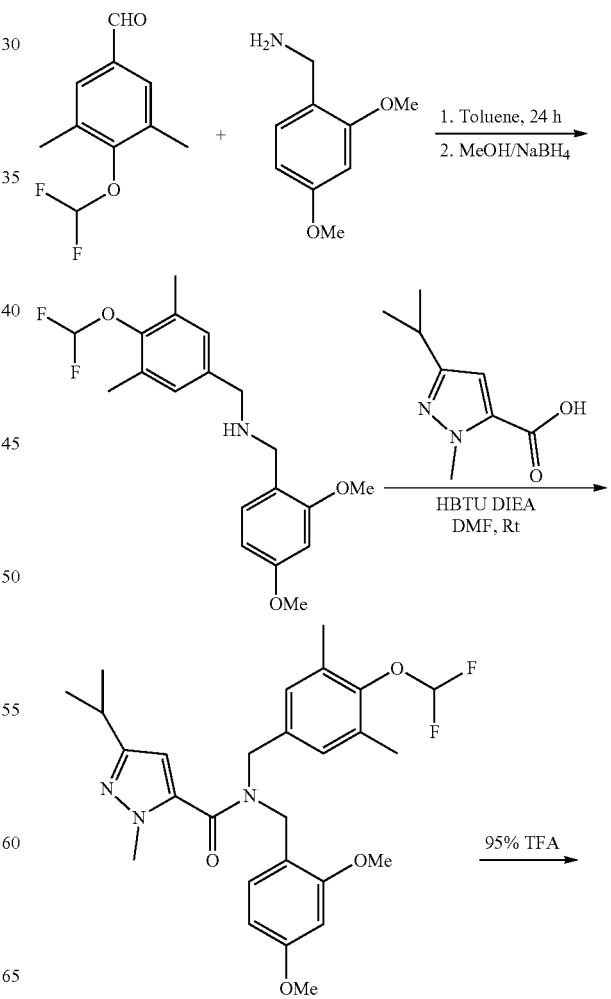

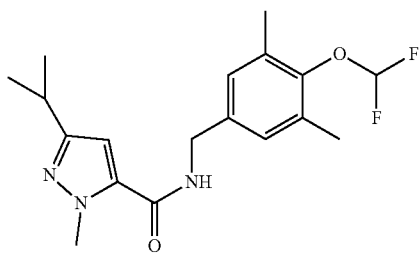

To a solution of aldehyde (250 mg, 1.25 mmol, 1.0 eq) in toluene (20 mL) was added 2,4-dimethoxybenzyl amine (208 mg, 1.25 mmol, 1.0 eq) and the reaction mixture was stirred at room temperature for 24 h. Toluene was removed to give a residue, which was taken in MeOH (20 mL) and then NaBH$_4$ (95 mg, 2.50 mmol, 2.0 eq) was added slowly. The reaction mixture was stirred at room temperature for 6 h. Solvent was removed and the residue was extracted in ethyl acetate and stirred with saturated aq NaHCO$_3$ for 1 h. The organic layer was collected, dried and solvent was removed to give the crude amine, which was used in the next step without further purification. To a solution of the crude amine (1.25 mmol, 1.0 eq) in DMF (15 mL) was added the acid (210 mg, 1.25 mmol, 1.0 eq), DIEA (806 mg, 6.25 mmol, 5 eq) and HBTU (569 mg, 1.50 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product (87 mg, >95% purity). Mass Spectrum (LCMS, ESI Pos.) Calcd. For C$_{18}$H$_{24}$F$_2$N$_3$O$_2$: 352.0 (M+H), Found 352.0.

41) N-(3-bromo-4-ethoxy-5-methoxybenzyl)-3-cyclopropyl-1-methyl-1H-pyrazole-5-carboxamide

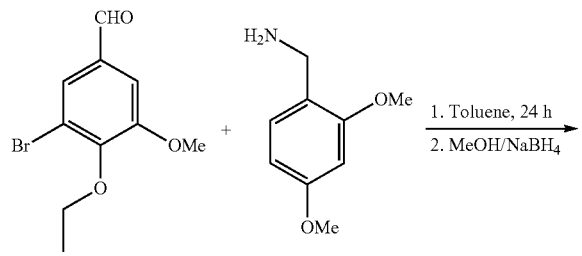

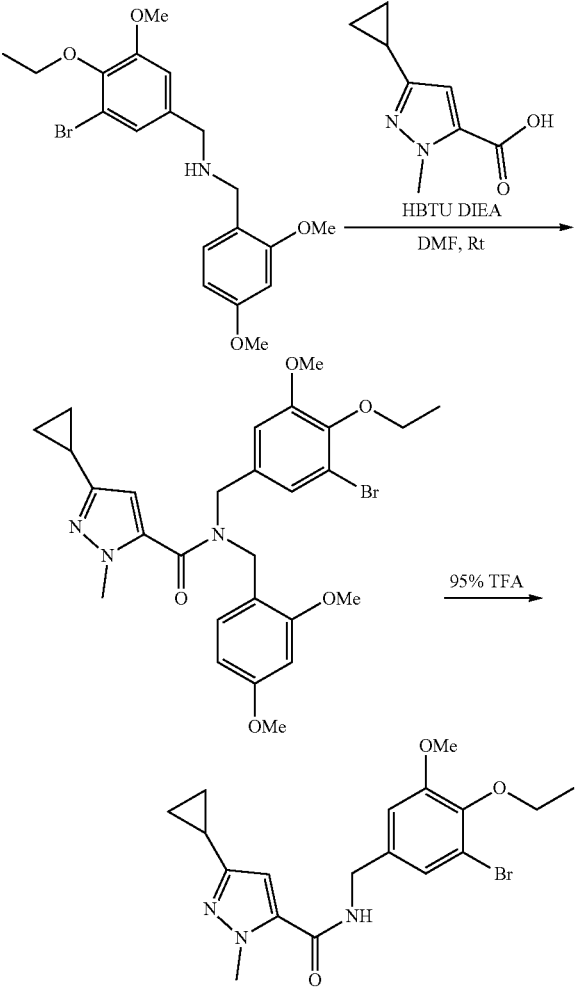

To a solution of aldehyde (1.0 g, 3.86 mmol, 1.0 eq) in toluene (25 mL) was added 2,4-dimethoxybenzyl amine (645 mg, 3.86 mmol, 1.0 eq) and the reaction mixture was stirred at room temperature for 24 h. Toluene was removed to give a residue, which was taken in MeOH (25 mL) and then NaBH$_4$ (292 mg, 7.72 mmol, 2.0 eq) was added slowly. The reaction mixture was stirred at room temperature for 6 h. Solvent was removed and the residue was extracted in ethyl acetate and stirred with saturated aq NaHCO$_3$ for 1 h. The organic layer was collected, dried and solvent was removed to give the crude amine, which was used in the next step without further purification. To a solution of the crude amine (1.93 mmol, 1.0 eq) in DMF (15 mL) was added the acid (323 mg, 1.93 mmol, 1.0 eq), DIEA (1.25 g, 9.65 mmol, 5 eq) and HBTU (877 mg, 2.32 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the

42) N-(3-chloro-4-propoxy-5-methoxybenzyl)-3-isopropyl-1-methyl-1H-pyrazole-5-carboxamide

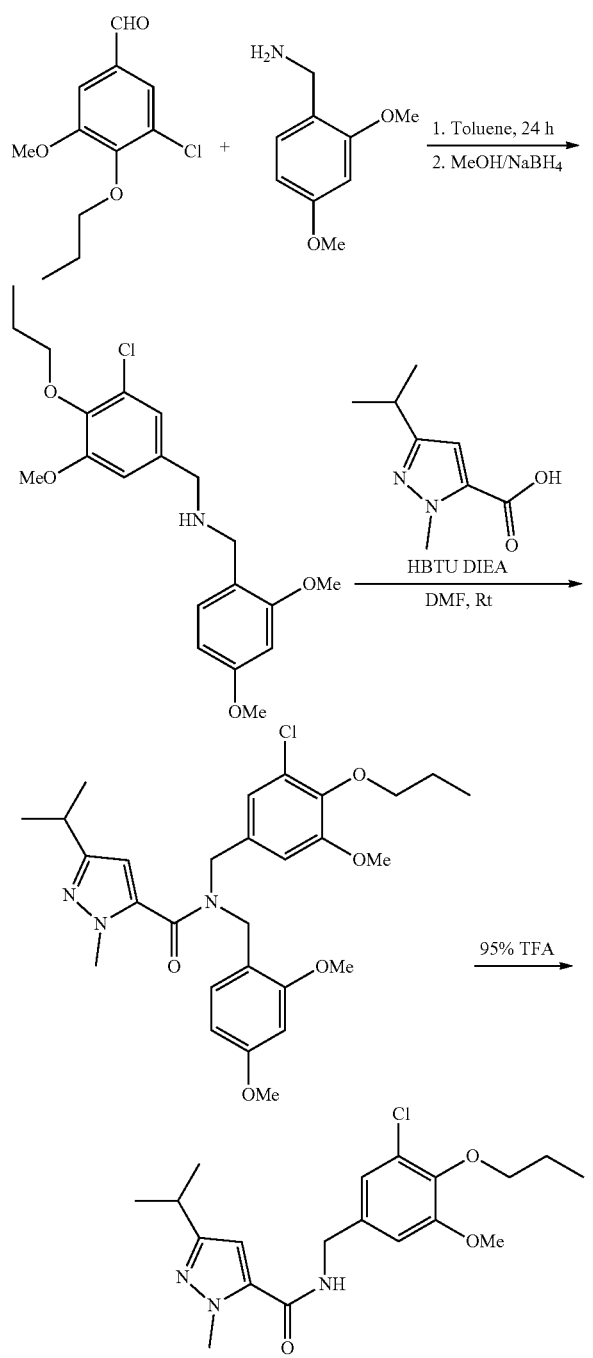

To a solution aldehyde (1.0 g, 4.34 mmol, 1.0 eq) in toluene (20 mL) was added 2,4-dimethoxybenzyl amine (732 mg, 4.34 mmol, 1.0 eq) and the reaction mixture was stirred at room temperature for 24 h. Toluene was removed to give a residue, which was taken in MeOH (25 mL) and then NaBH$_4$ (328 mg, 8.68 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (42.17 mmol, 1.0 eq) in DMF (20 mL) was added the acid (365 mg, 2.17 mmol, 1.0 eq), DIEA (1.40 g, 10.85 mmol, 5 eq) and HBTU (987 mg, 2.86 mmol, 1.2 eq) and the reaction mixture was stirred at rt for 12 h. The reaction mixture was then diluted with ethyl acetate (75 mL) and washed with 10% aqHCl (1×50 mL), sat NaHCO$_3$ (1×50 mL) and water (4×50 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For C$_{19}$H$_{27}$ClN$_3$O$_3$: 380.0 (M+H), Found 380.0.

43) N-(3-chloro-4-ethoxy-5-fluorobenzyl)-3-cyclopropyl-1-methyl-1H-pyrazole-5-carboxamide

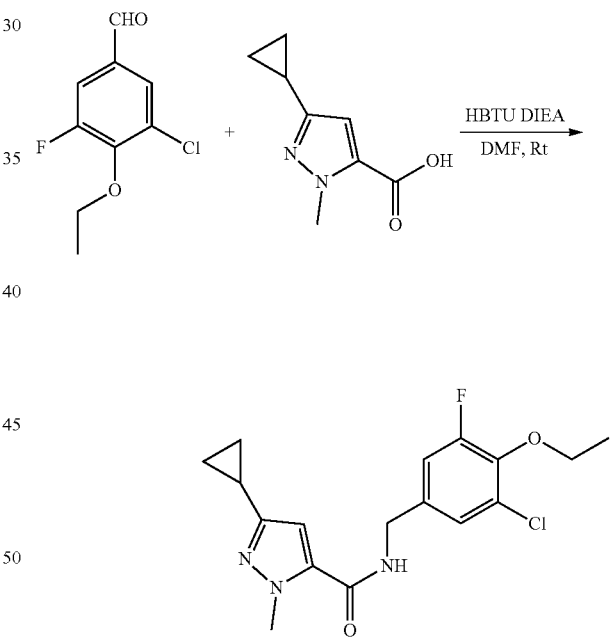

To a solution of amine (100 mg, 0.493 mmol, 1.0 eq) and acid (82 mg, 0.493 mmol, 1.0 eq) in DMF (5 mL) were added DIEA (318 mg, 2.47 mmol, 5 eq) and HBTU (224 mg, 0.592 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product (90 mg, >95% purity). Mass Spectrum (LCMS, ESI Pos.) Calcd. For C$_{17}$H$_{20}$ClFN$_3$O$_2$: 352.0 (M+H), Found 352.0.

44) N-(5-chloro-4-ethoxy-2-fluorobenzyl)-3-cyclopropyl-1-methyl-1H-pyrazole-5-carboxamide

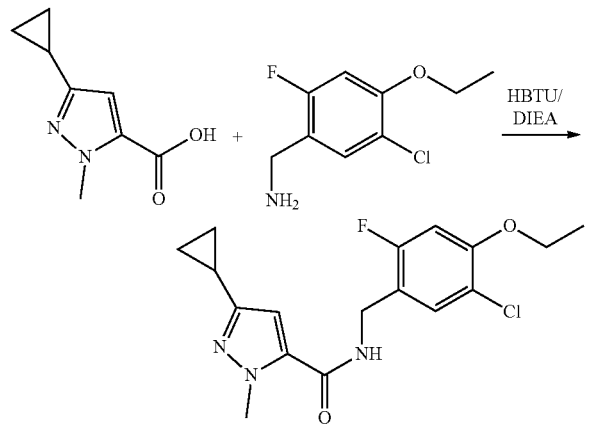

To a solution of amine (125 mg, 0.613 mmol, 1.0 eq) and acid (112 mg, 0.675 mmol, 1.1 eq) in DMF (10 mL) were added DIEA (395 mg, 3.065 mmol, 5 eq) and HBTU (224 mg, 0.592 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product (90 mg, >95% purity). Mass Spectrum (LCMS, ESI Pos.) Calcd. For $C_{17}H_{20}F_4N_3O_2$: 352.0 (M+H), Found 352.0.

45) 3-(tert-butyl)-N-((9-chloro-3,4-dihydro-2H-benzo[b][1,4]dioxepin-7-yl)methyl)-1-methyl-1H-pyrazole-5-carboxamide

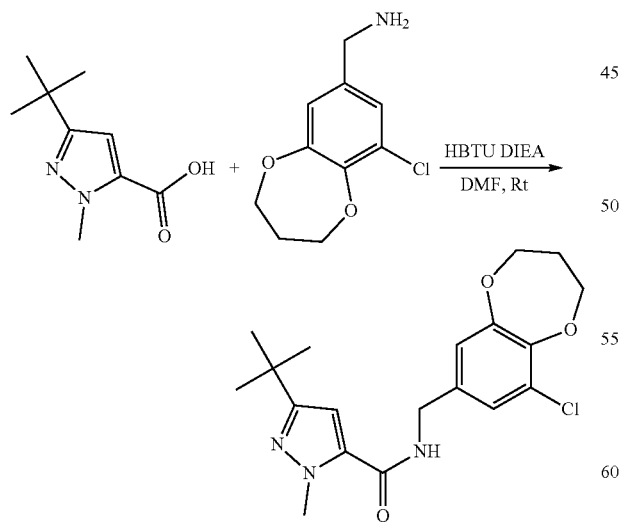

To a solution of amine (100 mg, 0.468 mmol, 1.0 eq) and acid (94 mg, 0.515 mmol, 1.1 eq) in DMF (8 mL) were added DIEA (302 mg, 2.34 mmol, 5 eq) and HBTU (213 mg, 0.562 mmol, 1.2 eq) and the reaction mixture was stirred at rt for 12 h. The reaction mixture was then diluted with ethyl acetate (20 mL) and washed with 10% aqHCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 10% to 50%) to give the desired product (63 mg, >95% purity). Mass Spectrum (LCMS, ESI Pos.) Calcd. For $C_{19}H_{25}ClN_3O_3$: 378.0 (M+H), Found 378.0.

46) 3-(tert-butyl)-N-(6-fluoro-2,3-dimethoxybenzyl)-1-methyl-1H-pyrazole-5-carboxamide

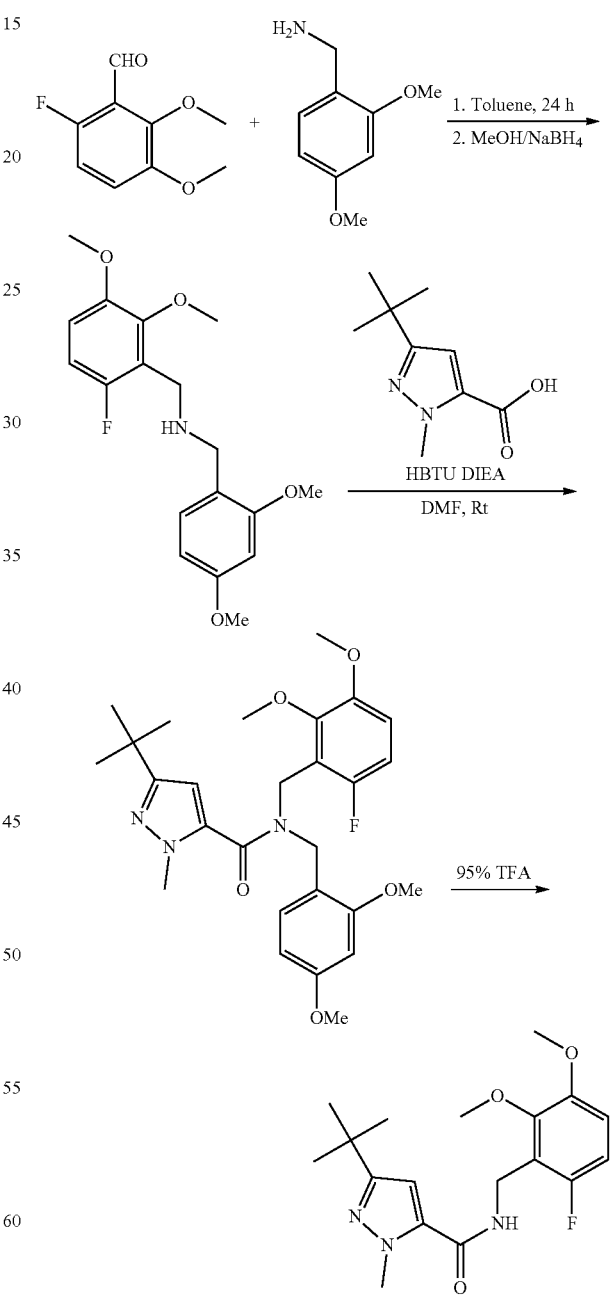

To a solution of aldehyde (250 mg, 1.36 mmol, 1.0 eq) in toluene (15 mL) was added 2,4-dimethoxybenzyl amine (227 mg, 1.36 mmol, 1.0 eq) and the reaction mixture was stirred at room temperature for 24 h. Toluene was removed to give a residue, which was taken in MeOH (15 mL) and then NaBH$_4$ (103 mg, 2.72 mmol, 2.0 eq) was added slowly. The reaction mixture was stirred at room temperature for 6 h. Solvent was removed and the residue was extracted in Ethyl acetate and stirred with saturated aq NaHCO$_3$ for 1 h. The organic layer was collected, dried and solvent was removed to give the crude amine, which was used in the next step without further purification. To a solution of the crude amine (0.45 mmol, 1.1 eq) in DMF (5 mL) were added the acid (75 mg, 0.407 mmol, 1.0 eq), DIEA (262 mg, 2.04 mmol, 5 eq) and HBTU (205 mg, 0.54 mmol, 1.2 eq) and the reaction mixture was stirred at rt for 12 h. The reaction mixture was then diluted with ethyl acetate (20 mL) and washed with 10% aq HCl (1×20 mL), sat NaHCO$_3$ (1×20 mL) and water (4×20 mL). Organic layer was collected, dried (MgSO$_4$) and evaporated to give a crude product, which was purified by column chromatography (EtOAc/Hexane 25% to 75%)) to give the amide, which was directly used in the next step. The amide was treated with 95% TFA:H$_2$O for 12 h. TFA was removed and azeotroped with toluene to give a residue, which was purified by column chromatography (EtOAc/Hexane 10% to 50%) to give the desired product. Mass Spectrum (LCMS, ESI Pos.) Calcd. For C$_{18}$H$_{25}$FN$_3$O$_3$: 350.0 (M+H), Found 350.0.

Example 2 a) Protocol for Antiviral Testing in Cell Culture

Adherent mammalian cells permissive for infection by the virus of interest are seeded and grown to 50-80% confluence. A viral stock is applied in appropriate medium at a multiplicity of infection substantially less than 1 (e.g. 0.01 to 0.1). This is in order to necessitate a second round of infection to achieve maximal viral titer, which in turn allows added compound to act on the entire viral lifecycle. An hour of so later (depending on the virus this time could be longer or shorter), virus is washed away, and fresh medium (typically 100 ul per 96 well plate) containing the compound of interest is added and cells cultured for an additional period of time ranging from 24-72 hrs, depending on virus, prior to harvesting medium.

One variation of this protocol is to harvest the medium, wash the cells with drug-free medium, and add fresh drug-free medium followed by a subsequent incubation (e.g. 2-4 hrs) and collection of medium. This allows viral particles that have been synthesized in the presence of drug, but which are released into the medium which does not contain drug, to be collected and tittered. If the compound shows strong antiviral activity in this post-treatment collection it argues strongly against a direct effect of the compound on the virus and is consistent with the expectation of a drug working on the host factors involved in capsid assembly. While the former effect may be of general interest, the focus of our platform is the pathway of host-catalyzed assembly and this variation allows us to be sure that we haven't been distract away from that specific mechanism of interest.

The harvested medium (either the original drug-containing medium or the 2 or 4 hour post treatment drug-free medium) is then serially diluted and viral titer determined by infection of a fresh plate of cells by TCID$_{50}$, assaying for either cytopathologic effect/death or immunoreactivity as determined by ELISA using virus-specific antibody. In either case, the endpoint titration determines the titer of infectious virus in the collected (and serially diluted) medium sample and therefore, by comparison to vehicle-treated control, a measure of antiviral effect of the compound (or lack thereof).

Example 3

Protocol for Influenza Virus Testing in Cell Culture

Compounds of the invention were tested for activity against Influenza virus according to the following protocol:
1. MDCK (Madin-Darby canine kidney)-2 cells were plated in three 96-well plates (3×104 per well) and cultured overnight. The next day the cells were inspected with a microscope to document the confluence. The required amount of wells were infected with the Influenza A virus (A/WSN/1933(H1N1)) with an MOI of 0.001 in triplicate. On each plate there were three infected wells that were cultured with cell culture medium without additional substance. There also were 3 wells on every plate that were not infected and served as controls for CPE determination, and 3 wells at each concentration of test substance or vehicle control.
2. Infection was performed for 1 hr at 37° C. in a cell culture incubator.
3. After infection the cells were washed once with infection-PBS. During washing the cell monolayer was inspected with a microscope, and damaged mono layers were excluded from testing. Uninfected wells were mock infected with infection-PBS and also inspected visually.
4. The pattern of substances on every individual plate was marked on the top of the plate and on a scheme.
5. An aliquot of 100 μL of diluted substance was added under subdued light and cells were incubated for 24 h. After incubation time the cell monolayer was again inspected and cpe was monitored and recorded. Medium was removed, cells washed with warm PBS and fresh drug-free medium added for 2 hrs in cell culture incubator at 37° C. and the medium collected for TCID$_{50}$ determination of viral titer.
6. The dilutions for the titration were generated in a 96-well plate by diluting the supernatants 1:10. A 100 μL aliquot of undiluted supernatant and five dilutions (from 10$^{-1}$ to 10$^{-5}$) were used to infect 96-well plates of MDCK cell monolayers which were incubated for 72 hrs after which cpe was monitored and scored.
7. Aliquots of medium can be saved for ELISA with anti-influenza antibodies to corroborate that cpe was due to influenza infection.
8. The original cell plate can be assayed by AlamarBlue cell toxicity assay to determine if the presence of compound resulted in lesser or greater toxicity at 24 hrs than would have been observed without infection or with vehicle control.

Results:

| Compound | EC90 uM |
| --- | --- |
| 1 | 0.4 |
| 2 | 0.1 |
| 3 | 1.1 |
| 4 | 0.1 |
| 5 | 1.5 |
| 6 | 1.5 |
| 7 | 1.8 |
| 8 | 1.5 |
| 9 | 0.4 |
| 10 | 0.1 |
| 11 | 1.5 |

-continued

| Compound | EC90 uM |
|---|---|
| 12 | 1.8 |
| 13 | 0.4 |
| 14 | 0.4 |
| 15 | 0.4 |
| 16 | 1.0 |
| 17 | 0.4 |
| 18 | 1.5 |
| 19 | 1.5 |
| 20 | 1.5 |
| 21 | 2.0 |
| 22 | 0.3 |
| 23 | |
| 24 | 0.2 |
| 25 | 0.4 |
| 26 | 0.8 |
| 27 | 1.5 |
| 28 | 1.5 |
| 29 | 1.5 |
| 30 | 0.3 |
| 31 | 1.0 |
| 32 | 1.0 |
| 33 | 1.5 |
| 34 | 1.2 |
| 35 | 0.2 |
| 36 | 0.1 |
| 37 | 0.1 |
| 38 | 0.1 |
| 39 | 0.1 |
| 40 | 0.4 |
| 41 | 0.4 |
| 42 | 0.2 |
| 43 | 0.4 |
| 44 | 0.4 |
| 45 | 1.0 |
| 46 | 1.0 |

\* EC90 values represents efficacy of the compound where 90% of the virus was inhibited. EC90 values are derived using the TCID50 (Tissue-culture infective dose) assay.

It is understood that the examples and embodiments described herein are for illustrative purposes only and that various modifications or changes in light thereof will be suggested to persons skilled in the art and are to be included within the spirit and purview of this application and scope of the appended claims. It is to be understood that the present invention covers all combinations of aspects and/or embodiments, as well as suitable, convenient and preferred groups described herein. All publications, patents, and patent applications cited herein are hereby incorporated by reference in their entirety for all purposes.

The invention is further illustrated by the Examples that follow. The Examples are not intended to define or limit the scope of the invention.

What is claimed is:

1. A compound according to either formula (I) or (II):

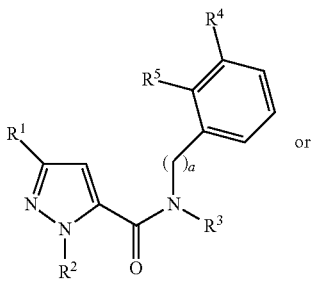

(I)

or

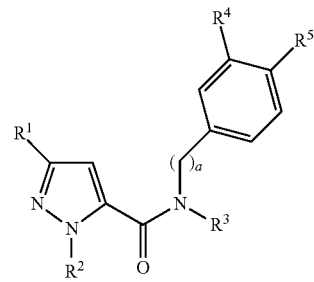

(II)

in which $R^1$ and $R^2$ are each independently selected from branched alkyl, and cycloalkyl; $R^3$ is H; a is an integer selected from 1, 2, 3, 4, 5, and 6; $R^4$ and $R^5$ are each independently selected from linear alkyl, branched alkyl, halosubstituted alkyl, cycloalkyl, linear alkoxy, branched alkoxy, halosubstituted alkoxy, cycloalkoxy, and halogen, or a hydrate, or a salt, or a solvate thereof.

2. A compound which is:

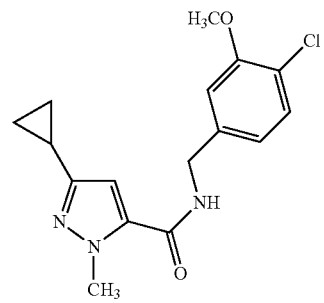 [SMILES: COc1cc(CNC(=O)c2cc(C3CC3)nn2C)ccc1Cl]

or a hydrate, or a salt, or a solvate thereof.

3. A compound which is:

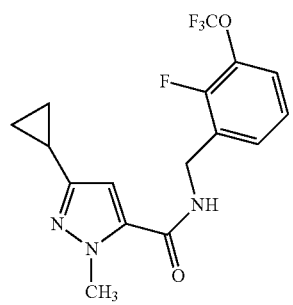 [SMILES: Cn1nc(C2CC2)cc1C(=O)NCc1cccc(OC(F)(F)F)c1F]

or a hydrate, or a salt, or a solvate thereof.

4. A compound which is:

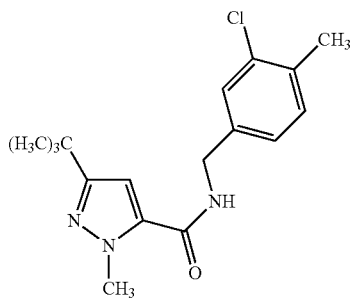 [SMILES: Cc1ccc(CNC(=O)c2cc(C(C)(C)C)nn2C)cc1Cl]

or a hydrate, or a salt, or a solvate thereof.

5. A pharmaceutical formulation comprising:
   a) a compound of claim 1, or a pharmaceutically acceptable salt thereof; and
   b) a pharmaceutically acceptable excipient.

6. A method of inhibiting the replication of a virus in an animal, comprising:
   a) administering a compound of claim 1 to the animal, wherein the animal is in need of treatment thereof
thereby inhibiting the replication of the virus in an animal.

7. The method of claim 6, wherein the virus is a member of the Orthomyxoviridae family.

8. The method of claim 6, wherein the virus is influenzavirus A or influenzavirus B or influenzavirus C.

9. A method of treating a disease in an animal, comprising:
   a) administering a compound of claim 1 to the animal, wherein the animal is in need of treatment thereof
thereby treating the disease in the animal.

10. The method of claim 9, wherein the disease is influenza.

11. The method of claim 6, wherein the animal is a human.

12. The method of claim 6, wherein the animal is a pig.

13. A method of treating porcine epidemic diarrheal virus infection in a pig, the method comprising administering to said pig a therapeutically effective amount of a compound of claim 1, wherein the pig is in need of treatment thereof, thereby treating porcine epidemic diarrheal virus infection in the pig.

14. The compound of claim 1, wherein a is 1.

15. The compound of claim 1, wherein $R^2$ is methyl.

16. The compound of claim 1, wherein $R^1$ is branched $C_3$-$C_6$ alkyl.

17. The compound of claim 1, wherein $R^1$ is t-butyl.

18. The compound of claim 1, wherein $R^1$ is $C_3$-$C_8$ cycloalkyl.

19. The compound of claim 1, wherein $R^1$ is cyclopropyl.

20. The compound of claim 1, wherein $R^4$ and $R^5$ are each independently selected from linear alkyl, branched alkyl, halosubstituted alkyl, linear alkoxy, branched alkoxy, and halosubstituted alkoxy.

21. The compound of claim 1, wherein $R^5$ is linear alkoxy.

22. The compound of claim 1, wherein $R^5$ is methoxy.

23. The compound of claim 1, wherein $R^4$ is halosubstituted alkoxy.

24. The compound of claim 1, wherein $R^4$ is halosubstituted methoxy.

25. The compound of claim 1, wherein $R^4$ is trifluoromethoxy.

26. The compound of claim 1, wherein $R^5$ is $C_1$-$C_6$ alkoxy, and $R^4$ is halosubstituted $C_1$-$C_6$ alkoxy.

27. The compound of claim 1, wherein $R^5$ is $C_1$-$C_3$ alkoxy, and $R^4$ is halosubstituted $C_1$-$C_3$ alkoxy.

28. The compound of claim 1, wherein $R^5$ is methoxy or ethoxy, and $R^4$ is halosubstituted $C_1$-$C_3$ alkoxy.

29. The compound of claim 1, wherein $R^5$ is methoxy, and $R^4$ is halosubstituted methoxy.

30. The compound of claim 1, wherein $R^5$ is methoxy, and $R^4$ is trifluoromethoxy.

31. The compound of claim 1, wherein $R^4$ is trifluoromethoxy, and $R^2$ is methyl.

32. The compound of claim 1, wherein $R^4$ is trifluoromethoxy, and $R^1$ is cyclopropyl.

33. The compound of claim 1, wherein a is 1, and $R^2$ is methyl.

34. The compound of claim 1, wherein a is 1, $R^1$ is cyclopropyl or t-butyl, and $R^2$ is methyl.

35. The compound of claim 1, wherein a is 1, $R^5$ is methoxy or ethoxy, and $R^2$ is methyl.

36. The compound of claim 1, wherein the compound is 3-cyclopropyl-N-(2-methoxy-3-(trifluoromethoxy)benzyl)-1-methyl-1H-pyrazole-5-carboxamide.

* * * * *

UNITED STATES PATENT AND TRADEMARK OFFICE
CERTIFICATE OF CORRECTION

PATENT NO. : 10,532,980 B2
APPLICATION NO. : 15/561933
DATED : January 14, 2020
INVENTOR(S) : Suganya Selvarajah et al.

Page 1 of 1

It is certified that error appears in the above-identified patent and that said Letters Patent is hereby corrected as shown below:

In the Claims

Column 107:
In Claim 1, Line 15, please replace as shown:
in which $R^1$ is branched alkyl or cycloalkyl; and $R^2$ is linear alkyl; $R^3$ is H, a is an integer selected from 1, 2, 3, 4, 5, and 6; $R^4$ and $R^5$ are each independently selected from linear alkyl, branched alkyl, halosubstituted alkyl, cycloalkyl, linear alkoxy, branched alkoxy, halosubstituted alkoxy, cycloalkoxy, and halogen, Signed and Sealed this
Thirtieth Day of June, 2020

Andrei Iancu
*Director of the United States Patent and Trademark Office*